US011447482B1

(12) United States Patent
Liu et al.

(10) Patent No.: US 11,447,482 B1
(45) Date of Patent: Sep. 20, 2022

(54) IMIDAZOPYRIDINE AND OXAZOLOPYRIDINE DERIVATIVES AND ANALOGS THEREOF, METHODS OF PREPARATION THEREOF, METHODS OF HIF-2A PATHWAY INHIBITION, AND INDUCTION OF FERROPTOSIS

(71) Applicant: KUDA Therapeutics, Inc., Salt Lake City, UT (US)

(72) Inventors: Xiaohui Liu, Salt Lake City, UT (US); Mei Yee Koh, Salt Lake City, UT (US)

(73) Assignee: KUDA THERAPEUTICS, INC., Salt Lake City, UT (US)

( * ) Notice: Subject to any disclaimer, the term of this patent is extended or adjusted under 35 U.S.C. 154(b) by 35 days.

(21) Appl. No.: 16/791,148

(22) Filed: Feb. 14, 2020

Related U.S. Application Data

(60) Provisional application No. 62/805,699, filed on Feb. 14, 2019.

(51) Int. Cl.
| | |
|---|---|
| *C07D 417/12* | (2006.01) |
| *C07D 471/04* | (2006.01) |
| *A61P 35/00* | (2006.01) |
| *C07D 487/04* | (2006.01) |
| *C07D 513/04* | (2006.01) |
| *C07D 498/04* | (2006.01) |

(52) U.S. Cl.
CPC ............ *C07D 417/12* (2013.01); *A61P 35/00* (2018.01); *C07D 471/04* (2013.01); *C07D 487/04* (2013.01); *C07D 498/04* (2013.01); *C07D 513/04* (2013.01)

(58) Field of Classification Search
CPC .. C07D 417/12; C07D 471/04; C07D 487/04; C07D 498/04; C07D 513/04
See application file for complete search history.

(56) References Cited

U.S. PATENT DOCUMENTS

| | | | |
|---|---|---|---|
| 6,358,978 B1 | 3/2002 | Ritzeler et al. | |
| 7,235,537 B2 | 6/2007 | Wallace et al. | |
| 8,377,975 B2 | 2/2013 | Klein et al. | |
| 8,796,320 B2 | 8/2014 | Asai et al. | |
| 2012/0136003 A1 | 5/2012 | Russell et al. | |
| 2015/0218148 A1* | 8/2015 | Dahl | A61K 31/4245 514/44 R |
| 2018/0072708 A1 | 3/2018 | Yanagisawa et al. | |
| 2018/0203175 A1 | 7/2018 | Kiuchi et al. | |

FOREIGN PATENT DOCUMENTS

| | | |
|---|---|---|
| WO | 2003/059289 A2 | 7/2003 |
| WO | 2011/081205 A1 | 7/2011 |
| WO | 2014/036242 A1 | 3/2014 |
| WO | WO-2019018718 A1 * | 1/2019 ........... C07D 417/12 |

OTHER PUBLICATIONS

Khan; J. Agric. Food Chem. 1990, 38, 4, 1068-1071. DOI: 10.1021/jf00094a034 (Year: 1990).*
Akhtar; European Journal of Medicinal Chemistry 2017, 126, 853-869. DOI: 10.1016/j.ejmech.2016.12.014 (Year: 2017).*
Masoud; Anticancer Research 2015, 35, 3849-3859. (Year: 2015).*
Fallah; Current Oncology Reports (2019) 21: 6. 10 pages. DOI: 10.1007/s11912-019-0752-z (Year: 2019).*
Priyanka; International Journal of Pharmacy and Biological Sciences 2014, 4(3), 120-125. (Year: 2014).*
Ramya V. Shingalapur et al., *Derivatives of Benzimidazole Pharmacophore: Synthesis, Anticonvulsant, Antidiabetic and DNA Cleavage Studies*, European Journal of Medicinal Chemistry, 45 (2010), pp. 1753-1759.
Lallan Mishra et al., *Synthesis and Fungicidal Activity of Some 5-Membered Heterocyclic Derivatives Containing Benzimidazoles*, Bioscience, Biotechnology, and Biochemistry, 57(6), 1993, pp. 989-991.
Mohd Amir et al., *Synthesis of Pharmaceutically Important 1,3,4-thiadiazole and Imidazolinone Derivatives as Antimicrobials*, Indian Journal of Chemistry, vol. 48B, Sep. 2009, pp. 1288-1293.
Bereket Mochana et al., *Synthesis of Some Benzimidazole Derivatives Bearing 1,3,4-Oxadiazole Moiety as Anticancer Agents*, Chem. Sci. Trans., 4(2), Apr. 2015, pp. 534-540.
Asif Husain et al., *Benzimidazole Bearing Oxadiazole and Triazolo-Thiadiazoles Nucleus: Design and Synthesis as Anticancer Agents*, Bioorganic & Medicinal Chemistry Letters 22 (2012), pp. 5438-5444.
Mohd Rashid et al., *Synthesis of Benzimidazoles Bearing Oxadiazole Nucleus as Anticancer Agents*, European Journal of Medicinal Chemistry 54 (2012) pp. 855-866.
Norizan Ahmat et al., *Synthesis and Characterization of Oxadiazole Derivatives from Benzimidazole*, Malaysian Journal of Analytical Sciences, vol. 20, No. 6, 2016, pp. 1515-1523.
B. Vishwanathan et al., *Anticoagulant Evaluation of 1,3,4-Oxadiazole Derivatives Derived from Benzimidazole*, World Journal of Pharmaceutical Sciences, Nov. 2014, pp. 4.
M.S.R. Murty et al., *Synthesis of Piperazinyl Benzothiazole/ Benzoxazole Derivatives Coupled with 1,3,4-oxadiazole-2-thiol: Novel Hybrid Heterocycles as Anticancer Agents*, Med Chem Res 22 (2013), pp. 4980-4991.
Vinayak S. Hedge et al., *Dimethyldithioimidocarbonates-Mediated Heterocyclizations: Synthesis of Imidazolidines and Benzheterocycles as Potent Antitubercular Agents*, Phosphorus, Sulfur, and Silicon, 182, 2007, ppl 911-920.

* cited by examiner

Primary Examiner — Daniel R Carcanague
(74) Attorney, Agent, or Firm — Workman Nydegger

(57) ABSTRACT

Novel substituted imidazopyridine and oxazolopyridine compounds that are useful as inhibitors of HIF-2α and inducers of ferroptosis through perturbations in iron metabolism, synthetic methods for making said compounds, pharmaceutical compositions comprising the compounds, and methods of using the compounds and compositions to treat disorders associated with dysfunction of HIF-2α or iron metabolism.

20 Claims, 13 Drawing Sheets

A)

B)

| | IC$_{50}$ (µM) | |
|---|---|---|
| Compound | Viability (Control) | Viability (+DFO) |
| KD002 | 11.27 | 30.65 |
| KD021 | 11.36 | 83.63 |
| KD025 | 2.7 | 5.6 |

A)

B)

ical Field

The present disclosure relates to novel compounds and more particularly to imidazopyridine and oxazolopyridine derivative and analogs thereof as well as methods of making and using such compounds.

2. Related Technology

Hypoxia provides the required extracellular stimulus for proper embryogenic development and wound healing, and maintains the pluripotency of stem cells. Apart from these cellular processes, pathological hypoxia can be caused by a reduction in oxygen supply such as at high altitude, or caused by localized ischemia due to the disruption of blood flow to a given area. Additionally, most solid tumors contain hypoxic regions because of the severe structural abnormality of tumor blood vessels, and the rapid growth of tumor cells themselves which frequently outstrip levels of available oxygen (Pouyssegur, Dayan et al. 2006).

The hypoxia-inducible factor (HIF) transcription factors are central mediators of the response to low oxygen or hypoxia (Wang, Jiang et al. 1995, Wilson and Hay 2011, Koh and Powis 2012).

The HIFs are heterodimers comprising one of three major oxygen labile HIF-α subunits (HIF-1α, HIF-2α and HIF-3α), and a constitutive HIF-1β subunit (also known as aryl hydrocarbon receptor nuclear translocator or ARNT), which together form the HIF-1, HIF-2 and HIF-3 transcriptional complexes respectively (Wang, Jiang et al. 1995). Of the three α-subunits, HIF-1α and HIF-2α have been the most studied.

In the presence of oxygen, HIF-α is hydroxylated by specific prolyl hydroxylases (PHDs) at two conserved proline residues (P402/P564 and P405/P531 for human HIF-1a and HIF-2a respectively) situated within the oxygen-dependent degradation domain (ODD) in a reaction requiring oxygen, 2-oxoglutarate, ascorbate, and iron ($Fe^{2+}$) as a cofactor. HIF-α hydroxylation facilitates binding of von Hippel-Lindau protein (pVHL) to the HIF-α ODD (Jaakkola, Mole et al. 2001). pVHL forms the substrate recognition module of an E3 ubiquitin ligase complex comprising elongin C, elongin B, cullin-2, and ring-box 1, which directs HIF-1/2a poly-ubiquitylation and proteasomal degradation (Ohh, Park et al. 2000). Under hypoxic conditions, PHD activity is inhibited, pVHL binding abrogated, and HIF-α is stabilized and enters the nucleus, where it heterodimerizes with HIF-1β and binds to a conserved DNA sequence known as the hypoxia responsive element (HRE), to transactivate a variety of hypoxia-responsive genes (Maxwell, Pugh et al. 2001).

The HIFs activate transcription of hundreds of genes critical for the adaptation to hypoxia, and for tumor progression, such as those promoting aerobic glycolysis, angiogenesis, and metastasis (Wang, Jiang et al. 1995, Wilson and Hay 2011). Despite sharing many transcriptional targets, the HIFs also play non-redundant roles. For example, anerobic glycolysis appears to be predominantly controlled by HIF-1, whereas erythropoietin (EPO) synthesis and iron metabolism have emerged as HIF-2-regulated processes (Hu, Wang et al. 2003, Gruber, Hu et al. 2007, Rankin, Biju et al. 2007, Kapitsinou, Liu et al. 2010). Furthermore, in addition to canonical HRE-mediated transcription, which requires heterodimerization with HIF-1p, the HIF-1a and HIF-2a subunits differentially modulate cellular signaling pathways through interaction with proteins that do not contain PAS domains, including the tumor suppressor protein p53, the c-MYC proto-oncogene, β-catenin and the Notch intracellular domain (An, Kanekal et al. 1998, Ravi, Mookerjee et al. 2000, Koshiji, Kageyama et al. 2004, Gustafsson, Zheng et al. 2005, Bertout, Majmundar et al. 2009, Choi, Chun et al. 2010).

Tumor hypoxia is of major clinical significance because it promotes both tumor progression and resistance to therapy (Vaupel and Mayer 2007). In addition to promoting tumor cell survival by shifting cells towards anaerobic metabolism, neovascularization and resistance to apoptosis, hypoxia drives other responses that contribute to tumor aggressiveness, such as increased genetic instability, invasion, metastasis and de-differentiation, largely through activation of the HIFs (Wilson and Hay 2011).

Elevated levels of tumor HIF-1a are associated with poor patient prognosis in multiple tumor types (Zhong, De Marzo et al. 1999). Elevated HIF-2a is also associated with poor prognosis in specific tumor types such as clear cell renal cell carcinoma (CCRCC), which is the most common and aggressive type of kidney cancer, neuroblastoma, glioblastoma (GBM) and non-small cell lung cancer (Holmquist-Mengelbier, Fredlund et al. 2006, Franovic, Holterman et al. 2009).

The pro-tumorigenic role of HIF-2a is particularly clear in CCRCC. CCRCC is most typically initiated by loss of pVHL, resulting in the pseudo-hypoxic activation of both HIF-1 and HIF-2. However, HIF-2α drives tumor progression in CCRCC, whereas HIF-1α, whose expression is frequently lost, inhibits growth and predicts for better patient prognosis (Shen, Beroukhim et al. 2011). This antagonistic effect might be explained by the unique ability of HIF-2α to co-operate with and potentiate c-Myc transcriptional activity, thus stimulating cellular proliferation in CCRCC. By contrast, c-Myc activity and CCRCC cell proliferation is inhibited by HIF-1a (Gordan, Lal et al. 2008). The HIF-2 bias observed in CCRCC may also be attributed to the increased potency of HIF-2α compared to HIF-1a in promoting pro-tumorigenic factors such as Cyclin D1, TGF-α and VEGFA (Raval, Lau et al. 2005, Dowd, Ibrahim et al. 2014). HIF-2α has also been implicated in CCRCC metastasis through activation of CXCR4, which is associated with poor patient prognosis (Vanharanta, Shu et al. 2013, Micucci, Matacchione et al. 2015). Finally, HIF-2α also regulates translation of EGFR, which has been associated with resistance to a variety of anti-angiogenic therapies (Raval, Lau et al. 2005, Gordan, Lal et al. 2008, Uniacke, Holterman et al. 2012). Taken together, the data support the selective inhibition of HIF-2α as an attractive therapeutic strategy for CCRCC (Chen, Hill et al. 2016, Cho, Du et al. 2016, Ricketts, Crooks et al. 2016, Martinez-Saez, Gajate Borau et al. 2017).

There is an unmet need for new treatments for CCRCC, which is highly refractory to standard chemotherapy and radiation, and patients with advanced or metastatic tumors have a 5-year survival rate of <20% (Lara and Jonasch 2012). Furthermore, many CCRCCs remain asymptomatic, and approximately 30% of patients with CCRCC present with metastatic disease (Baldewijns, van Vlodrop et al. 2010, Lara and Jonasch 2012). Current treatments include a variety of anti-angiogenic agents (primarily kinase inhibitors), which are limited by the inevitable development of resistance, and newer immune checkpoint inhibitors, which elicit responses only in 20-25% of patients (Brugarolas 2007, Rini and Flaherty 2008, Rini and Atkins 2009, Coppin, Kollmannsberger et al. 2011, Jonasch, Futreal et al. 2012, Topalian, Hodi et al. 2012, Fisher, Gore et al. 2013, Motzer, Escudier et al. 2015, Motzer, Rini et al. 2015, Sharma and Allison 2015).

In addition to its role in promoting tumor progression, excess production of HIF-2α caused by activating mutations within EPAS1 (the gene that encodes HIF-2α), or inactivating mutations of pVHL or PHD2 can lead to excessive production of red blood cells or polycythemia (Ang, Chen et al. 2002, Percy, Zhao et al. 2006, Percy, Beer et al. 2008, Percy, Furlow et al. 2008, Percy, Chung et al. 2012). This is primarily mediated by increased HIF-2α-dependent production of erythropoietin (EPO), a cytokine which promotes red blood cell production (Franke, Gassmann et al. 2013). By contrast, mutations in HIF-1a have not been associated with altered red blood cell production. Mutations in EPAS1 have not only been shown to lead to polycythemia but have also been described to cause neoplasia, in particular paragangliomas (Zhuang, Yang et al. 2012, Yang, Sun et al. 2015). Consistent with its unique role in regulating erythropoiesis, inactivating mutations of EPAS have been associated with adaptation to high altitude, reducing the elevated red blood cell production and high blood viscosity associated with non-altitude adapted populations (van Patot and Gassmann 2011). By contrast, mutations in HIF-1a have not been associated with adaptation to high altitude. Thus, selective inhibition of HIF-2α may provide benefit for polycythemia associated with pVHL, PHD2 or EPAS1 mutation, or through excessive production of EPO. Additionally, selective HIF-2α inhibition may be beneficial for the treatment of paragangliomas associated with EPAS1 mutations. Finally, HIF-2α inhibition may provide benefit for the treatment of altitude sickness associated with elevated blood viscosity.

A novel approach for inhibiting HIF-2α transcriptional activity through disruption of the HIF-2α/HIF-1β heterodimer is currently under development for the treatment of CCRCC (Courtney, Infante et al. 2016). However, this approach of inhibiting HIF-2 transcriptional activity does not address the non-transcriptional targets of HIF-2α such as c-Myc, EGFR and β-catenin, which are activated by protein-protein interaction with HIF-2α, and have also been associated with tumor progression and resistance to therapy (Gordan, Lal et al. 2008, Choi, Chun et al. 2010, Uniacke, Holterman et al. 2012).

Since oxygen delivery is tightly linked to iron availability, both oxygen and iron deprivation have very similar molecular consequences. Consistent with the central role of HIF-2α in the regulation of iron homeostasis, HIF-2α (but not HIF-1α) is also regulated by iron due to the presence of an RNA stem-loop element known as an iron-responsive element (IRE), in the 5' untranslated region (UTR) of the HIF-2α transcript. Under conditions of iron deprivation, IRE-binding proteins (IRP1 and IRP2) bind to IREs within 5' or 3' UTRs of transcripts resulting in translational repression and transcript stabilization respectively.

The IRPs coordinate the cellular response to iron depletion by decreasing iron storage and increasing iron uptake through downregulation of the central iron storage molecule, ferritin (both heavy and light chains; 5'IRE) and upregulation of the major mediator of cellular iron uptake, transferrin receptor (TfR1; 3'IRE) respectively. Studies using genetically engineered mouse models have shown that IRP2 is the central post-transcriptional regulator of iron metabolism, whereas IRP1 plays a non-redundant role in the regulation of HIF-2α primarily within the kidney, where IRP1 is most highly expressed (Meyron-Holtz, Ghosh et al. 2004, Anderson, Nizzi et al. 2013, Ghosh, Zhang et al. 2013).

Under conditions of iron deprivation, IRP1 binds the IRE within the 5'UTR of HIF-2α, repressing the translation of HIF-2α. Similarly, under iron-deprived conditions, IRP2 is stabilized and binds the 5'IRE of ferritin, repressing translation of ferritin which decreases iron storage. Conversely, IRP2 also binds the 3'IRE of TfR1 to promote iron uptake. Consequently, conditions of cellular iron deprivation can be indicated by elevated levels of IRP2, TfR1 and decreased levels of ferritin (both heavy and light chains, FTH1, FTL).

The IRE binding activities of IRP1 and IRP2 are induced by distinct stimuli: IRP1 by disruption of its [4Fe-4S] cluster (such as by oxidative stress or nitric oxide), and IRP2 by iron or oxygen depletion (Pantopoulos, Weiss et al. 1996, Pantopoulos, Mueller et al. 1997, Hanson, Foot et al. 1999, Meyron-Holtz, Ghosh et al. 2004, Wang, Chen et al. 2004, Anderson, Nizzi et al. 2013, Ghosh, Zhang et al. 2013). These distinct regulatory mechanisms may facilitate the specific induction of IRP1 IRE-binding by disruption of its [4Fe-4S] cluster.

Together with its binding partners ISCA1 and IBA57, ISCA2 is required for the maturation of a subset of mitochondrial [4Fe-4S] proteins, and potentially plays a role in the assembly of [2Fe-2S] proteins in both the mitochondrial and cytoplasm (Sheftel, Wilbrecht et al. 2012)(Beilschmidt, Ollagnier de Choudens et al. 2017, Ciofi-Baffoni, Nasta et al. 2018).

Iron is critically required by tumor cells to enable the function of key proteins involved in DNA replication, maintenance of genomic integrity (including DNA repair), and cell cycle progression; which are frequently upregulated in cancer. Additionally, many signaling pathways known to drive cancer such as Wnt, PI-3K/AKT/mTor, and Ras/Raf/MEK/ERK require iron, and are inhibited by iron deprivation (Song, Christova et al. 2011, Dixon, Lui et al. 2013, Lui, Kovacevic et al. 2015).

The increased demand for iron by tumor cells, and alterations in the pathways of iron acquisition and utilization are among the key metabolic changes that are the hallmarks of cancer (Pinnix, Miller et al. 2010, Torti and Torti 2013, Zhang and Zhang 2015). This includes the elevation of both TfR1 and circulating ferritin in a variety of cancer types that are associated with tumor progression (Alkhateeb and Connor 2013, Torti and Torti 2013). Thus, antibodies targeting TfR1 for functional neutralization, or for internalization of conjugated toxic moieties are currently being developed as anti-cancer strategies (Baron-Van Evercooren, Olichon-Berthe et al. 1991). Additionally, the ability of tumor associated macrophages (TAMs) to promote tumor growth has been linked to the capacity of TAMs to release iron into the local microenvironment as part of a wound healing response (Jung, Mertens et al. 2015).

Despite the well-established link between iron and cancer, current therapeutic strategies for iron depletion are limited to iron chelation, which is non-specific and carries significant side effects (eg. grade 3/4 neutropenia in 79% of patients in a Phase II CCRCC trial), limiting its utility (Knox, Hotte et al. 2007, Bedford, Ford et al. 2013).

Ferroptosis is a newly identified form or regulated cell death that is iron- and reactive oxygen species dependent (Dixon, Lemberg et al. 2012). Since the evasion of apoptosis-mediated cell death is a characteristic feature of human cancers, therapies that mediate non-apoptotic mechanisms of cell death are attractive treatment strategies for cancer. Additionally, the aberrantly elevated levels of iron in many cancer types may predispose them to ferroptosis, providing a measure of selectivity that spares normal tissue.

Ferroptosis is a form of necrotic cell death associated with iron-dependent oxidation of phospholipid membranes, which leads to loss of selective permeability of the plasma membrane, and defects in the mitochondrial membrane (Dixon, Lemberg et al. 2012, Mou, Wang et al. 2019). In addition to iron, other transition metals such as zinc also promote ferroptosis (Palmer, Jordan et al. 2019). Initial studies characterizing ferroptosis have demonstrated that classic features of apoptosis, such as mitochondrial cytochrome c release, caspase activation and chromatin fragmentation, are not observed in ferroptotic cells (Dolma, Lessnick et al. 2003, Yagoda, von Rechenberg et al. 2007, Yang and Stockwell 2008). Ferroptosis is, however, associated with increased levels of intracellular reactive oxygen species (ROS) and is prevented by iron chelation or genetic inhibition of cellular iron uptake (Yagoda, von Rechenberg et al. 2007, Yang and Stockwell 2008). In a recent systematic study of various mechanistically unique lethal compounds, the prevention of cell death by iron chelation was a rare phenomenon (Wolpaw, Shimada et al. 2011), suggesting that few triggers can access iron-dependent lethal mechanisms.

The canonical pathway for ferroptosis induction involves the inactivation of the central protective mechanisms of membranes against peroxidation damage, including those regulating cysteine availability and glutathione biosynthesis (Dixon, Lemberg et al. 2012). The selenoenzyme, glutathione peroxidase 4 (GPX4), is the only enzyme thus far shown to be able to directly reduce complex hydroperoxides, and thus protect cells from ferroptosis, and can be inactivated through direct or indirect targeting mechanisms such as depletion of intracellular glutathione (Dixon, Lemberg et al. 2012, Yang, SriRamaratnam et al. 2014, Yang, Kim et al. 2016). A number of potent ferroptosis inducers that trigger ferroptosis in vitro such as by depleting intracellular glutathione or GPX4 have been described, but these are unsuitable as clinical candidates since many target nodes that may be bypassed in vivo, or require high amounts of inducers or additional delivery vehicles for activity (Schneider, Wortmann et al. 2010, Yang, SriRamaratnam et al. 2014, Zhang, Tan et al. 2019).

There is a compelling rationale for the induction of ferroptosis for the treatment of cancer in general, and of clear cell kidney cancer, in particular. First, pVHL loss, the initiating event in CCRCC, promotes metabolic reprogramming that increases lipid storage and impairs fatty acid oxidation, sensitizing CCRCC cells to ferroptosis (Miess, Dankworth et al. 2018). In this regard, HIF-2α, which is elevated as a result of pVHL deficiency, selectively enriches for polyunsaturated lipids, the rate-limiting substrates for the lipid peroxidation associated with ferroptosis (Zou, Palte et al. 2019). Hence, CCRCC cells are exquisitely sensitive to ferroptosis induction, in particular, to the inhibition of GPX4 (Zou, Palte et al. 2019). Second, CCRCC is an iron-enriched tumor, which also increases susceptibility to ferroptosis (Yang, Kim et al. 2016). Third, CCRCC cells exhibit substantially higher sensitivity to ferroptosis that normal renal cells, suggesting the existence of a therapeutic window for inducing tumor cell death via ferroptosis without affecting normal tissue function (Zou, Palte et al. 2019). Fourth, a non-mutational state associated with a mesenchymal-like phenotype and resistance to standard therapies has been associated with ferroptosis sensitivity, suggesting the potential utility of ferroptosis-inducers in drug-resistant tumors (Viswanathan, Ryan et al. 2017). Finally, the ferroptosis-sensitive state has also been associated with an immunosuppressive phenotype, suggesting that cells resistant to immune checkpoint inhibitors may show increased sensitivity to ferroptosis (Friedmann Angeli, Krysko et al. 2019).

BRIEF SUMMARY

The present disclosure relates to novel compounds and more particularly to imidazopyridine and oxazolopyridine derivative and analogs thereof as well as methods of making and using such compounds. The present disclosure further relates to the use of these compounds as a medicament. In certain embodiments, contemplated is the treatment of disorders associated with HIF-2α upregulation or activation, and/or dysfunction in iron or lipid metabolism, which may be addressed by the induction of ferroptosis. Such disorder may include particular cancer types, such as clear cell renal cell carcinoma, breast cancer, liver cancer, pancreatic cancer and glioblastoma. The present disclosure also relates to the use of the compounds for the manufacture of medicaments useful for treating such disorders. The present disclosure further relates to pharmaceutical compositions including the novel compounds and to methods for the preparation of pharmaceutical compositions.

The present disclosure provides novel compounds that selectively inhibit HIF-2α translation by targeting the protein iron sulfur cluster assembly 2 (ISCA2). Without being bound to any particular theory, the inhibition of ISCA2 perturbs cellular iron homeostasis resulting in increased cellular iron content. This may result in the loss of the [4Fe-4S] cluster within IRP1, which promotes the functional switch in IRP1 from aconitase to IRE-binding, which inhibits translation of HIF-2α mRNA. Since HIF-2α production is reduced or abrogated, these novel compounds block both the transcriptional and non-transcriptional targets of HIF-2α. Additionally, the compounds interfere with cellular iron metabolism creating a situation of 'apparent' iron deprivation (given by elevated IRP2 and decreased FTH1) despite elevated iron levels within cells, which promotes iron-dependent cell death, or ferroptosis. The present disclosure provides compounds that are useful for preventing or treating HIF-2α associated disorders and/or disorders associated with iron or lipid accumulation, in which the induction of ferroptosis may be beneficial, especially in solid tumors such as CCRCC, breast cancer, liver cancer, pancreatic cancer and glioblastoma. The present disclosure demonstrates that these compounds efficiently decrease HIF-2a protein, and induce ferroptosis. Therefore, these compounds constitute a useful class of compounds that may be used in the treatment of HIF-2α/iron-associated disorders, including HIF-2a driven tumor types, and tumor types and disorders associated with iron or lipid accumulation.

Embodiments of the present disclosure comprises (or the invention, in one aspect, relates to) compounds of Formula I, or a pharmaceutically acceptable salt thereof.

Formula I

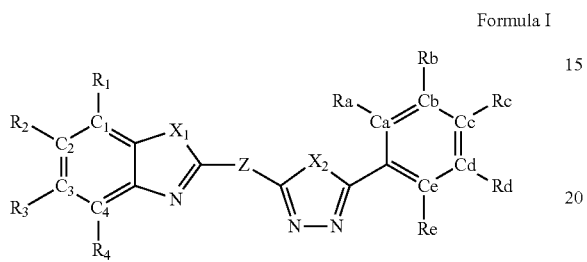

In some embodiments, each of $X_1$ and $X_2$ is independently O or S or NH.

In some embodiments, Z is C or O or S or $NR^4$, where $R^4$ is H or C1-4 alkyl.

In some embodiments, each of $C_1$, $C_2$, $C_3$, and $C_4$, ($C_{1-4}$) and each of Ca, Cb, Cc, Cd, and Ce (Ca-e) is independently C or N.

In some embodiments, each of $R_1$, $R_2$, $R_3$, and $R_4$, ($R_{1-4}$) and each of Ra, Rb, Rc, Rd, and Re (Ra-e) is independently selected from hydrogen, halo, CN, nitro, hydroxy, C1-6 alkyl, aryl, haloalkoxy, amino, C1-6 alkylamino, di-C1-4-alkylamino, carboxy, carbamyl, C1-6 alkylcarbamyl, di(C1-4 alkyl)carbamyl, C1-6 alkylcarbonyl, C1-6 alkoxycarbonyl, C1-6 alkylcarbonyloxy, C1-6 alkylsulfonyl, C1-6 alkylcarbonylamino, C1-6 alkylsulfonylamino, aminosulfonyl, C1-6 alkylaminosulfonyl, di-C1-4 alkylaminosulfonyl, aminosulfonylamino, C1-6 alkylaminosulfonylamino, di-C1-4 alkylaminosulfonylamino, and not present. In some embodiments, the hydroxy, C1-6 alkyl, aryl, haloalkoxy, amino, C1-6 alkylamino, di-C1-4-alkylamino, carboxy, carbamyl, C1-6 alkylcarbamyl, di(C1-4 alkyl)carbamyl, C1-6 alkylcarbonyl, C1-6 alkoxycarbonyl, C1-6 alkylcarbonyloxy, C1-6 alkylsulfonyl, C1-6 alkylcarbonylamino, C1-6 alkylsulfonylamino, aminosulfonyl, C1-6 alkylaminosulfonyl, di-C1-4 alkylaminosulfonyl, aminosulfonylamino, C1-6 alkylaminosulfonylamino, or di-C1-4 alkylaminosulfonylamino (of said $R_{1-4}$ or Ra-e) is optionally substituted with 1, 2, or 3 groups independently selected from halo, CN, hydroxy, C1-3, alkoxy, amino, C1-3 alkylamino, and di-C1-3-alkylamino.

In some embodiments, each of $R_{1-4}$ or Ra-e, independently, taken together with an adjacent one of $R_{1-4}$ or Ra-e, if any, and together with the $C_{1-4}$ or Ca-e to which said adjacent $R_{1-4}$ or Ra-e, if any, are respectively attached, optionally form a 3-7 membered carbocyclic or a 4-6 membered heterocyclic ring, each of which is optionally substituted with 1, 2, 3, or 4 C1-3 alkyl groups.

In some embodiments, $X_1$ is O or S or NH.
In some embodiments, $X_2$ is O.
In some embodiments, Z is NH.
In some embodiments, each of $C_1$, $C_2$, $C_3$, $C_4$, is independently C or N.

In some embodiments, Ca, Cc, Cd, and Ce are each C.
In some embodiments, Cb is C or N.
In some embodiments, $R_1$ is H, $CH_3$,

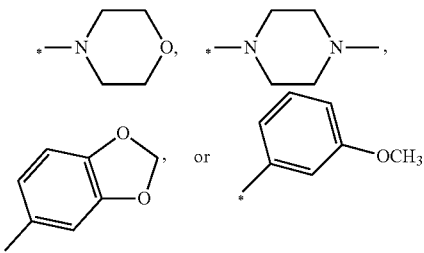

In some embodiments, $R_2$ is H, Cl, $CF_3$, $OCH_3$, or

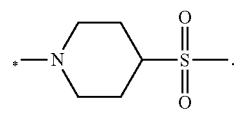 [SMILES: *N1CCC(S(C)(=O)=O)CC1]

In some embodiments, $R_3$ is H, $OCH_3$, $CF_3$,

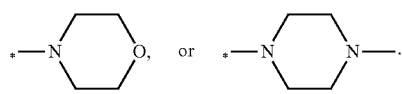

In some embodiments, $R_4$ is H, $OCH_3$, or

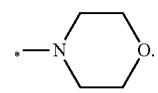

In some embodiments, Ra is H or $OCH_3$.
In some embodiments, Rb is H, F, not present, or $OCH_3$, or together with Rc forms a methylenedioxy.
In some embodiments, Rc is H, F, Cl, $CH_3$, $OCH_3$, CN, $OCF_3$, $SCH_3$, $N(CH_3)_2$,

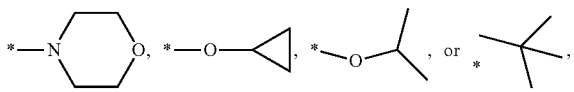

or together with Rb forms a methylenedioxy.
In some embodiments, Rd and Re are each independently H.
In some embodiments, $R_1$ is not H. In some embodiments, $R_2$ is not H. In some embodiments, $R_3$ is not H. In some embodiments, $R_4$ is not $OCH_3$. In some embodiments, Ra is not H. In some embodiments, Rb is not H. In some embodiments, Rc is not F. In some embodiments, Rd is not H. In some embodiments, Re is not H. In some embodiments, any permutations or combinations of the foregoing.

In some embodiments, the compound of Formula I is not 5-(4-fluorophenyl)-N-(4-methoxybenzo[d]thiazol-2-yl)-1,3,4-oxadiazol-2-amine.

In some embodiments, the compound (of Formula I) is (more specifically) a compound of Formula Ia, or a pharmaceutically acceptable salt thereof.

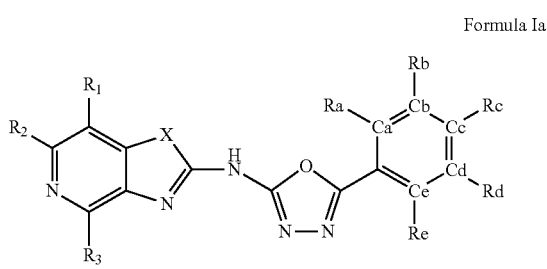

Formula Ia

In some embodiments, X is S, O, or NH.

In some embodiments, each of Ca, Cb, Cc, Cd, and Ce (Ca-e) is independently C or N.

In some embodiments, $R_1$ is H, $CH_3$,

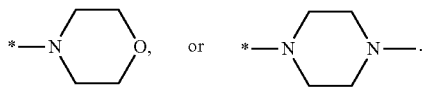

In some embodiments, $R_2$ is H, Cl, $CF_3$,

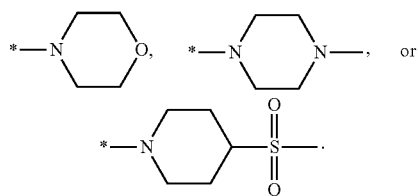

In some embodiments, $R_3$ is H, or $OCH_3$.

In some embodiments, each of Ra, Rb, Rc, Rd, and Re (Ra-e) is independently selected from H, F, OCH3,

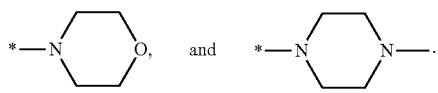

In some embodiments, the compound of Formula Ia is not 5-(4-fluorophenyl)-N-(4-methoxybenzo[d]thiazol-2-yl)-1,3,4-oxadiazol-2-amine.

In some embodiments, the compound (of Formula I or Ia) is (more specifically) a compound of Formula Ib, or a pharmaceutically acceptable salt thereof.

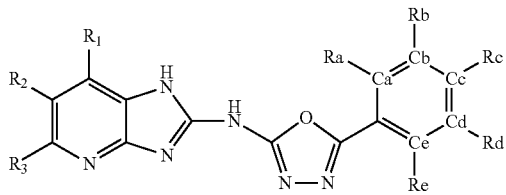

Formula Ib

In some embodiments, each of Ca, Cb, Cc, Cd, and Ce (Ca-e) is independently C or N.

In some embodiments, $R_1$ is H.

In some embodiments, $R_2$ is H.

In some embodiments, $R_3$ is H or $OCH_3$.

In some embodiments, each of Ra, Rb, Rc, Rd, and Re (Ra-e) is independently selected from H, F, $OCH_3$,

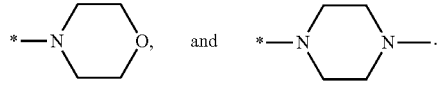

In some embodiments, the compound of Formula Ib is not 5-(4-fluorophenyl)-N-(4-methoxybenzo[d]thiazol-2-yl)-1,3,4-oxadiazol-2-amine.

In some embodiments, the compound (of Formula I, Ia, or Ib) is (more specifically) a compound of Formula Ic, or a pharmaceutically acceptable salt thereof.

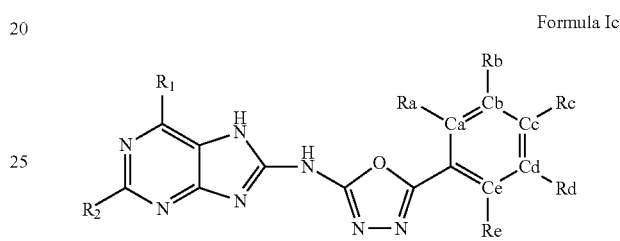

Formula Ic

In some embodiments, each of Ca, Cb, Cc, Cd, and Ce (Ca-e) is independently C or N.

In some embodiments, $R_1$ is H.

In some embodiments, $R_2$ is H or Cl.

In some embodiments, each of Ra, Rb, Rc, Rd, and Re (Ra-e) is independently selected from H, F, $OCH_3$,

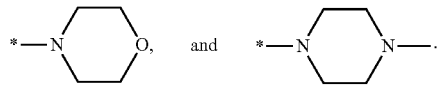

In some embodiments, the compound of Formula Ic is not 5-(4-fluorophenyl)-N-(4-methoxybenzo[d]thiazol-2-yl)-1,3,4-oxadiazol-2-amine.

Non-limiting examples or embodiments of the provided compounds include:

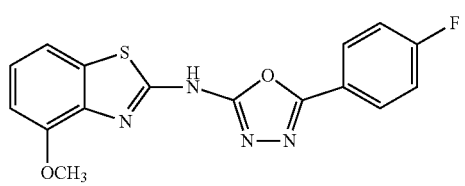

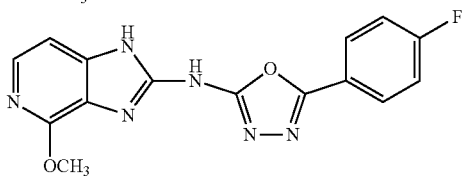

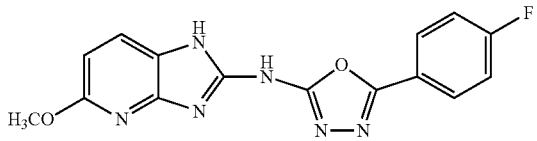

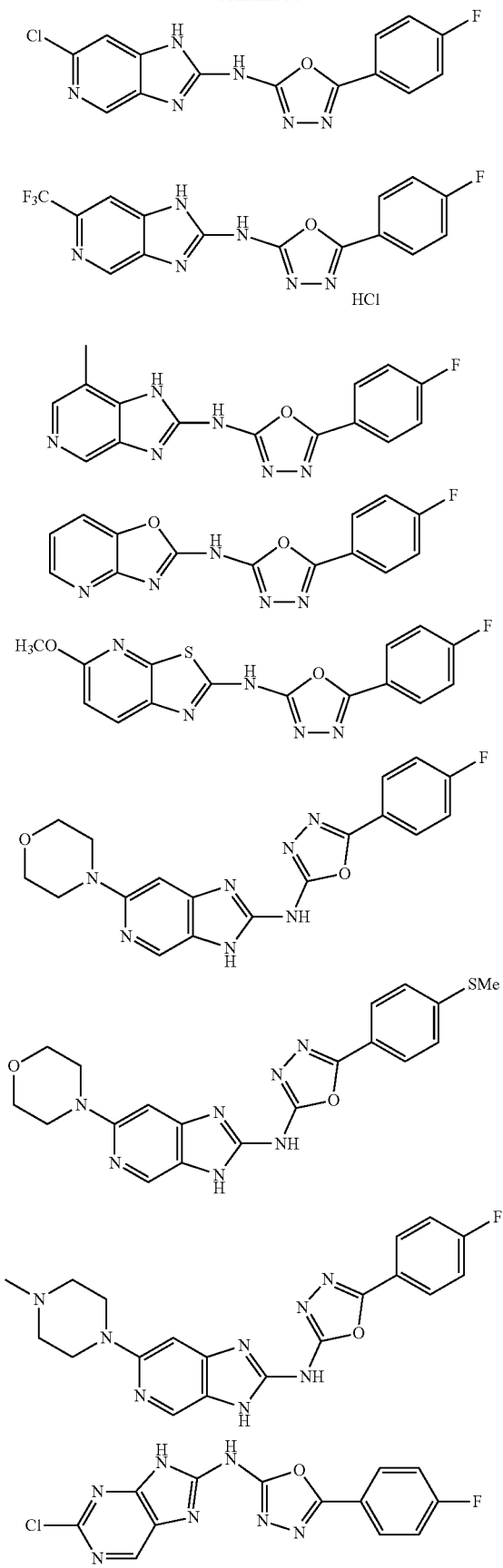
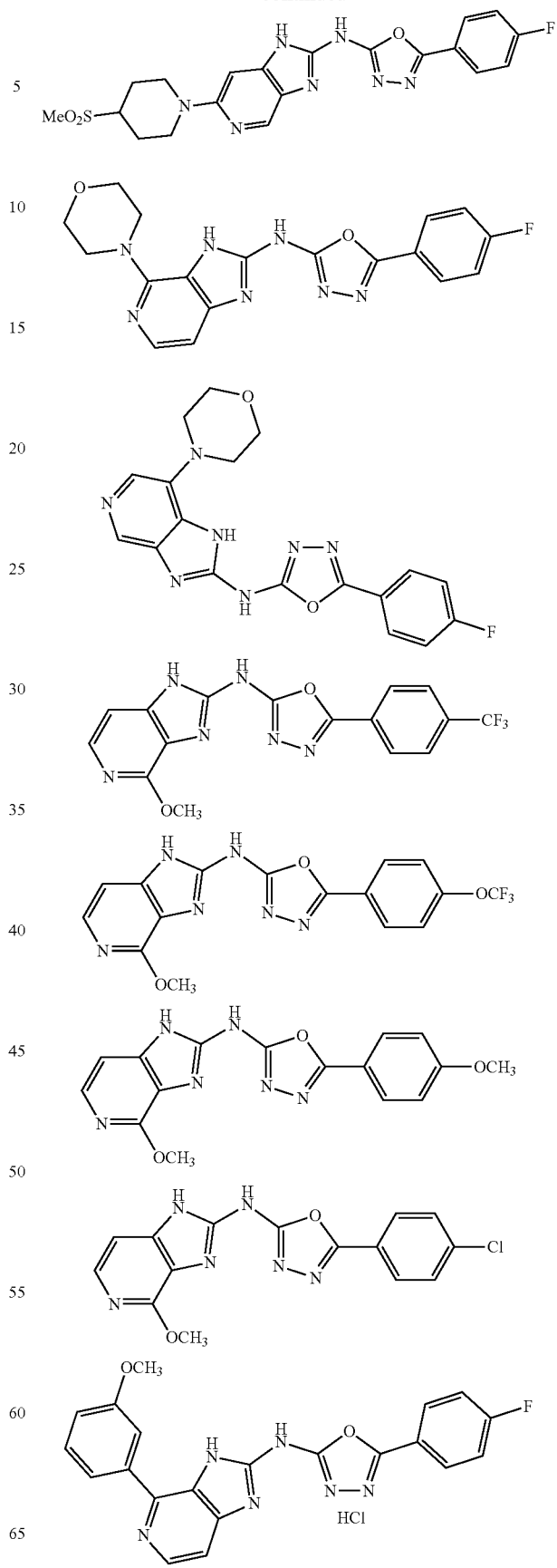

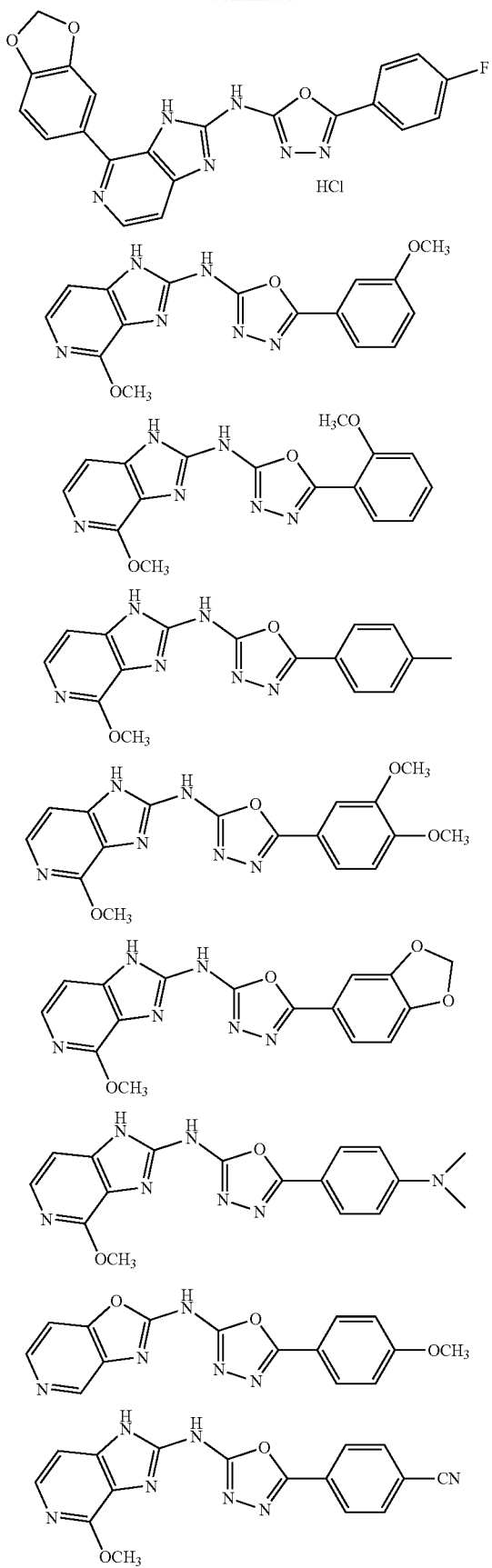
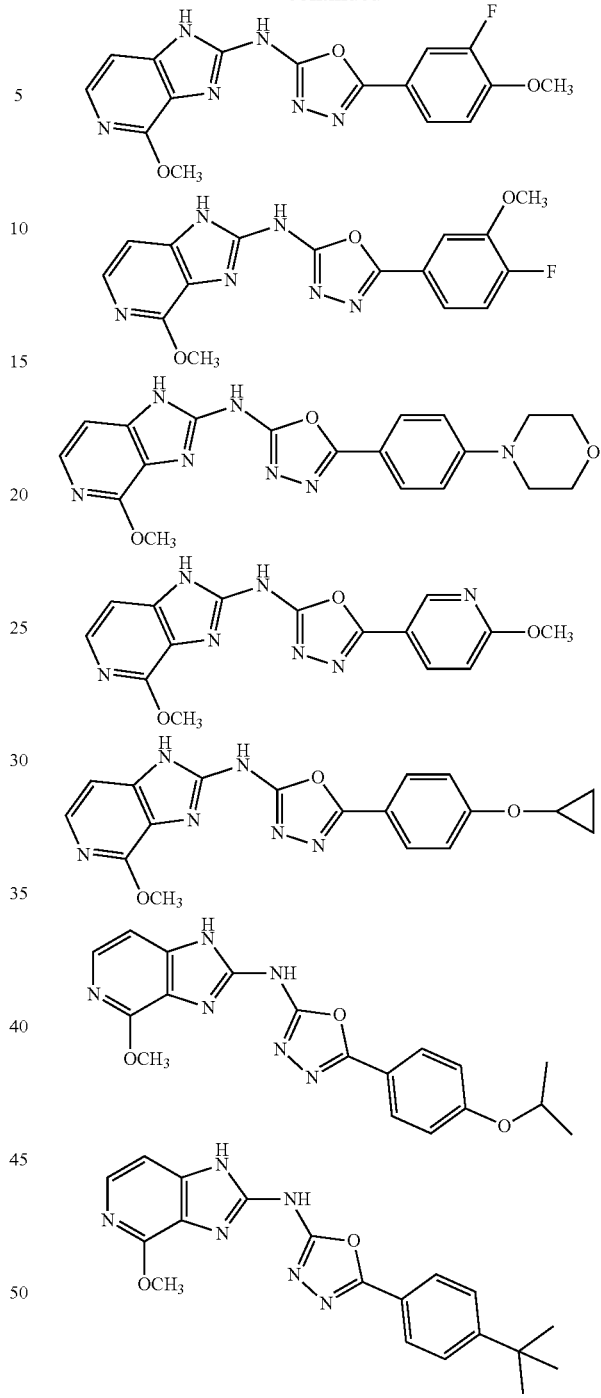
In some embodiments, the compound is not 5-(4-fluorophenyl)-N-(4-methoxybenzo[d]thiazol-2-yl)-1,3,4-oxadiazol-2-amine:
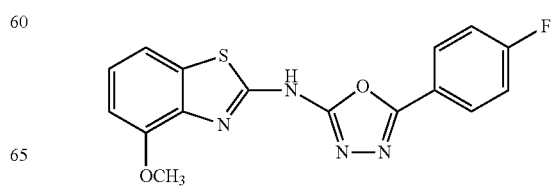

The compositions described herein also include, but are not limited to, hydrates, solvates, polymorphs, isomers, tautomers of the compounds, pharmaceutically acceptable salts of the compounds and pharmaceutically acceptable salts of the tautomers.

Embodiments include pharmaceutical formulations, medicaments including the compounds, methods of preparing pharmaceuticals formulations, medicaments, compounds, and methods of treating patients with the provided pharmaceutical formulations and compounds.

Also disclosed are pharmaceutical compositions comprising a therapeutically effective amount of a disclosed compound, with or without a pharmaceutically acceptable carrier.

Also disclosed are synthetic methods for making the disclosed compounds. Accordingly, embodiments of the present disclosure include methods of making a disclosed compound according to a disclosed scheme. In a further aspect, disclosed are the products of the disclosed synthetic methods.

Embodiments include methods of inhibiting HIF-2α activity and inducing ferroptosis. Such methods may comprise contacting HIF-2α and/or inducing ferroptosis with an effective amount of one or more of the compounds disclosed herein. By way of example, without limitation, HIF-2α may be contacted such that that one or more of the compounds binds to or interacts with HIF-2α, mRNA encoding HIF-2α, a gene encoding HIF-2α, or a protein that regulates the HIF-2a gene, protein or mRNA. Alternatively, one or more of the compounds may induce processes that result in ferroptosis and/or decreases in HIF-2α protein or mRNA, by contacting a component of the ISC complex, such as ISCA2.

Also disclosed are methods for the treatment of a disorder associated with a HIF-2α activity and/or iron dysfunction in a mammal comprising the step of administering to the mammal a therapeutically effective amount of one or more of the disclosed compounds, or a pharmaceutically acceptable salts, tautomers, isomers, hydrates, solvates, or polymorphs thereof.

Also disclosed are methods for inhibition of HIF-2α activity and the induction of ferroptosis in a mammal comprising the step of administering to the mammal a therapeutically effective amount of at least one disclosed compound, or a pharmaceutically acceptable salt, tautomer, isomer, hydrate, solvate, or polymorph thereof.

Also disclosed are methods for inhibiting HIF-2α activity and inducing ferroptosis in at least one cell, comprising the step of contacting the at least one cell with an effective amount of least one disclosed compound, or a pharmaceutically acceptable salt, tautomer, isomer, hydrate, solvate, or polymorph thereof.

Also disclosed are methods for treating a disorder associated with a HIF-2α activity and/or iron or lipid dysfunction in a mammal through eliciting an immune response in the mammal, comprising administering to the mammal a therapeutically effective amount of a disclosed compound, or a pharmaceutically acceptable salt, tautomer, isomer, hydrate, solvate, or polymorph thereof, wherein this compound causes an immune response beneficial in the treatment of the disorder associated with a HIF-2α and/or iron or lipid dysfunction. Such disorders may be, but are not limited to, any type of cancer or any disease caused by bacteria and/or viruses wherein HIF-2a activity and/or iron or lipid has been implicated.

Also disclosed are methods of inducing death of a cell through lipid peroxidation. The method can comprise administering to the cell one or more of the disclosed compounds.

Also disclosed are methods of inducing iron accumulation a cell. The method can comprise administering to the cell one or more of the disclosed compounds.

Also disclosed are pharmaceutical compositions comprising a pharmaceutically acceptable carrier and an effective amount of a disclosed compound, or a pharmaceutically acceptable salt, tautomer, isomer, hydrate, solvate, or polymorph thereof.

Also disclosed are kits comprising at least one disclosed compound, or a pharmaceutically acceptable salt, tautomer, isomer, hydrate, solvate, or polymorph thereof.

Also disclosed are methods for manufacturing a medicament comprising, combining at least one disclosed compound or at least one disclosed product with a pharmaceutically acceptable carrier or diluent. In a further aspect, the present disclosure relates to the use of a disclosed compound in the manufacture of a medicament for the treatment of a disorder associated with an HIF-2α activity dysfunction, and or lipid/iron dysregulation. In a further aspect, the present disclosure relates to the uses of disclosed compounds in the manufacture of a medicament for the treatment of a disorder of uncontrolled cellular proliferation.

Also disclosed are uses of a disclosed compound or a disclosed product in the manufacture of a medicament for the treatment of a disorder associated with a HIF-2α and/or iron or lipid dysfunction in a mammal.

While aspects of the present disclosure may be described and claimed in a particular statutory class, such as the system statutory class, this is for convenience only and one of skill in the art will understand that each aspect of the present disclosure may be described and claimed in any statutory class. Unless otherwise expressly stated, it is in no way intended that any method or aspect set forth herein be construed as requiring that its steps be performed in a specific order.

Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF FIGURES

The following figures form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
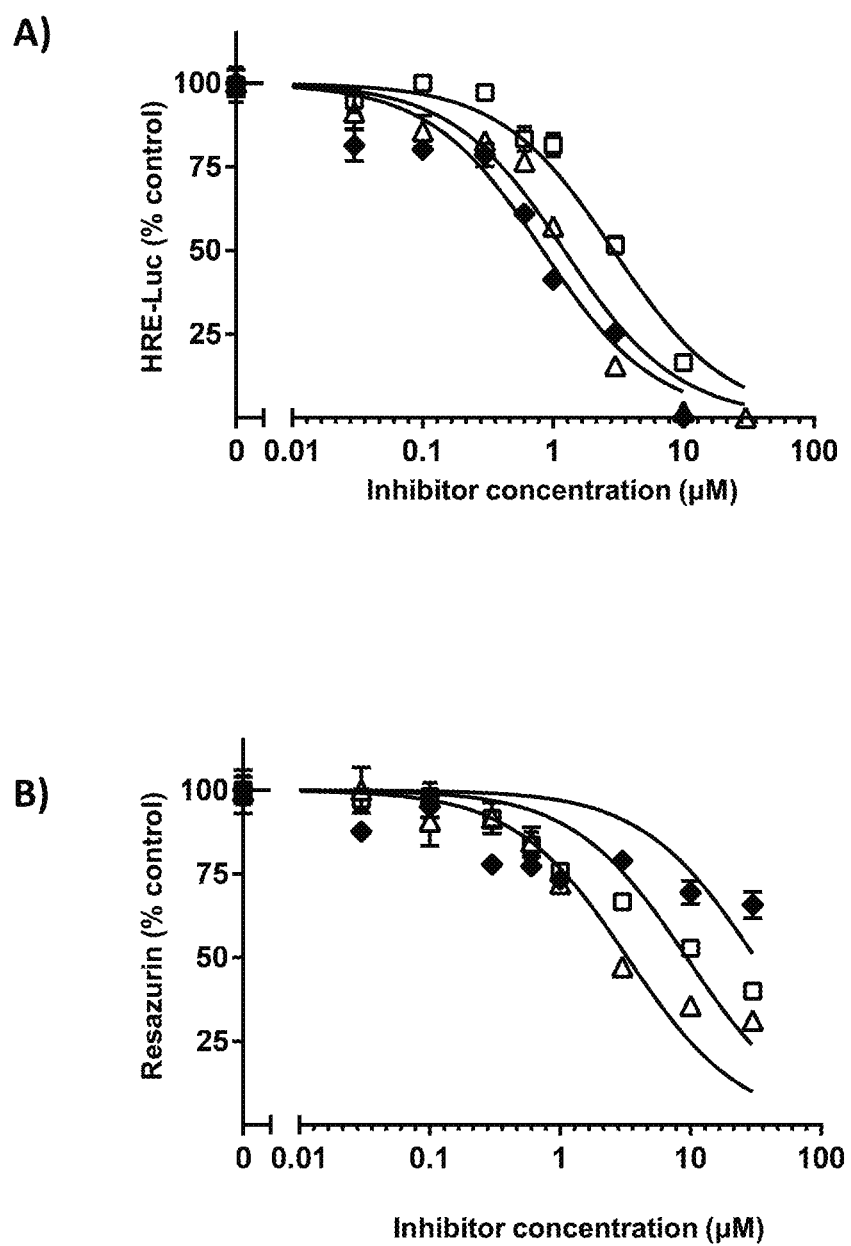
FIG. 1 shows the dose response curves for a select group of compounds KD002 (filled diamonds), KD007 (open squares) and KD021 (open triangles) using 786-0 CCRCC cells stably expressing a hypoxia-responsive element (HRE) fused to a luciferase reporter gene as a readout of HIF-2α transcriptional activity. Cells were treated with the indicated compounds for 24 hours. Part A shows normalized HRE-luciferase activity whereas Part B shows normalized resazurin (cell viability) readouts. Data points are average readings of quadruplicate wells with error bars indicating standard error of the mean (SEM).

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, devices, methods, and/or terminology.

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

The terms "comprising," "comprise," "comprises," and similar terms, as used herein, including in the claims, shall be inclusive and/or open-ended and do not exclude additional, un-recited elements or method steps, illustratively. Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, the transitional phrases "consisting of," "consist of," and similar terms shall be close-ended so as to exclude additional, un-recited elements or method steps, illustratively.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this disclosure is not intended to be interpreted to be equivalent to "comprising."

As used herein, the term "composition" includes products, formulations, and mixtures, as well as devices, apparatus, assemblies, kits, and so forth. Similarly, the term "method" includes processes, procedures, steps, and so forth. The terms "formulation" and "composition" may be used interchangeably herein, except where context clearly indicates otherwise.

As used herein, the term "method" also contemplates processes, procedures, steps, and so forth. Moreover, the term "products" also contemplates systems, compositions, kits, and so forth.

Various aspects of the present disclosure, including systems, methods, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the description thereof.

It is noted that embodiments of the present disclosure can comprise one or more combinations of two or more of the features described herein. As used herein, "feature(s)" and similar terms can include, for example, one or more compositions, ingredients, components, elements, members, parts, portions, systems, methods, steps, configurations, parameters, properties, or other aspect of the subject matter at hand. Embodiments can include any of the features, options, and/or possibilities set out elsewhere in the present disclosure, including in other aspects or embodiments of the present disclosure. It is also noted that while each of the foregoing, following, and/or other features described herein represents a distinct embodiment of the present disclosure, features can also be combined and/or combinable with another one or more other features in any suitable combination and/or order, with or without one or more additional features included therewith or performed therebetween, to form unique embodiments, each of which is contemplated in the present disclosure. Such combinations of any two or more of such features represent distinct embodiments of the present disclosure. Accordingly, the present disclosure is not limited to the specific combinations of exemplary embodiments described in detail herein and disclosure of certain features relative to a specific embodiment of the present disclosure should not be construed as limiting application or inclusion of said features to the specific embodiment.

In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. Likewise, any steps recited in any method described herein and/or recited in the claims can be executed in any suitable order and are not necessarily limited to the order described and/or recited, unless otherwise stated (explicitly or implicitly). Such steps can, however, also be required to be performed in a particular order in certain embodiments of the present disclosure.

As used throughout this application the words "can" and "may" are used in a permissive sense (i.e., meaning having the potential to), rather than the mandatory sense (i.e., meaning must).

The word "or" as used herein means any one member of a particular list and also includes any combination of members of that list.

As used in this specification and the appended claims, the singular forms "a," "an" and "the also contemplate plural referents, unless the context clearly dictates otherwise. Thus, for example, reference to a "layer" includes one, two, or more layers. Similarly, reference to a plurality of referents should be interpreted as comprising a single referent and/or a plurality of referents unless the content and/or context clearly dictate otherwise. Thus, reference to "layers" does not necessarily require a plurality of such layers. Instead, it will be appreciated that independent of conjugation; one or more layers are contemplated herein.

As used herein, nomenclature for compounds, including organic compounds, may be given using common names, IUPAC, IUBMB, or CAS recommendations for nomenclature. When one or more stereochemical features are present, Cahn-Ingold-Prelog rules for stereochemistry may be employed to designate stereochemical priority, E/Z specification, and the like. One of skill in the art may readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges may be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed (for example 10±10% or 10±5%). It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "HIF-2α" refers to hypoxia-inducible factor 2-alpha as is well known in the art. A non-limiting example of HIF-2α is encoded by the gene EPAS1. HIF-2α is a transcription factor that activates gene transcription in response to low oxygen or hypoxia. Homologs, paralogs, orthologs, etc. of HIF-2α, as well as the genes encoding these proteins, are well known in the art are easily searching in publicly available databases. Such additional homologues, paralogues, orthologues, etc. of HIF-2α, are to be considered as described herein.

As used herein, hypoxia is defined as an oxygen threshold below that required for the regular physiological function of a cell or tissue, typically defined as oxygen percentages of <5%.

As used herein, the term "IRP1" refers to iron-responsive element-binding protein 1 as is well known in the art. A nonlimiting example of IRP1 is encoded by the gene ACO1. Homologues, paralogues, orthologues, etc. of IRP1, as well as the genes encoding these proteins, are well known in the art are easily searching in publicly available databases. Such additional homologues, paralogues, orthologues, etc. of IRP1, are to be considered as described herein.

As used herein, the term "IRP2" refers to iron-responsive element-binding protein 2 as is well known in the art. A nonlimiting example of IRP2 is encoded by the gene IREB2. Homologues, paralogues, orthologues, etc. of IRP2, as well as the genes encoding these proteins, are well known in the art are easily searching in publicly available databases. Such additional homologues, paralogues, orthologues, etc. of IRP2, are to be considered as described herein.

As used herein, the term "FTH1" refers to ferritin heavy chain, or the heavy subunit of ferritin, the major intracellular iron storage protein in cells, as is well known in the art. Homologues, paralogues, orthologues, etc. of FTH1, as well as the genes encoding these proteins, are well known in the art are easily searching in publicly available databases. Such additional homologues, paralogues, orthologues, etc. of FTH1, are to be considered as described herein.

As used herein, the term "ISCA2" refers to iron sulfur cluster assembly 2, a mitochondrial protein involved in the synthesis of iron-sulfur clusters. ISCA2 interacts with the protein ISCA1, which refers to iron sulfur cluster assembly 1, and BA57, which refers to Iron-Sulfur Cluster Assembly Factor For Biotin Synthase- And Aconitase-Like protein, to participate in the mitochondrial iron-sulfur cluster assembly pathway. Homologues, paralogues, orthologues, etc. of ISCA1, ISCA2 and IBA57, as well as the genes encoding these proteins, are well known in the art are easily searching in publicly available databases. Such additional homologues, paralogues, orthologues are to be considered as described herein.

As used herein, the term "disrupt iron metabolism" refers to the ability to interfere with a cell's ability to sense, utilize, absorb, accumulate and/or otherwise traffic iron, whether in free form, or in complex with such carriers such as, by way of non-liming examples, transferrin, lipocalin, or ferritin.

As used herein, the term "ferroptosis" refers to a mechanism of controlled cell death that is morphologically, biochemically, and genetically distinct from apoptosis, various forms of necrosis, and autophagy. Ferroptosis is characterized by the overwhelming iron-dependent accumulation of lethal lipid-derived reactive oxygen species. The elevated levels of iron observed in many solid tumor types including CCRCC and breast cancer predispose these tumors to ferroptotic death. Other transition metals with oxidative capacity such as copper or zinc may also contribute to ferroptosis.

As used herein, the terms "optional" or "optionally" means that the subsequently described event or circumstance may or may not occur, and that the description includes instances where said event or circumstance occurs and instances where it does not.

As used herein, the term "subject" may be a vertebrate, such as a mammal, a fish, a bird, a reptile, or an amphibian. Thus, the subject of the herein disclosed methods may be, by way of non-limiting examples, a human, non-human primate, domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.). The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and non-human subjects. In some aspects of the disclosed methods, the subject has been diagnosed with a need for treatment of a disorder associated with HIF-2α and/or iron or lipid metabolism dysfunction prior to the administering step, including, but not limited to, disorders of uncontrolled cellular proliferation. In further aspects, the subject is determined by a person of skill, for example a physician, to likely derive benefit in mitigating or attenuating the manifestations or other negative impact of the disease or disorder associated with HIF-2α and/or iron or lipid metabolism dysfunction prior to the administering step, including, but not limited to, disorders of uncontrolled cellular proliferation.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that may be predisposed to the disease but has not yet been diagnosed as having it; (ii) inhibiting the disease, i.e., arresting its development; (iii) relieving the disease, i.e., causing regression of the disease; and (iv) reducing symptoms of the underlying disease, and/or that one or more of the underlying cellular, physiological, or biochemical causes or mechanisms causing the symptoms are reduced and/or eliminated. In one aspect, the subject is a mammal such as a primate, and, in a further aspect, the subject is a human.

As used herein, the term "prevent" or "preventing" refers to precluding, averting, obviating, forestalling, stopping, or hindering something from happening, especially by advance action. It is understood that where reduce, attenuate, inhibit or prevent are used herein, unless specifically indicated otherwise, the use of the other three words is also expressly disclosed.

As used herein, the term "diagnosed" means having been subjected to a physical examination by a person of skill, for example, a physician, and found to have a condition that may be diagnosed or treated by the compounds, compositions, or methods disclosed herein. For example, "diagnosed with a disorder of uncontrolled cellular proliferation" means having been subjected to a physical examination by a person of skill, by way of non-limiting example, a physician, and found to have a condition that may be diagnosed or treated by a compound or composition that inhibits HIF-2α and/or disrupts iron or lipid metabolism. As a further non-limiting example, "diagnosed with a need for inhibition of HIF-2α" refers to having been subjected to a physical examination by a person of skill, for example, a physician, and found to have a condition characterized by a HIF-2α and/or iron or lipid dysfunction. Such a diagnosis may be in reference to a disorder, such as a disorder of uncontrolled cellular proliferation, cancer and the like, as discussed herein. "Diagnosed with a need for treatment of one or more disorders of uncontrolled cellular proliferation associated with a HIF-2α and/or iron or lipid dysfunction" as used herein means having been subjected to a physical examination by a person of skill, for example, a physician, and found to have one or more disorders of uncontrolled cellular proliferation associated with a HIF-2α and/or iron or lipid dysfunction.

Further, "diagnosed with a need for inhibition of iron accumulation" refers to having been subjected to a physical examination by a person of skill, for example, a physician, and found to have a condition characterized by iron accumulation or iron metabolism dysfunction. Such a diagnosis may be in reference to a disorder, such as a disorder of uncontrolled cellular proliferation, cancer, hemochromatosis, and the like, as discussed herein. "Diagnosed with a need for treatment of one or more disorders of uncontrolled cellular proliferation associated with iron accumulation" as used herein means having been subjected to a physical examination by a person of skill, for example, a physician, and found to have one or more disorders of uncontrolled cellular proliferation associated with iron accumulation dysfunction.

Alternatively, the term "diagnosed" in the preceding examples may also mean to recognize or determine a disease or condition from its signs and/or symptoms, which may occur independently of a physical examination, and being found to likely derive benefit from diagnosis, treatment or other intervention.

As used herein, the phrase "identified to be in need of treatment for a disorder," or the like, refers to selection of a subject based upon need for treatment of the disorder, or the selection of a subject based on potential for benefit in mitigating or attenuating the negative effects of the disease or disorder For example, a subject may be identified as having a need for treatment of a disorder (e.g., a disorder related to a dysfunction of HIF-2α or a disorder associated with dysfunction in iron or lipid metabolism) based upon an earlier diagnosis or determination by a person of skill and thereafter subjected to treatment for the disorder. In this example, "need" also means "the potential to derive benefit in mitigating or attenuating the negative effects of the disease or disorder". It is contemplated that the identification may, in one aspect, be performed by a person different from the person making the diagnosis. It is also contemplated, in a further aspect, that the administration may be performed by one who subsequently performed the administration.

As used herein, "disorder associated with a HIF-2α activity dysfunction" or "disorder associated with iron or lipid metabolism dysfunction" is any disorder in which HIF-2α activity or iron or lipid metabolism is abnormal and/or outside the normal physiological range. By way of non-limiting example, HIF-2α activity may be greater than the normal expected activity in a cell, tissue, subject, or a sample from a subject. Similarly, levels of iron or lipids, or levels of proteins and tissues known to be associated with iron or lipids including but not limited to ferritin, transferrin, hematocrit, hemoglobin, IRP1 or IRP2, may be lower or higher than the normal physiological range in a cell, tissue, subject, or a sample from a subject. Examples of such disorders of HIF-2α and/or iron or lipid metabolism dysfunction include, but are not limited to, clear cell renal cell carcinoma (CCRCC), which is the most common and aggressive type of kidney cancer, liver cancer (hepatocellular carcinoma), pancreatic cancer, breast cancer, neuroblastoma, glioblastoma (GBM), non-small cell lung cancer, altitude sickness associated with elevated blood viscosity, and overabundance of EPO, and various hematological disorders. Determination of HIF-2a activity and/or iron or lipid metabolism being abnormal or outside the normal physiological range may be determined by comparison of said activity or levels to normal (undiseased) cells, tissues, subject, or a sample from a subject.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraoral administration, intracerebral administration, rectal administration, sublingual administration, buccal administration, intraurethral administration, and parenteral administration, including injectable such as intravenous administration, intra-arterial administration, intramuscular administration, and subcutaneous administration. Administration may be continuous or intermittent. In various aspects, a preparation may be administered therapeutically; that is, administered to treat an existing disease or condition. In further various aspects, a preparation may be administered prophylactically; that is, administered for prevention of a disease or condition.

The term "contacting" as used herein refers to bringing a disclosed compound and a cell, target receptor, or other biological entity together in such a manner that the compound affects the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms. A "therapeutically effective amount" may be insufficient to cause adverse side effects. The specific therapeutically effective dose level for any particular patient will depend upon a variety of factors including the disorder being treated, the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. The dosage may be adjusted by the individual physician in the event of any contraindications. Dosage may vary, and may be administered in one or more dose administrations daily, for one or several days. Guidance may be found in the literature for appropriate dosages for given classes of pharmaceutical products. In further various aspects, a preparation may be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ refers to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ refers to the concentration of a substance that is required for 50% inhibition in vivo or the inhibition is measured in vivo, as further defined elsewhere herein. Alternatively, $IC_{50}$ refers to the half maximal (50%) inhibitory concentration (IC) of a substance. The inhibition may be measured in a cell-line such as, but not limited to, 786-0, ACHN, RCC4, A498, Caki, HT29, AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG.

The term "pharmaceutically acceptable" describes a material that is not biologically or otherwise undesirable, i.e., does not cause an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Non-limiting examples of derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders. Such powders may be used for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. Isotonic agents such as sugars, sodium chloride and the like may also be included. Prolonged absorption of an injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release may be controlled. Depot injectable formulations may also be prepared by entrapping the drug in liposomes or microemulsions which are compatible with body tissues. Injectable formulations may be sterilized, for example, by filtration through a bacterial-retaining filter or by incorporating sterilizing agents in the form of sterile solid compositions which may be dissolved or dispersed in sterile water or other sterile injectable media just prior to use. Suitable inert carriers include, but are not limited to, sugars such as lactose. In certain embodiments, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, but are not limited to, those described below. The permissible substituents may be one or more and the same or different for appropriate organic compounds. As used herein, heteroatoms, such as nitrogen, may have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents may be further optionally substituted (i.e., further substituted or unsubstituted). Unless context clear indicates otherwise, the term "substituted," when used in connection with substituents, functional groups, or conjugates of (organic or inorganic) compounds does not generally connote a replacement (i.e., a substitution) of said substituents, functional groups, or conjugates.

In defining various terms, "$A^1$," "$A^2$," "$A^3$," and "$A^4$" and the like are used herein as generic symbols to represent various specific substituents. These symbols may be any substituent, not limited to those disclosed herein, and when they are defined to be certain substituents in one instance, they may, in another instance, be defined as some other substituent(s).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group may be cyclic or acyclic. The alkyl group may be branched or unbranched. The alkyl group may also be substituted or unsubstituted. By way of non-limiting example, the alkyl group may be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

By way of non-limiting example, a "C1-C3 alkyl" group may be selected from methyl, ethyl, n-propyl, i-propyl, and cyclopropyl, or from a subset thereof. In certain aspects, the "C1-C3 alkyl" group may be optionally further substituted. As a non-limiting example, a "C1-C4 alkyl" group may be selected from methyl, ethyl, n-propyl, i-propyl, cyclopropyl, n-butyl, i-butyl, s-butyl, 1-butyl, and cyclobutyl, or from a subset thereof. In certain aspects, the "C1-C4 alkyl" group may be optionally further substituted. As a further non-limiting example, a "C1-C6 alkyl" group may be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, in-hexyl, i-hexyl, 3-methylpentane, 2,3-dimethylbutane, neohexane, and cyclohexane, or from a subset thereof. In certain aspects, the "C1-C6 alkyl" group may be optionally further substituted. As a non-limiting example, a "C1-C8 alkyl" group may be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group may be optionally further substituted. As a non-limiting example, a "C1-C12 alkyl" group may be selected from methyl, ethyl, n-propyl, i-propyl, cyclopropyl, n-butyl, i-butyl, s-butyl, 1-butyl, cyclobutyl, n-pentyl, i-pentyl, s-pentyl, t-pentyl, neopentyl, cyclopentyl, in-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group may be optionally further substituted.

Throughout the specification, "alkyl" is generally used to refer to both unsubstituted alkyl groups and substituted alkyl groups; however, substituted alkyl groups are also specifically referred to herein by identifying the specific substituent(s) on the alkyl group. As a non-limiting example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties may, in addition, be specifically identified herein; for example, a particular substituted cycloalkyl may be referred to as, e.g., an "alkylcycloalkyl." Similarly, a substituted alkoxy may be specifically referred to as, e.g., a "halogenated alkoxy," a particular substituted alkenyl may be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group may be substituted or unsubstituted. The cycloalkyl group and heterocycloalkyl group may be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group may be substituted or unsubstituted. The aryl group may be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen may be selected from fluoro, chloro, bromo, and iodo. As a non-limiting example, halogen may be selected from fluoro, chloro, and bromo. As a further non-limiting example, halogen may be selected from fluoro and chloro. As a further non-limiting example, halogen may be selected from chloro and bromo. As a further non-limiting example, halogen may be selected from bromo and iodo. As a further non-limiting example, halogen may be selected from chloro, bromo, and iodo. In one aspect, halogen may be fluoro. In a further aspect, halogen may be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) may be used in place of halogens. For example, in certain aspects, halogen may be replaced by pseudohalogen. As a further non-limiting example, pseudohalogen may be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes, but is not limited to, azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH (or R—OH). Where indicated, a hydroxyl group (or "hydroxy" substituent) may be "substituted" or "optionally substituted," thereby forming, for example, an ether, represented by the formula R—O—R'.

"$R^1$," "$R^2$," "$R^3$," "$R^n$," where n is an integer, as used herein may, independently, possess one or more of the groups listed above. For example, if $R^1$ is a straight chain alkyl group, one of the hydrogen atoms of the alkyl group may optionally be substituted with a hydroxyl group, an alkoxy group, an alkyl group, a halide, and the like. Depending upon the groups that are selected, a first group may be incorporated within second group or, alternatively, the first group may be pendant (i.e., attached) to the second group. As a non-limiting example, with the phrase "an alkyl group comprising an amino group," the amino group may be incorporated within the backbone of the alkyl group. Alternatively, the amino group may be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents may be further optionally substituted (i.e., further substituted or unsubstituted).

Compounds described herein may contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein may contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures may be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer may also be referred to as an enantiomer, and a mixture of such isomers is often called an enantiomeric mixture. A 50:50 mixture of enantiomers is referred to as a racemic mixture.

Many of the compounds described herein may have one or more chiral centers and therefore may exist in different enantiomeric forms. If desired, a chiral carbon may be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon may be depicted as a wedge (bonds to atoms above the plane) and the other may be depicted as a series or wedge of short parallel lines is (bonds to atoms below the plane). The Cahn-Inglod-Prelog system may be used to assign the (R) or (S) configuration to a chiral carbon.

Compounds described herein comprise atoms in both their natural isotopic abundance and in non-natural abundance. The disclosed compounds may be isotopically-labelled or isotopically-substituted compounds identical to those described, but for the fact that one or more atoms are replaced by an atom having an atomic mass or mass number different from the atomic mass or mass number typically found in nature. Examples of isotopes that may be incorporated into compounds of the invention include, but are not limited to, isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{18}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, such as, by way of non-limiting example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes may be used for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be used. Isotopically labelled compounds of the present disclosure and prodrugs thereof may generally be prepared by carrying out the procedures below, by substituting a readily available isotopically labelled reagent for a non-isotopically labelled reagent.

The compounds described herein may be present as a solvate. In some cases, the solvent used to prepare the solvate is an aqueous solution, and the solvate is then often referred to as a hydrate. The compounds may be present as a hydrate, which may be obtained, by way of non-limiting example, by crystallization from a solvent or from aqueous solution. In this connection, one, two, three or any arbitrary number of solvate or water molecules may combine with the compounds according to the invention to form solvates and hydrates. Unless stated to the contrary, the compositions include all such possible solvates.

It is also appreciated that certain compounds described herein may be present as an equilibrium of tautomers. For example, ketones with an α-hydrogen may exist in an equilibrium of the keto form and the enol form.

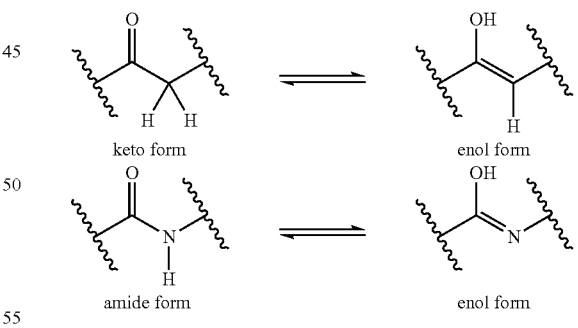

Likewise, amides with an N-hydrogen may exist in an equilibrium of the amide form and the imidic acid form. Unless stated to the contrary, the compounds described herein include all such possible tautomers.

It is known that chemical substances form solids which are present in different states of order which are termed polymorphic forms or modifications. The different modifications of a polymorphic substance may differ greatly in their physical properties. The compounds according described herein may be present in different polymorphic forms, with it being possible for particular modifications to be metastable. Unless stated to the contrary, the compounds include all such possible polymorphic forms.

In some aspects, a structure of a compound may be represented by a formula:

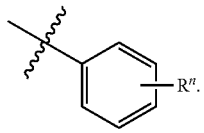

which is understood to be equivalent to a formula:

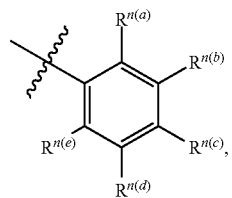

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent may be independently defined. For example, if in one instance $R^{n(a)}$ is halogen, then $R^{n(b)}$ is not necessarily halogen in that instance.

Certain materials, compounds, compositions, and components disclosed herein may be obtained commercially or readily synthesized using techniques generally known to those of skill in the art. By way of non-limiting example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); *March's Advanced Organic Chemistry*, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. By way of non-limiting example, if a particular compound is disclosed and discussed and a number of modifications that may be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, by way of non-limiting example, the sub-group of A-E, B-F, and C-E would be considered disclosed. This concept applies to all aspects of this application including, but not limited to, steps in methods of making and using the compositions of the invention. Thus, if there are a variety of additional steps that may be performed it is understood that each of these additional steps may be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that may perform the same function that are related to the disclosed structures, and that these structures will typically achieve the same result.

In one aspect, the present disclosure provides particular compounds. In certain aspects such compounds may be useful as inhibitors of HIF-2α. Moreover, in one aspect, the compounds are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with HIF-2α dysfunction, as further described herein. In additional aspects, provided are methods of treating a disorder of uncontrolled cellular proliferation, comprising administering to a subject a therapeutically effective amount of a compound of the invention.

In another aspect, the compounds are useful in the treatment of diseases of bacterial or viral origin. Accordingly, in one aspect, provided are methods of treating a disease caused by bacteria or viruses, comprising administering to a subject a therapeutically effective amount of a compound of the invention.

It is contemplated that each disclosed derivative may be optionally further substituted. It is also contemplated that any one or more derivatives may be optionally omitted from any claims. It is understood that a disclosed compound may be provided by the disclosed methods. It is also understood that the disclosed compounds may be employed in the disclosed methods of using or treating.

In one aspect, provided are the compounds of Formula I:

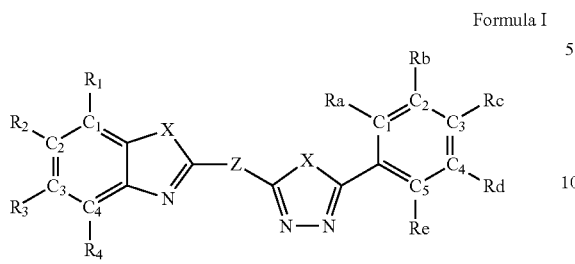

Formula I or a pharmaceutically acceptable salt thereof, wherein:
each X is independently O or S or NH;
each of $C_1$, $C_2$, $C_3$, $C_4$, $C_5$ is independently C or N;
Z is C or O or S or $NR^4$;
$R^4$ is H or C1-4 alkyl;
R1, R2, R3, R4, Ra, Rb, Rc, Rd, Re are each independently selected from hydrogen, halo, CN, nitro, hydroxy, C1-6 alkyl, haloalkoxy, amino, C1-6 alkylamino, di-C1-4-alkylamino, carboxy, carbamyl, C1-6 alkylcarbamyl, di(C1-4alkyl)carbamyl, C1-6 alkylcarbonyl, C1-6 alkoxycarbonyl, C1-6 alkylcarbonyloxy, C1-6 alkylsulfonyl, C1-6 alkylcarbonylamino, C1-6 alkylsulfonylamino, aminosulfonyl, C1-6 alkylaminosulfonyl, di-C1-4 alkylaminosulfonyl, aminosulfonylamino, C1-6 alkylaminosulfonylamino, di-C1-4 alkylaminosulfonylamino, and not present (i.e., nothing); wherein said C1-6 alkyl, C-haloalkyl, C1-6 alkoxy, C-haloalkoxy, C1-6 alkylamino, di-C1-4-alkylamino, C1-6 alkylcarbamyl, di(C1-4 alkyl)carbamyl, and C1-6 alkylcarbonyl are each optionally substituted with 1, 2, or 3 groups independently selected from halo, CN, hydroxy, C1-3 alkoxy, amino, C1-3 alkylamino, and di-C1-3-alkylamino;
any two adjacent Ra-e may be taken together with the atoms to which they are attached to form a 3-7 membered carbocyclic or 4-6 membered heterocyclic ring, each of which is optionally substituted with 1, 2, 3, or 4 C1-3 alkyl groups.

In some embodiments, the compound is a compound of Formula Ia:

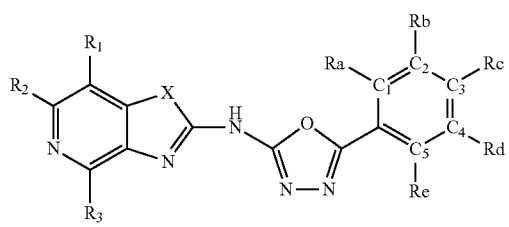

Formula Ia or a pharmaceutically acceptable salt thereof; wherein
X is independently S, O, or NH;
each of $C_1$, $C_2$, $C_3$, $C_4$, $C_5$ is independently C or N;
$R_1$ is H, CH3,

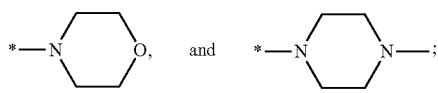

$R_2$ is H, Cl, CF3, and

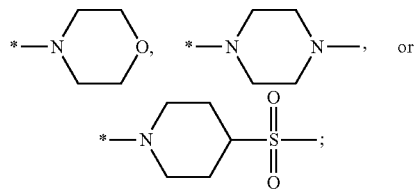

$R_3$ is H, or OCH3.
Each of Ra, Rb, Rc, Rd, Re is independently one of H, F, OCH3, or

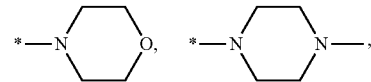

or not present.

In some embodiments, the compound is a compound of Formula Ib:

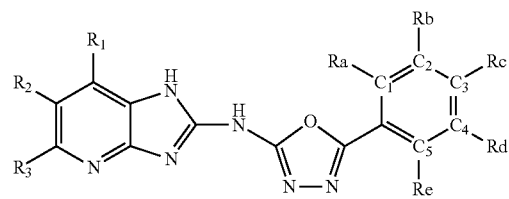

Formula Ib or a pharmaceutically acceptable salt thereof; wherein
each of $C_1$, $C_2$, $C_3$, $C_4$, $C_5$ is independently C or N;
$R_1$ is H;
$R_2$ is H;
$R_3$ is H, or OCH3; and
each Ra, Rb, Rc, Rd, Re is independently one of H, F, OCH3,

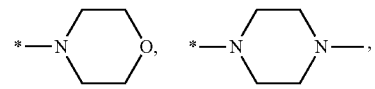

or not present.

In some embodiments, the compound is a compound of Formula Ic:

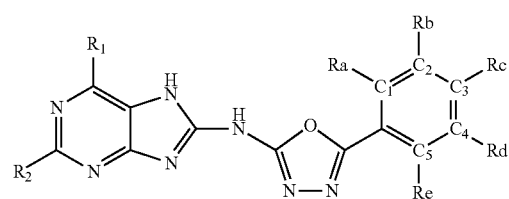

Formula Ic or a pharmaceutically acceptable salt thereof; wherein
$R_1$ is H; and
$R_2$ is H, Cl;
each of $C_1$, $C_2$, $C_3$, $C_4$, $C_5$ is independently C or N; and
each of Ra, Rb, Rc, Rd, Re is independently H, F, OCH3,

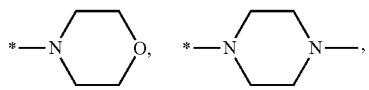

or not present.

In certain embodiments of Formula I (or corresponding Formulas Ia, Ib, or Ic), $R_1$ is not H. In some embodiments, $R_2$ s not H, In some embodiments, $R_3$ is not H. In some embodiments, $R_4$ is not $OCH_3$. In some embodiments, Ra is not H. In some embodiments, Rb is not H. In some embodiments, Rc is not F. In some embodiments, Rd is not H. In some embodiments, Re is not H. In some embodiments, any permutations or combinations of the foregoing.

Embodiments of the present disclosure comprises (or the invention, in one aspect, relates to) compounds of Formula I, or a pharmaceutically acceptable salt thereof.

Formula I

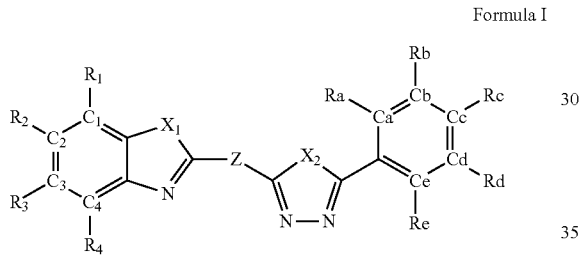

In some embodiments, each of $X_1$ and $X_2$ is independently O or S or NH.

In some embodiments, Z is C or O or S or $NR^A$, where $R^A$ is H or C1-4 alkyl.

In some embodiments, each of $C_1$, $C_2$, $C_3$, and $C_4$, ($C_{1-4}$) and each of Ca, Cb, Cc, Cd, and Ce (Ca-e) is independently C or N.

In some embodiments, each of $R_1$, $R_2$, $R_3$, and $R_4$, ($R_{1-4}$) and each of Ra, Rb, Rc, Rd, and Re (Ra-e) is independently selected from hydrogen, halo, CN, nitro, hydroxy, C1-6 alkyl, aryl, haloalkoxy, amino, C1-6 alkylamino, di-C1-4-alkylamino, carboxy, carbamyl, C1-6 alkylcarbamyl, di(C1-4 alkyl)carbamyl, C1-6 alkylcarbonyl, C1-6 alkoxycarbonyl, C1-6 alkylcarbonyloxy, C1-6 alkylsulfonyl, C1-6 alkylcarbonylamino, C1-6 alkylsulfonylamino, aminosulfonyl, C1-6 alkylaminosulfonyl, di-C1-4 alkylaminosulfonyl, aminosulfonylamino, C1-6 alkylaminosulfonylamino, di-C1-4 alkylaminosulfonylamino, and not present (i.e., nothing). In some embodiments, the C1-6 alkyl, aryl, haloalkoxy, amino, C1-6 alkylamino, di-C1-4-alkylamino, carboxy, carbamyl, C1-6 alkylcarbamyl, di(C1-4 alkyl)carbamyl, C1-6 alkylcarbonyl, C1-6 alkoxycarbonyl, C1-6 alkylcarbonyloxy, C1-6 alkylsulfonyl, C1-6 alkylcarbonylamino, C1-6 alkylsulfonylamino, aminosulfonyl, C1-6 alkylaminosulfonyl, di-C1-4 alkylaminosulfonyl, aminosulfonylamino, C1-6 alkylaminosulfonylamino, or di-C1-4 alkylaminosulfonylamino (of said $R_{1-4}$ or Ra-e) is optionally substituted with 1, 2, or 3 groups independently selected from halo, CN, hydroxy, C1-3, alkoxy, amino, C1-3 alkylamino, and di-C1-3-alkylamino.

In some embodiments, each of $R_{1-4}$ or Ra-e, independently, taken together with an adjacent one of $R_{1-4}$ or Ra-e, if any, and together with the $C_{1-4}$ or Ca-e to which said adjacent $R_{1-4}$ or Ra-e, if any, are respectively attached, optionally form a 3-7 membered carbocyclic or a 4-6 membered heterocyclic ring, each of which is optionally substituted with 1, 2, 3, or 4 C1-3 alkyl groups.

In some embodiments, $X_1$ is O or S or NH.
In some embodiments, $X_2$ is O.
In some embodiments, Z is NH.
In some embodiments, each of $C_1$, $C_2$, $C_3$, C4, is independently C or N.
In some embodiments, Ca, Cc, Cd, and Ce are each C.
In some embodiments, Cb is C or N.
In some embodiments, $R_1$ is H, $CH_3$,

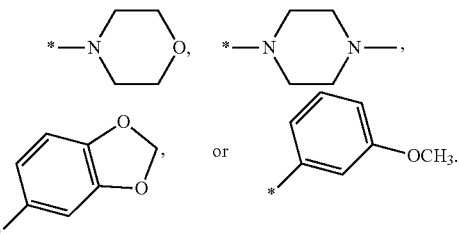

In some embodiments, $R_2$ is H, Cl, $CF_3$, $OCH_3$, or

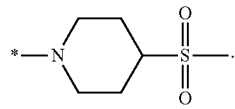 [SMILES: *N1CCC(S(C)(=O)=O)CC1]

In some embodiments, $R_3$ is H, $OCH_3$, $CF_3$,

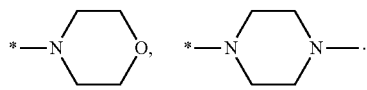

In some embodiments, $R_4$ is H, $OCH_3$, or

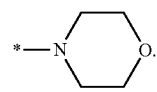 [SMILES: *N1CCOCC1]

In some embodiments, Ra is H or $OCH_3$.
In some embodiments, Rb is H, F, not present, or $OCH_3$, or together with Rc forms a methylenedioxy.
In some embodiments, Rc is H, F, Cl, $CH_3$, $OCH_3$, CN, $OCF_3$, $SCH_3$, $N(CH_3)_2$,

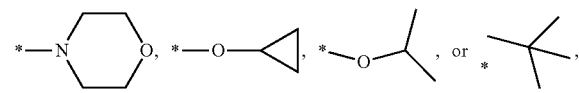

or together with Rb forms a methylenedioxy.
In some embodiments, Rd and Re are each independently H.
In some embodiments, $R_1$ is not H. In some embodiments, $R_2$ is not H. In some embodiments, $R_3$ is not H. In some embodiments, $R_4$ is not $OCH_3$. In some embodiments, Ra is not H. In some embodiments, Rb is not H. In some embodiments, Rc is not F. In some embodiments, Rd is not H. In some embodiments, Re is not H. In some embodiments, any permutations or combinations of the foregoing.

In some embodiments, the compound of Formula I is not 5-(4-fluorophenyl)-N-(4-methoxybenzo[d]thiazol-2-yl)-1,3,4-oxadiazol-2-amine.

In some embodiments, the compound (of Formula I) is (more specifically) a compound of Formula Ia, or a pharmaceutically acceptable salt thereof.

Formula Ia

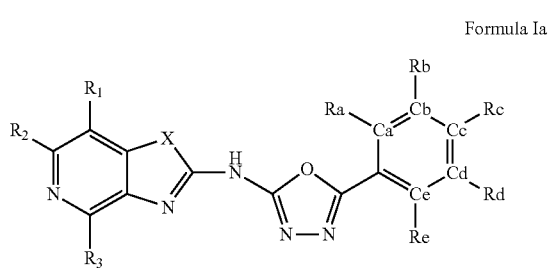

In some embodiments, X is S, O, or NH.

In some embodiments, each of Ca, Cb, Cc, Cd, and Ce (Ca-e) is independently C or N.

In some embodiments, $R_1$ is H, $CH_3$,

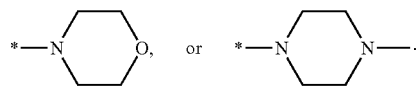

In some embodiments, $R_2$ is H, Cl, $CF_3$,

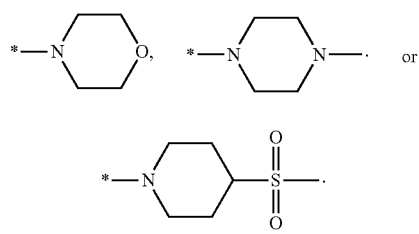

In some embodiments, $R_3$ is H, or $OCH_3$.

In some embodiments, each of Ra, Rb, Rc, Rd, and Re (Ra-e) is independently selected from H, F, OCH3,

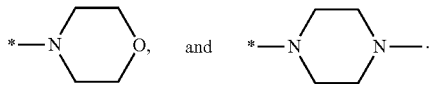

In some embodiments, the compound of Formula Ia is not 5-(4-fluorophenyl)-N-(4-methoxybenzo[d]thiazol-2-yl)-1,3,4-oxadiazol-2-amine.

In some embodiments, the compound (of Formula I or Ia) is (more specifically) a compound of Formula Ib, or a pharmaceutically acceptable salt thereof.

Formula Ib

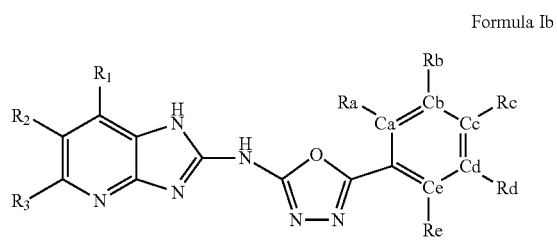

In some embodiments, each of Ca, Cb, Cc, Cd, and Ce (Ca-e) is independently C or N.

In some embodiments, $R_1$ is H.

In some embodiments, $R_2$ is H.

In some embodiments, $R_3$ is H or $OCH_3$.

In some embodiments, each of Ra, Rb, Rc, Rd, and Re (Ra-e) is independently selected from H, F, $OCH_3$,

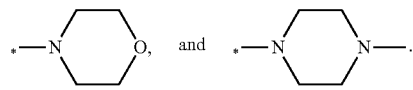

In some embodiments, the compound of Formula Ib is not 5-(4-fluorophenyl)-N-(4-methoxybenzo[d]thiazol-2-yl)-1,3,4-oxadiazol-2-amine.

In some embodiments, the compound (of Formula I, Ia, or Ib) is (more specifically) a compound of Formula Ic, or a pharmaceutically acceptable salt thereof.

Formula Ic

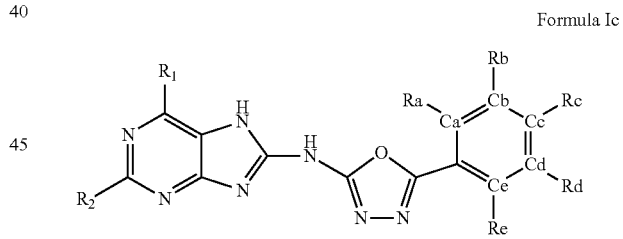

In some embodiments, each of Ca, Cb, Cc, Cd, and Ce (Ca-e) is independently C or N.

In some embodiments, $R_1$ is H.

In some embodiments, $R_2$ is H or Cl.

In some embodiments, each of Ra, Rb, Rc, Rd, and Re (Ra-e) is independently selected from H, F, $OCH_3$,

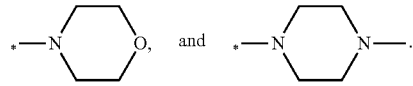

In some embodiments, the compound of Formula Ic is not 5-(4-fluorophenyl)-N-(4-methoxybenzo[d]thiazol-2-yl)-1,3,4-oxadiazol-2-amine.

Non-limiting examples or embodiments of the provided compounds include:
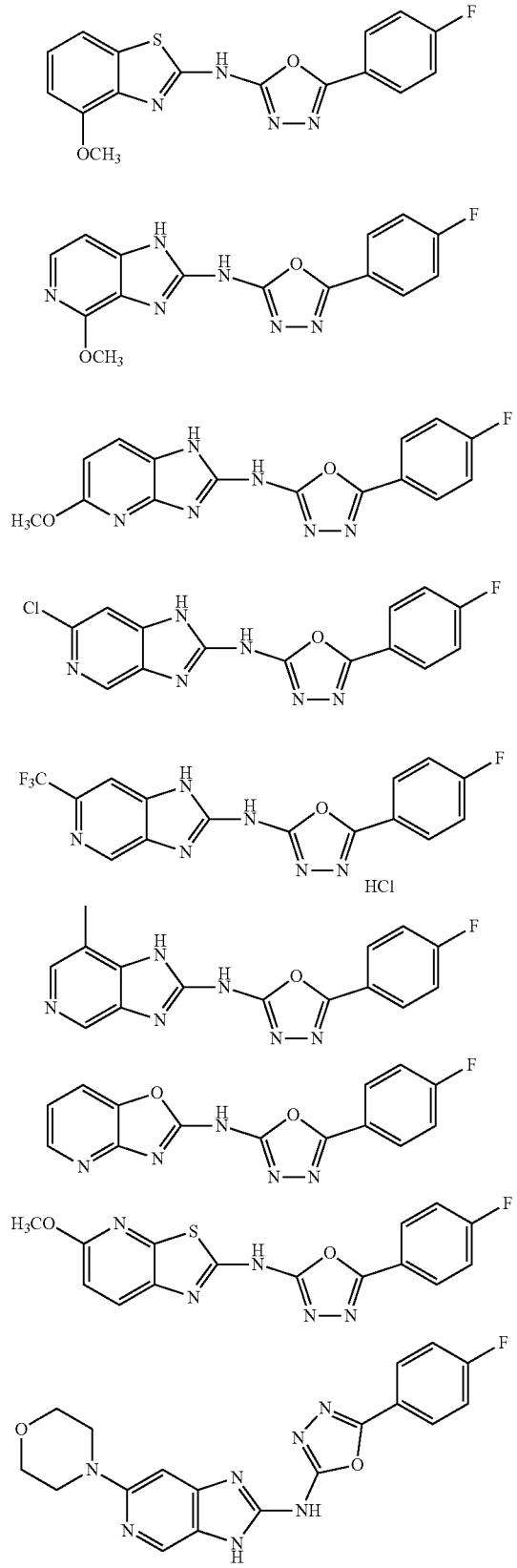
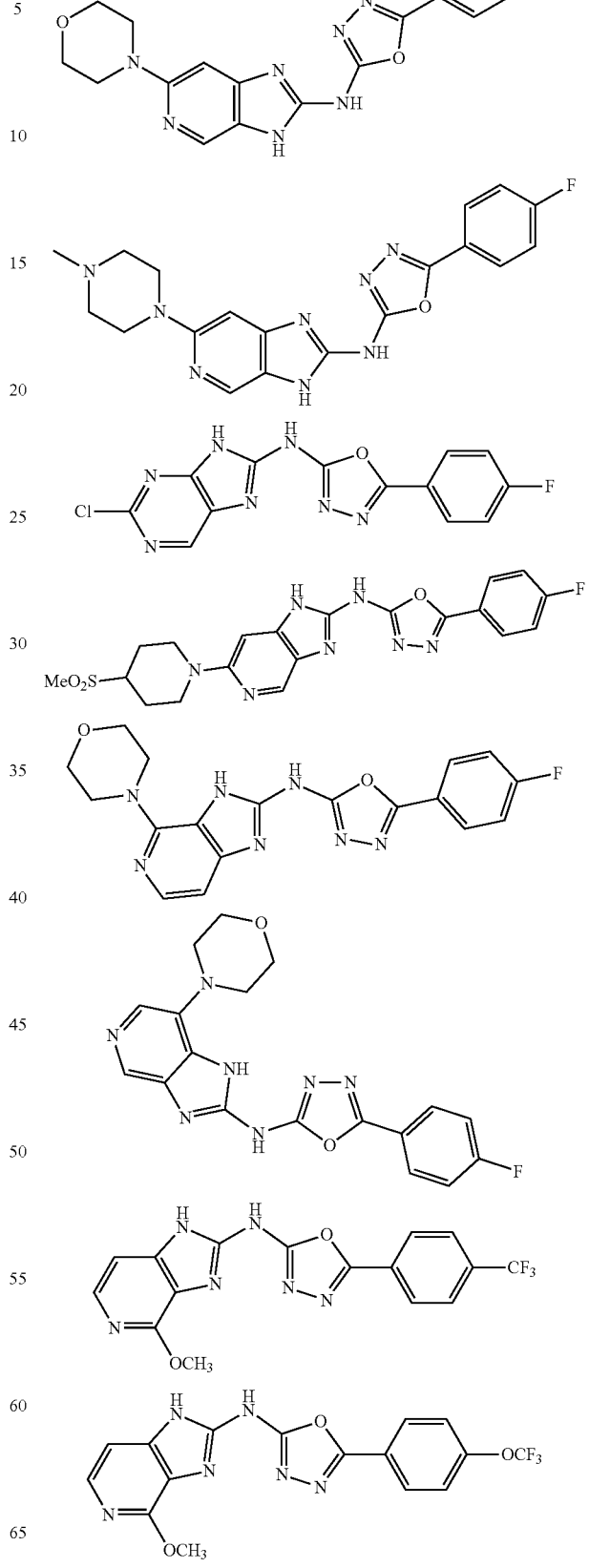

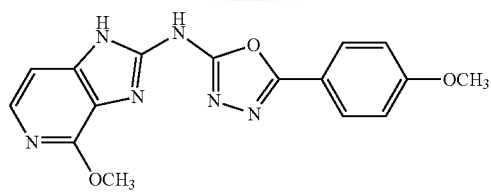
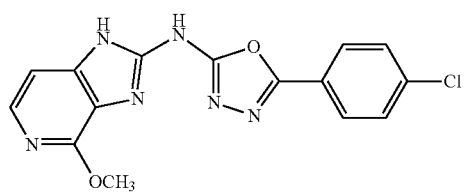
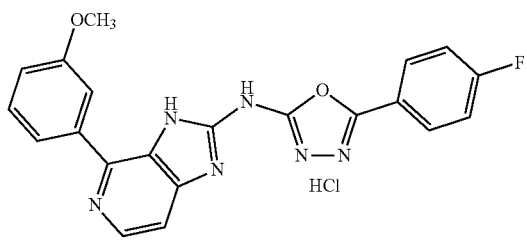
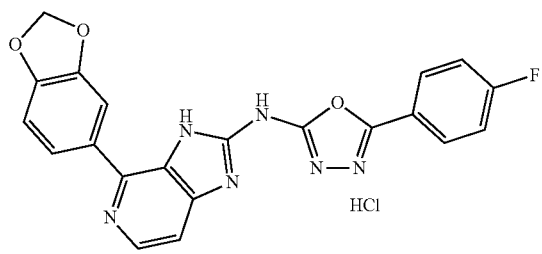
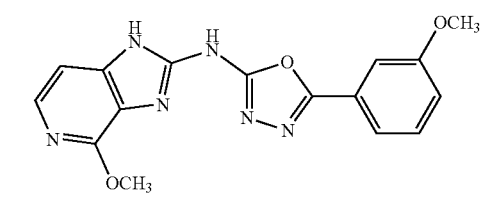
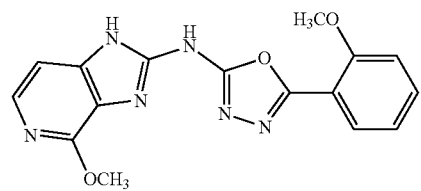
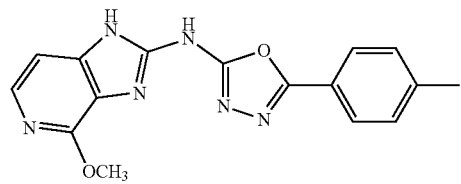
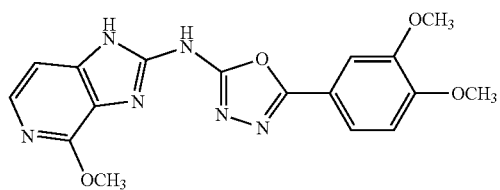
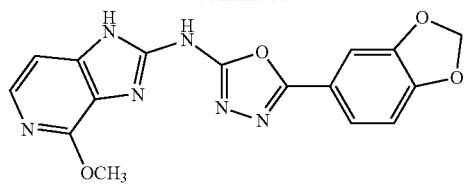
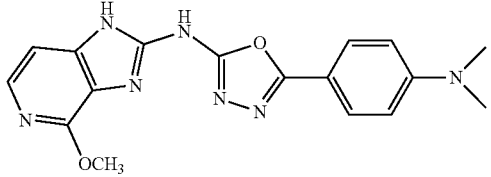
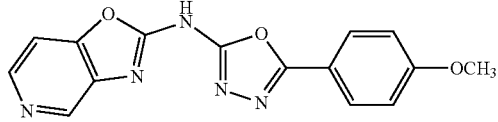
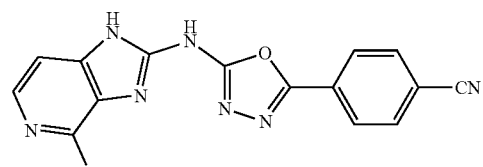
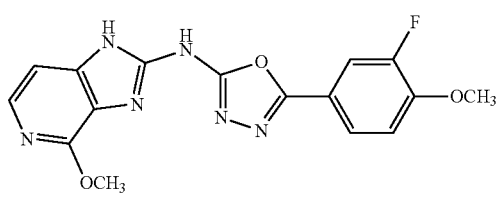
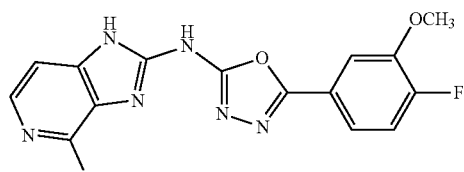
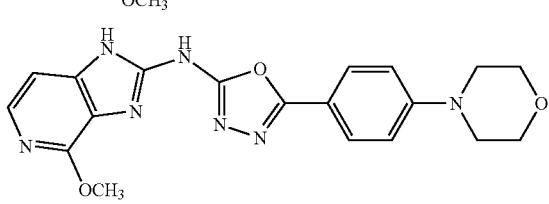
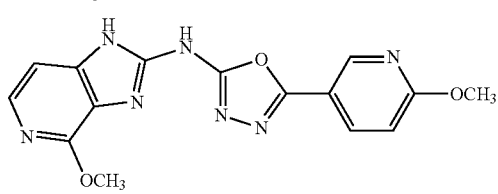
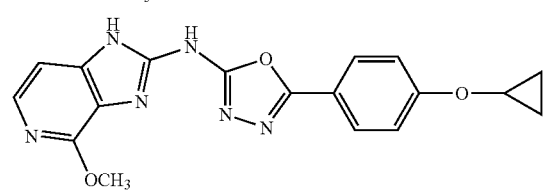

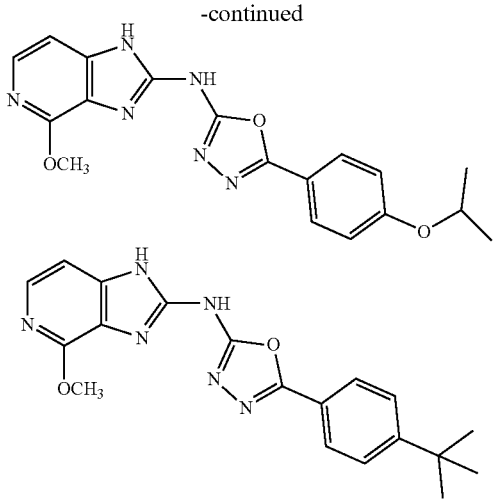

In certain embodiments, the compounds is not 5-(4-fluorophenyl)-N-(4-methoxybenzo[d]thiazol-2-yl)-1,3,4-oxadiazol-2-amine:

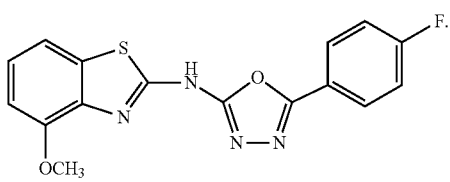 [SMILES: COc1cccc2sc(Nc3nnc(-c4ccc(F)cc4)o3)nc12]

Also provided are pharmaceutical compositions comprising a therapeutically effective amount of any of the compounds described herein and a pharmaceutically acceptable carrier.

Further embodiments provide methods of the treatment of a disorder of uncontrolled cellular proliferation in a mammal, the method comprising the step of administering to the mammal an effective amount of any of the compounds described herein.

Additional embodiments include methods of decreasing HIF-2 a activity. In particular embodiments, the method comprises the step of administering to a subject an effective amount of any of the compounds described herein.

Still further embodiments include methods of inhibiting HIF-2α activity. In particular embodiments, the method comprises the step of administering to a subject an effective amount of any of the compounds of the invention.

In one aspect, provided are methods of making compounds useful as inhibitors of HIF-2a such as the compounds disclosed herein. In a further aspect, the products of disclosed methods of making are modulators of HIF-2α activity.

Reactions used to generate the compounds described herein may be prepared by employing reactions as shown in the following Reaction Schemes, in addition to other standard manipulations known in the literature or to one skilled in the art. The following examples are provided so that the invention might be more fully understood, are illustrative only, and should not be construed as limiting. For clarity, examples having a single substituent are shown where multiple substituents are allowed under the definitions disclosed herein.

In one aspect, the disclosed compounds comprise the products of the synthetic methods described herein. In a further aspect, the disclosed compounds comprise a compound produced by a synthetic method described herein. In a still further aspect, the described are pharmaceutical compositions comprising a therapeutically effective amount of the product of the disclosed methods and a pharmaceutically acceptable carrier. In a still further aspect, provided are methods for manufacturing a medicament comprising combining at least one compound of any of disclosed compounds or at least one product of the disclosed methods with a pharmaceutically acceptable carrier or diluent.

Where reaction conditions and amounts of ingredients are not stated, it is believed that it is within a skill in the art to determine them. It is contemplated that each disclosed method may further comprise additional steps, manipulations, and/or components. It is also contemplated that any one or more step, manipulation, and/or component may be optionally omitted. It is understood that a disclosed method may be used to provide the disclosed compounds. It is also understood that the products of the disclosed methods may be employed in the disclosed methods of using.

In a further aspect, provided are pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise one or more of the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular subject, and nature and severity of the conditions for which the active ingredient is being administered. The pharmaceutical compositions may be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When a compound described herein is acidic, its corresponding salt may be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts may be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

In practice, the compounds described herein, or pharmaceutically acceptable salts thereof, may be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions may be presented as discrete units suitable for oral administration such as capsules, cachets or tablets each containing a predetermined amount of the active ingredient. Further, the compositions may be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds described herein, and/or pharmaceutically acceptable salt(s) thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product may then be conveniently shaped into the desired presentation.

Thus, the pharmaceutical compositions of the present disclosure may include a pharmaceutically acceptable carrier and a compound or a pharmaceutically acceptable salt of the compounds of the invention. The compounds described herein, or pharmaceutically acceptable salts thereof, may also be included in pharmaceutical compositions in combination with one or more other therapeutically active compounds.

The pharmaceutical carrier employed may be, for example, a solid, liquid, or gas. Examples of solid carriers include, but are not limited to, lactose, terra alba, sucrose, talc, gelatin, agar, pectin, acacia, magnesium stearate, and stearic acid. Examples of liquid carriers include, but are not limited to, sugar syrup, peanut oil, olive oil, and water. Examples of gaseous carriers include, but are not limited to, carbon dioxide and nitrogen.

In preparing the compositions for oral dosage form, any convenient pharmaceutical media may be employed. By way of non-limiting example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the compositions described herein may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The pharmaceutical compositions described herein may comprise a compound as described herein (or pharmaceutically acceptable salts thereof) as an active ingredient, a pharmaceutically acceptable carrier, and optionally one or more additional therapeutic agents or adjuvants. The instant compositions include, but are not limited to, compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Pharmaceutical compositions including the compounds described herein may be suitable for parenteral administration may be prepared as solutions or suspensions of the active compounds in water. A suitable surfactant may be included such as, for example, hydroxypropylcellulose. Dispersions may also be prepared in glycerol, liquid polyethylene glycols, and mixtures thereof in oils. Further, a preservative may be included to prevent the detrimental growth of microorganisms.

Pharmaceutical compositions including the compounds described herein may suitable for injectable use include sterile aqueous solutions or dispersions. Furthermore, the compositions may be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier may be a solvent or dispersion medium containing, for example, water, ethanol, polyol (e.g., glycerol, propylene glycol and liquid polyethylene glycol), vegetable oils, and suitable mixtures thereof.

Pharmaceutical compositions including the compounds described herein may be in a form suitable for topical use such as, for example, an aerosol, cream, ointment, lotion, dusting powder, mouth washes, gargles, and the like. Further, the compositions may be in a form suitable for use in transdermal devices. These formulations may be prepared, utilizing a compound of the invention, or pharmaceutically acceptable salts thereof, via conventional processing methods. As a non-limiting example, a cream or ointment is prepared by mixing hydrophilic material and water, together with about 5 wt % to about 10 wt % of the compound, to produce a cream or ointment having a desired consistency.

Pharmaceutical compositions including the compounds described herein may be in a form suitable for rectal administration wherein the carrier is a solid. In certain embodiments, the pharmaceutical composition forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants may be included to render the formulation isotonic with the blood of the intended recipient. Compositions containing a compound described herein, and/or pharmaceutically acceptable salts thereof, may also be prepared in powder or liquid concentrate form.

In the treatment conditions which require inhibition or negative modulation of HIF-2α protein activity an appropriate dosage level will generally be about 0.01 to 500 mg per kg patient body weight per day and may be administered in single or multiple doses. By way of non-limiting examples, the dosage level may be about 0.1 to about 250 mg/kg per day; or 0.5 to 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5.0 or 5.0 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the subject to be treated. The compound may be administered on a regimen of 1 to 4 times per day, preferably once or twice per day. This dosing regimen may be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Further provided are methods for the manufacture of a medicament for inhibiting or negatively modulating HIF-2α protein activity and for inducing ferroptosis (e.g., treatment of a disorder of uncontrolled cellular proliferation, or one or more neurodegenerative disorders associated with HIF-2α dysfunction and/or iron or lipid accumulation) in subjects (e.g., humans) comprising combining one or more disclosed compounds, products, or compositions with a pharmaceutically acceptable carrier or diluent. Thus, in one aspect, the present disclosure provides for manufacturing a medicament comprising combining at least one disclosed compound or at least one disclosed product with a pharmaceutically acceptable carrier or diluent.

The disclosed pharmaceutical compositions may further comprise other therapeutically active compounds, which are usually applied in the treatment of the above mentioned pathological conditions.

It is understood that the disclosed compositions may be prepared from the disclosed compounds. It is also understood that the disclosed compositions may be employed in the disclosed methods of using.

The disclosed compounds may be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) may be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy may also be administered on overlapping schedules. It is also envisioned that the combination of one or more active ingredients and a disclosed compound will be more efficacious than either as a single agent.

The pharmaceutical compositions and methods of the present invention may further comprise other therapeutically active compounds as noted herein which are usually applied in the treatment of the above mentioned pathological conditions.

The compounds disclosed herein are useful for treating, preventing, ameliorating, controlling or reducing the risk of a variety of disorders wherein the patient or subject would benefit from inhibition or negative modulation of HIF-2α or from the induction of ferroptosis. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which HIF-2α inhibition or ferroptosis induction is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

Provided herein is the use of described chemical compositions to treat diseases or disorders in patients (e.g. human) wherein HIF-2α inhibition or ferroptosis induction would be predicted to have a therapeutic effect, such as disorders of uncontrolled cellular proliferation (e.g. cancers) and neurodegenerative disorders such as Alzheimer's disease, Huntington's disease, and Parkinson's disease, and/or diseases caused by bacteria and/or viruses, by administering one or more disclosed compounds or products.

The compounds described herein may also be used for immunotherapy. In one embodiment, the disclosed compounds treat disorders of uncontrolled cellular proliferation, and/or diseases caused by bacteria and/or viruses through immunotherapy, meaning that the compounds elicit immunotherapeutic response which results in the treatment of these diseases.

The compounds disclosed herein are useful for treating, preventing, ameliorating, controlling or reducing the risk of a variety of disorders of uncontrolled cellular proliferation.

Also provided is a method of use of a disclosed compound, composition, or medicament. In one aspect, the method of use is directed to the treatment of a disorder. In a further aspect, the disclosed compounds may be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) may be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy may also be administered on overlapping schedules. It is also envisioned that the combination of one or more active ingredients and a disclosed compound may be more efficacious than either as a single agent.

Examples of disorders treatable with the provided compounds include a disorder of uncontrolled cellular proliferation. In a yet further aspect, the disorder of uncontrolled cellular proliferation is cancer. In a yet further aspect, the cancer is a leukemia. In an even further aspect, the cancer is a sarcoma. In a still further aspect, the cancer is a solid tumor. In a yet further aspect, the cancer is a lymphoma. In certain embodiments, disclosed herein are compounds for use in the treatment of HIF-deregulated diseases with an inflammatory component, such as cancers, stroke, and rheumatoid arthritis.

It is understood that cancer refers to or describes the physiological condition in mammals that is typically characterized by unregulated cell growth. The cancer may be multi-drug resistant (MDR) or drug-sensitive. Examples of cancer include, but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In a further aspect, the cancer is a cancer of the brain. In a still further aspect, the cancer of the brain is selected from a glioma, medulloblastoma, primitive neuroectodemal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer may be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In certain embodiments, disclosed herein are compounds for use in the treatment of HIF-deregulated cardiovascular diseases such as cardiac arrhythmia and heart failure.

In certain embodiments, disclosed herein are compounds for use in the treatment of preventing or reducing resistance to radiotherapy and chemotherapy.

In certain embodiments, disclosed herein are compounds for use in the prevention or reduction of tumor invasion and tumor metastasis.

In certain embodiments, disclosed herein are compounds for use in the prevention or reduction of angiogenesis and disorders related to angiogenesis.

In certain embodiments, disclosed herein are compounds for use in the treatment of HIF-deregulated hematological diseases especially polycythemia such as Chuvash polycythemia.

In various aspects, disorders associated with HIF-2α dysfunction and/or iron or lipid dysfunction include neurodegenerative disorders. In a further aspect, the neurodegenerative disease is selected from Alzheimer's disease, Parkinson's disease, and Huntington's disease.

The compounds are further useful in a method for the prevention, treatment, control, amelioration, or reduction of risk of the diseases, disorders and conditions noted herein. The compounds are further useful in methods for the prevention, treatment, control, amelioration, or reduction of risk of the aforementioned diseases, disorders and conditions in combination with other agents.

Further aspects are directed to administration of a HIF-2α inhibitor and ferroptosis inducer for improving treatment outcomes in the context of disorders of uncontrolled cellular proliferation, including cancer. That is, in one aspect, the methods relate to a co-therapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy may be continuous or intermittent. Administration need not be simultaneous with therapy and may be before, during, and/or after therapy. For example, cancer therapy may be provided within 1, 2, 3, 4, 5, 6, 7 days before or after administration of the compound. As a further example, cancer therapy may be provided within 1, 2, 3, or 4 weeks before or after administration of the compound. As a still further example, cognitive or behavioral therapy may be provided before or after administration within a period of time of 1, 2, 3, 4, 5, 6, 7, 8, 9, or 10 half-lives of the administered compound.

In one aspect, the disclosed compounds may be used in combination with one or more other drugs in the treatment, prevention, control, amelioration, or reduction of risk of diseases or conditions for which disclosed compounds or the other drugs may have utility, where the combination of the drugs together are safer or more effective than either drug alone. Such other drug(s) may be administered, by a route and in an amount commonly used therefor, contemporaneously or sequentially with a compound of the present invention. When a described compound is used contemporaneously with one or more other drugs, a pharmaceutical composition in unit dosage form containing such other drugs and a disclosed compound may be used. However, the combination therapy may also include therapies in which a disclosed compound and one or more other drugs are administered on different overlapping schedules. It is also contemplated that when used in combination with one or more other active ingredients, the disclosed compounds and the other active ingredients may be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a disclosed is used contemporaneously with one or more other drugs, a pharmaceutical composition containing such other drugs in addition to a disclosed compound may be created and/or used. Accordingly, the pharmaceutical compositions include those that also contain one or more other active ingredients, in addition to a compound of the present invention.

The weight ratio of a disclosed compound to the second active ingredient may be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations or one or more disclosed compounds and other active ingredients will generally also be within the aforementioned range, but in each case, an effective dose of each active ingredient should be used.

In such combinations, a disclosed compound and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

The term "co-administration" and similar terms refer to concurrent, sequential, and/or combined administration of two or more components. For instance, two components can be co-administered by administering each component in a combined dosage. Alternatively, or in addition, two components can be co-administered by administering each component in separate dosages, concurrently, simultaneously, or sequentially (e.g., distinct administrations separated by a period of time). The period of time can be very small (e.g., substantially, immediately following a first administration) or longer (e.g., 1-60 seconds, 1-60 minutes, 1-24 hours, 1-7 days, 1-4 weeks, 1-12 months, and so forth, or any value or range of values there between). Concurrent or simultaneous administration can include overlapping administration time frames for the two or more components or administration of a combination product comprising a mixture of the two or more components.

In one aspect, the compound may be employed in combination with anti-cancer therapeutic agents or other known therapeutic agents.

In the treatment of conditions which require inhibition or negative modulation of HIF2α and induction of feroptosis, an appropriate dosage level will generally be about 0.01 to 1000 mg per kg patient body weight per day which may be administered in single or multiple doses. In non-limiting examples, the dosage level may be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, provided are methods for inhibiting or negatively modulating HIF-2a and inducing ferroptosis in at least one cell, comprising the step of contacting the at least one cell with at least one described compound, in an amount effective to modulate or activate HIF2α activity response and ferroptosis, e.g. in the at least one cell. In a further aspect, the cell is mammalian (e.g. human). In a further aspect, the cell has been isolated from a subject prior to the contacting step. In a further aspect, contacting is via administration to a subject.

In one aspect, provided are methods for the treatment of a disorder of uncontrolled cellular proliferation in a mammal, the methods comprising the step of administering to the mammal an effective amount of least one disclosed compound or a product of a disclosed method of making a compound, or a pharmaceutically acceptable salt, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

EXAMPLES

The following examples are set forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the disclosed are illustrated. Starting materials and the requisite intermediates are in some cases commercially available, or may be prepared according to literature procedures or as illustrated herein.

The following exemplary compounds of the invention were synthesized. The exemplary compounds are typically depicted in free base form, according to the IUPAC naming convention. However, some of the exemplary compounds were obtained or isolated in salt form.

Some of the exemplary compounds were obtained as racemic mixtures of one or more enantiomers or diastereomers. The compounds may be separated by one skilled in the art to isolate individual enantiomers. Separation may be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds may also be separated directly by chromatographic methods using chiral stationary phases.

Example 1

Synthesis Schemes, Methods and Procedures

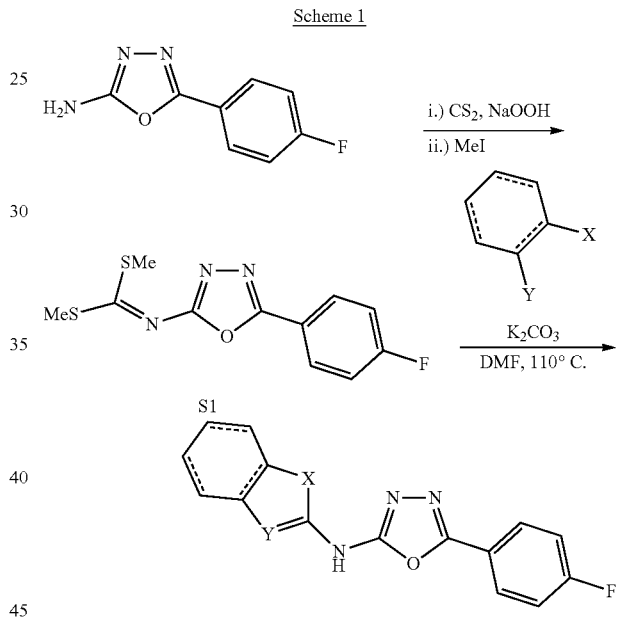

Dimethyl (5-(4-fluorophenyl)-1,3,4-oxadiazol-2-yl) carbonimidodithioate (S1)

To a flame-dried, 100 mL round bottom flask equipped with a magnetic stir bar was added 5-(4-fluorophenyl)-1,3,4-oxadiazol-2-amine (1.00 g, 5.58 mmol) and DMF (10 mL). The reaction was cooled to 0° C., and aqueous NaOH (20 M, 0.31 mL) was added dropwise. Upon complete addition, the reaction was allowed to stir for 10 minutes followed by dropwise addition of $CS_2$ (0.62 mL). The resulting solution was allowed to warm to room temperature over a period of 30 minutes. The flask was again cooled to 0° C., and iodomethane (1.6 g) was added dropwise. Upon addition, a yellow precipitate formed. The reaction was allowed to proceed for 30 minutes, and completion was confirmed by LC-MS. The reaction contents were then poured an Erlenmeyer flask with 50 mL of $H_2O$, and the resulting precipitate was collected by vacuum filtration. The yellow precipitate was recrystallized from hot MeOH (70 mL) to yield off-white crystals (0.83 g), which were used without further purification. ¹H NMR (500 MHz, DMSO-d₆) δ 8.02 (dd, 2H), 7.41 (t, 2H), 2.66 (s, 6H). LCMS [M+H] 284.2.

As used herein, "room temperature" may refer to any temperature above freezing (0° C., or other (equivalent) freezing temperature, depending on the presence of freezing point adjusting components) and below normal human body temperature (37° C., or other (equivalent) boiling temperature, depending on the presence of boiling point adjusting components), preferably above about 4° C. and below about 35° C., more preferably between about 5° C. and about 32° C., between about 8° C. and about 30° C., between about 10° C. and about 30° C., between about 10° C. and about 25° C., between about 10° C. and about 20° C., between about 10° C. and about 15° C., between about 15° C. and about 30° C., between about 15° C. and about 25° C., between about 15° C. and about 20° C., between about 20° C. and about 30° C., between about 20° C. and about 25° C., between about 20° C. and about 22° C., or any value or range of values therebetween.

KD-001

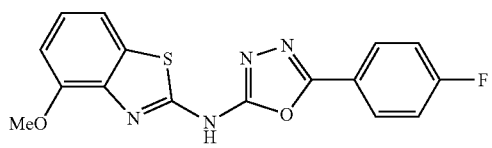

5-(4-fluorophenyl)-N-(4-methoxybenzo[d]thiazol-2-yl)-1,3,4-oxadiazol-2-amine (KD-001)

To an oven-dried, 40 mL vial with a magnetic stir bar was added 5-(4-fluorophenyl)-1,3,4-oxadiazol-2-amine (0.1 g, 0.35 mmol), 2-amino-3-methoxybenzenethiol hydrochloride (0.075 g, 0.39 mmol), K₂CO₃ (0.107 g, 0.77 mmol) and DMF (3 mL). The reaction was flushed with nitrogen, sealed, placed in a heating block at 120° C. and stirred overnight (16h). The reaction was cooled to rt and solvent reduced to ~1 mL. Cold water (25 mL) was added and neutralized to ~pH 7 with the addition of 1N HCl. The solid was collected and washed with water. Recrystallization from MeOH/Acetone followed by HPLC purification (C18 0-90% 0.1% TFA in water/0.1% TFA in CH₃CN, 254 nM) afforded the TFA salt upon removal of the solvent. Addition of 1 mL of 2.0 M HCl in MeOH and removal of solvent afforded 5-(4-fluorophenyl)-N-(4-methoxybenzo[d]thiazol-2-yl)-1,3,4-oxadiazol-2-amine hydrochloride salt. ¹H NMR (400 MHz, DMSO-d₆) δ 7.90 (t, 2H), 7.36 (t, 12H), 7.22 (d, 1H), 6.89 (t, 1H), 6.77 (d, 1H), 3.87 (s, 3H). LCMS [M+H] 343.1.

KD-002

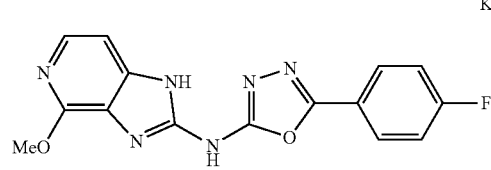

5-(4-Fluorophenyl)-N-(4-methoxy-1H-imidazo[4,5-c]pyridin-2-yl)-1,3,4-oxadiazol-2-amine (KD-002)

To an oven-dried, 40 mL vial with a magnetic stir bar was added 5-(4-fluorophenyl)-1,3,4-oxadiazol-2-amine (0.1 g, 0.35 mmol), 2-methoxypyridine-3,4-diamine (0.055 g, 0.39 mmol), K₂CO₃ (0.107 g, 0.77 mmol) and DMF (3 mL). The reaction was flushed with nitrogen, sealed, placed in a heating block at 120° C. and stirred overnight (16h). The reaction was cooled to rt and solvent reduced to ~1 mL. Cold water (25 mL) was added and neutralized to ~pH 7 with the addition of 1N HCl. The solid was collected and washed with water. Recrystallization from MeOH afforded 5-(4-fluorophenyl)-N-(4-methoxy-1H-imidazo[4,5-c]pyridin-2-yl)-1,3,4-oxadiazol-2-amine. ¹H NMR (500 MHz, DMSO-d6) δ 7.95 (dd, 2H), 7.85 (s, 1H), 7.39 (t, 2H), 7.16 (s, 1H), 3.99 (s, 3H). LCMS [M+H] 327.1.

KD-003

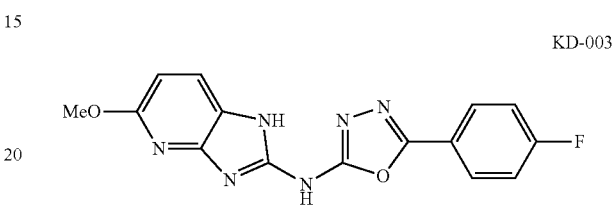

5-(4-Fluorophenyl)-N-(5-methoxy-1H-imidazo[4,5-b]pyridin-2-yl)-1,3,4-oxadiazol-2-amine (KD-003)

The target compound was produced in a similar fashion as in Scheme 1 from 5-(4-fluorophenyl)-1,3,4-oxadiazol-2-amine and 6-methoxypyridine-2,3-diamine. ¹H NMR (500 MHz, DMSO-d₆) δ 7.86 (dd, 2H), 7.41 (d, 1H), 7.33 (t, 2H), 6.16 (d, 1H), 3.78 (s, 3H). LCMS [M+H] 327.1.

KD-004

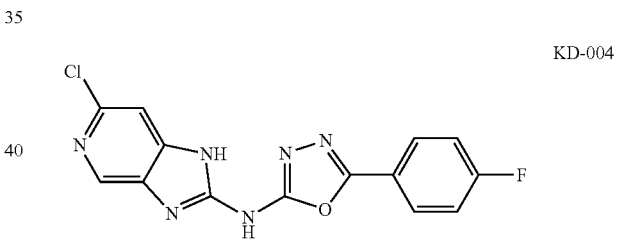

N-(6-Chloro-1H-imidazo[4,5-c]pyridin-2-yl)-5-(4-fluorophenyl)-1,3,4-oxadiazol-2-amine (KD-004)

¹H NMR (500 MHz, DMSO d6) δ 8.31 (s, 1H), 7.97 (t, 2H), 7.40 (t, 2H), 7.35 (s, 1H). LCMS [M+H] 331.1

KD-005

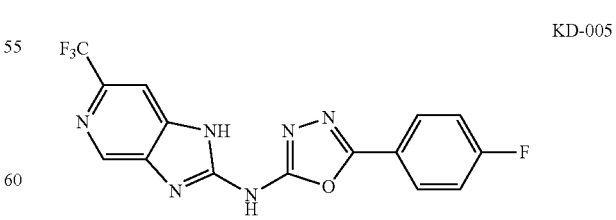

5-(4-Fluorophenyl)-N-(6-(trifluoromethyl)-1H-imidazo[4,5-c]pyridin-2-yl)-1,3,4-oxadiazol-2-amine (KD-005) ¹H NMR (500 MHz, DMSO d6) δ 8.66 (s, 1H), 7.97 (dd, 2H), 7.76 (s, 1H), 7.40 (t, 2H). LCMS [M+H] 365.1.

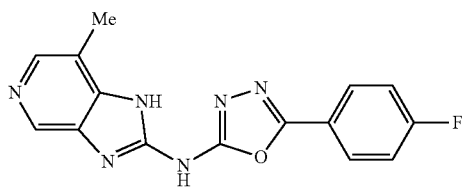

5-(4-Fluorophenyl)-N-(7-methyl-1H-imidazo[4,5-c]pyridin-2-yl)-1,3,4-oxadiazol-2-amine (KD-006)

$^1$H NMR (500 MHz, DMSO d6) δ 8.61 (s, 1H), 8.42 (s, 1H), 7.99 (dd, 2H), 7.42 (t, 2H), 2.49 (s, 3H). LCMS [M+H] 311.2.

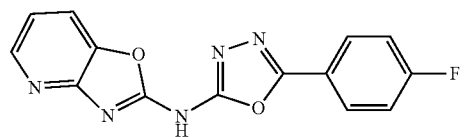

N-(5-(4-Fluorophenyl)-1,3,4-oxadiazol-2-yl)oxazolo[4,5-b]pyridin-2-amine (KD-007)

$^1$H NMR (500 MHz, DMSO-$d_6$) δ 8.04-7.88 (m, 4H), 7.49-7.35 (m, 3H), 6.55 (s, 1H). LCMS [M+H] 298.2.

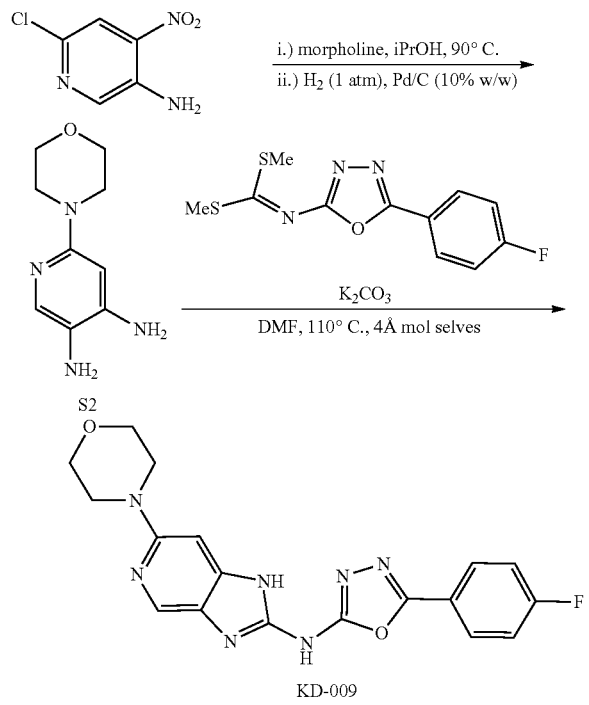

6-Morpholinopyridine-3,4-diamine (S2)

To a 20 mL pressure vial equipped with a magnetic stir bar was added 2-chloro-5-nitropyridine-4-amine (0.20 g, 1.15 mmol), morpholine (0.69 mL, 11.5 mmol) and isopropanol (5 mL). The flask was heated to 90° C., and the reaction was allowed to proceed for 18 hours. The reaction was then portioned between dichloromethane (20 mL) and sat. NaHCO$_3$ (20 mL). The organics were collected, and the aqueous phase was extracted with dichloromethane (3×20 mL). The organics were collected and dried over Na$_2$SO$_4$, filtered, and concentrated under reduced pressure. The resulting yellow solid was taken up in freshly distilled methanol (10 mL) and transferred to a flame-dried 50 mL round bottom flask equipped with a magnetic stir bar. The atmosphere was replaced with N$_2$, and Pd/C (20 mg, 10% w/w) was added. The atmosphere was purged with H$_2$, and the reaction proceeded under atmospheric H$_2$ for 16 hours. The resulting suspension was filtered over diatomaceous earth and concentrated to yield a yellow solid, which was used without further purification. $^1$H NMR (500 MHz, DMSO-d6) 7.31 (s, 1H), 5.92 (s, 1H), 5.21, (s, 2H), 3.92 (s, 2H), 3.63 (t, 4H), 3.09 (t, 4H). LCMS [M+H] 195.4.

5-(4-Fluorophenyl)-N-(6-morpholino-1H-imidazo[4,5-c]pyridin-2-yl)-1,3,4-oxadiazol-2-amine (KD-009).

To an oven-dried, 20 mL vial equipped with a magnetic stir bar was added 5-(4-fluorophenyl)-1,3,4-oxadiazol-2-amine (0.066 g, 0.26 mmol), 6-morpholinopyridine-3,4-diamine (0.050 g, 0.26 mmol), K$_2$CO$_3$ (0.072 g, 0.52 mmol), 4A molecular sieves (100 mg, powdered), and DMF (2 mL). The reaction was flushed with nitrogen, sealed, placed in a heating block at 110° C. and stirred overnight for 16h. The reaction was cooled to rt and filtered. The solid was washed with hot MeOH (15 mL), and the resulting filtrate evaporated under reduced pressure. The resulting mixture was diluted with water (5 mL), and was neutralized to ~pH 7 with the addition of 1N HCl. The resulting precipitate was collected and washed with water. Recrystallization from MeOH/Acetone followed by HPLC purification (C18 0-90 0.1% TFA in water/0.1% TFA in CH$_3$CN, 254 nM) afforded the TFA salt upon removal of the solvent. Addition of 1 mL of 2.0 M HCl in MeOH and removal of solvent afforded 5-(4-fluorophenyl)-N-(6-morpholino-1H-imidazo[4,5-c]pyridin-2-yl)-1,3,4-oxadiazol-2-amine hydrochloride salt. $^1$H NMR (500 MHz, DMSO d6) δ 7.97 (s, 1H), 7.97 (dd, 2H), 7.39 (t, 2H), 6.89 (s, 1H), 3.75 (t, 4H), 3.58 (t, 4H). LCMS [M+H] 381.2.

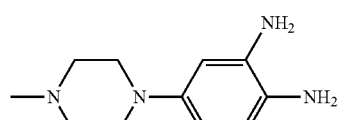

6-(4-Methylpiperazin-1-yl)pyridine-3,4-diamine (S3) was produced in a similar fashion as in Scheme 2 from 2-chloro-5-nitropyridine-4-amine and N-methylpiperazine. LCMS [M+H] 208.3.

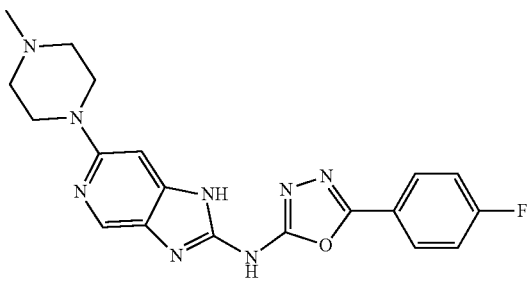

5-(4-Fluorophenyl)-N-(6-(4-methylpiperazin-1-yl)-1H-imidazo[4,5-c]pyridin-2-yl)-1,3,4-oxadiazol-2-amine (KD-010) was produced in a similar fashion as in Scheme 2 from 6-(4-methylpiperazin-1-yl)pyridine-3,4-diamine and 5-(4-fluorophenyl)-1,3,4-oxadiazol-2-amine. $^1$H NMR (500 MHz, DMSO d6) δ 8.14 (s, 1H), 7.95 (dd, 2H), 7.37 (t, 2H), 6.63 (s, 1H), 3.37 (t, 4H), 2.48 (s, 3H), 2.41 (t, 4H). LCMS [M+H] 395.2.

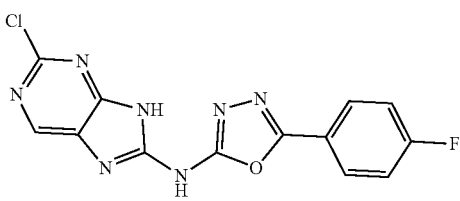

N-(2-Chloro-9H-purin-8-yl)-5-(4-fluorophenyl)-1,3,4-oxadiazol-2-amine (KD-013)

$^1$H NMR (500 MHz, DMSO d6) δ 8.53 (s, 1H), 7.99 (dd, 2H), 7.42 (t, 2H). LCMS [M+H] 332.1.

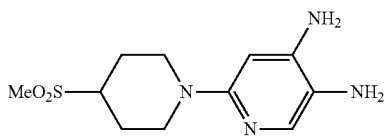

6-(4-(Methylsulfonyl)piperidin-1-yl)pyridine-3,4-diamine (S4) was produced in a similar fashion as in Scheme 2 from 2-chloro-5-nitropyridine-4-amine and 4-(methylsulfonyl)piperidine. $^1$H NMR (500 MHz, DMSO-d$_6$) δ 7.30 (s, 1H), 5.99 (s, 1H), 5.23 (s, 2H), 4.13-3.98 (m, 2H), 3.20 (ddt, 1H), 2.90 (s, 3H), 2.60 (td, 2H), 2.01-1.88 (m, 2H), 1.55 (qd, 2H). LCMS [M+H] 271.2.

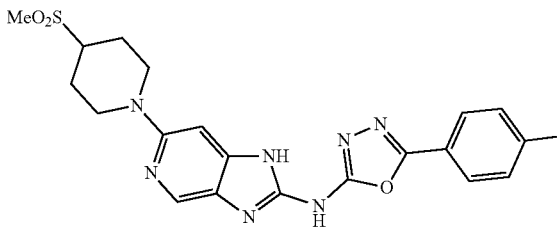

5-(4-Fluorophenyl)-N-(6-(4-(methylsulfonyl)piperidin-1-yl)-1H-imidazo[4,5-c]pyridin-2-yl)-1,3,4-oxadiazol-2-amine (KD-015) was produced in a similar fashion as in Scheme 2 from 6-(4-(methylsulfonyl)piperidin-1-yl)pyridine-3,4-diamine and 5-(4-fluorophenyl)-1,3,4-oxadiazol-2-amine. $^1$H NMR (500 MHz, DMSO d6) δ 7.99 (dd, 2H), 7.97 (s, 1H), 7.40 (t, 2H), 6.94 (s, 1H), 4.29 (d, 2H), 3.45 (t, 1H), 3.18 (t, 2H), 2.96 (s, 3H), 2.14 (d, 2H), 1.74-1.67 (m, 2H). LCMS [M+H] 458.2.

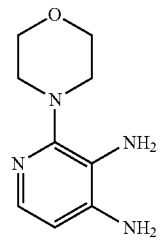

2-Morpholinopyridine-3,4-diamine (S5) was produced in a similar fashion as in Scheme 2 from 2-chloro-3-nitropyridin-4-amine and morpholine. $^1$H NMR (500 MHz, DMSO-d$_6$) δ 7.30 (d, 1H), 6.27 (d, 1H), 5.26 (s, 2H), 4.07 (s, 2H), 3.75-3.67 (m, 4H), 2.90-2.83 (m, 4H). LCMS [M+H] 195.3.

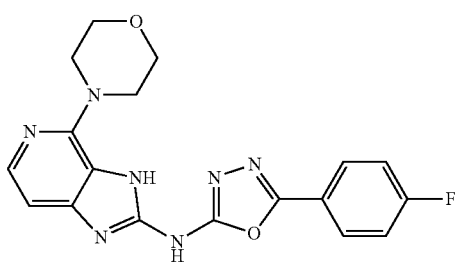

5-(4-Fluorophenyl)-N-(4-morpholino-3H-imidazo[4,5-c]pyridin-2-yl)-1,3,4-oxadiazol-2-amine (KD-016) was produced in a similar fashion as in Scheme 2 from 2-morpholinopyridine-3,4-diamine and 5-(4-fluorophenyl)-1,3,4-oxadiazol-2-amine. $^1$H NMR (500 MHz, DMSO-d$_6$) δ 7.94 (dd, 2H), 7.68 (d, 1H), 7.43 (t, 2H), 7.20 (d, 1H), 4.17 (t, 4H), 3.81 (t, 4H). LCMS [M+H] 382.1.

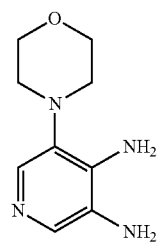

5-Morpholinopyridine-3,4-diamine (S6)

To a 20 mL vial equipped with a magnetic stir bar was added 3-bromo-5-nitropyridin-4-amine (0.20 g, 0.92 mmol) and morpholine (5 mL). The reaction was flushed with nitrogen, sealed, placed in a heating block at 110° C. and stirred for 48 h. To the reaction was extracted with dichloromethane (20 mL) and sat. NaHCO₃ (20 mL). The organic layer was collected, and the aqueous phase was extracted with dichloromethane (3×20 mL). The organics were collected and dried over Na₂SO₄, filtered, and concentrated under reduced pressure. The resulting yellow solid was purified by column chromatography (2.5% MeOH/CH₂Cl₂). The resulting solid was recrystallized from hot MeOH to yield fine yellow needles, which were then taken up in freshly distilled methanol (10 mL) and transferred to a flame-dried 50 mL round bottom flask equipped with a magnetic stir bar. The atmosphere was replaced with N₂, and Pd/C (20 mg, 10% w/w) was added. The flask was purged with H₂, and the reaction stirred under atmospheric H₂ for 16h. The resulting suspension was filtered over Celite and concentrated to yield a yellow solid. LCMS [M+H] 195.3.

freshly distilled MeOH (15 mL) and transferred to a 50 mL round bottom flask equipped with a magnetic stir bar. The atmosphere was replaced with N₂, and Pd/C (10% w/w, 15 mg) was added in a single portion. The reaction was flushed with H₂(g), and the reaction mixture stirred under H₂(g) 16h. The material was filtered over Celite and concentrated to yield a tan solid (64 mg), which was used without further purification. ¹H NMR (500 MHz, Chloroform-d) δ 8.26 (d, 1H), 7.36-7.28 (m, 1H), 7.09-7.06 (m, 1H), 7.04 (dd, 1H), 7.00-6.94 (m, 1H), 6.66 (d, 1H), 5.51 (s, 2H), 3.84 (s, 3H).

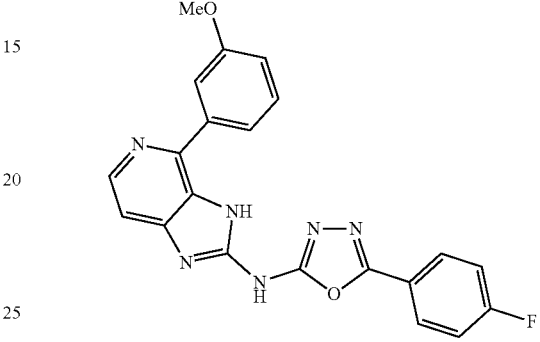

5-(4-Fluorophenyl)-N-(4-(3-methoxyphenyl)-3H-imidazo[4,5-c]pyridin-2-yl)-1,3,4-oxadiazol-2-amine (KD-18)

The title compound was prepared from 2-(3-methoxyphenyl)pyridine-3,4-diamine and dimethyl (5-(4-fluorophenyl)-1,3,4-oxadiazol-2-yl)carbonimidodithioate. ¹H NMR (500 MHz, DMSO-d₆) δ 88.41-8.38 (m, 1H), 7.99-7.94 (m, 2H), 7.58-7.41 (m, 3H), 7.41 (t, 2H), 7.13-7.08 (M, 2H), 3.86 (t, 3H). LCMS [M+H] 403.2.

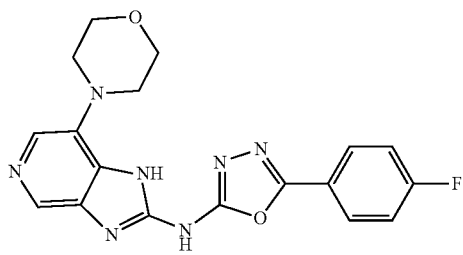

KD-017

5-(4-Fluorophenyl)-N-(7-morpholino-1H-imidazo[4,5-c]pyridin-2-yl)-1,3,4-oxadiazol-2-amine (KD-017) was produced in a similar fashion as in Scheme 2 from 5-morpholinopyridine-3,4-diamine and 5-(4-fluorophenyl)-1,3,4-oxadiazol-2-amine. ¹H NMR (500 MHz, DMSO d6) δ 8.16 (s, 1H), 7.94 (t, 2H), 7.37 (t, 2H), 6.64 (s, 1H), 3.70 (t, 4H), 3.33 (t, 4H). LCMS [M+H]382.1

2-(3-Methoxyphenyl)pyridine-3,4-diamine

To a flame dried 50 mL round bottom flask equipped with a magnetic stir bar under N₂ atmosphere was added 2-chloro-3-nitropyridin-4-amine (285 mg, 1.64 mmol), (3-methoxyphenyl)boronic acid (375 mg, 2.47 mmol), K₂CO₃ (566 mg, 4.1 mmol), 1,4-dioxane (15 mL), and H₂O (1.5 mL). The solution was degassed by bubbling nitrogen through the solution for 30 min. Pd(PPh₃)₄ (185 mg, 0.16 mmol) was then added in a single portion, and the reaction was sealed and allowed to proceed at 90° C. for 16h. The reaction material was concentrated, loaded onto silica gel, and purified by flash chromatography (1:1 hexanes/EtOAc) to yield a tan solid. The material was then dissolved in Scheme 3

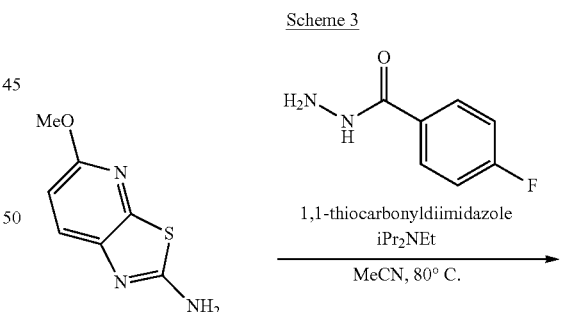

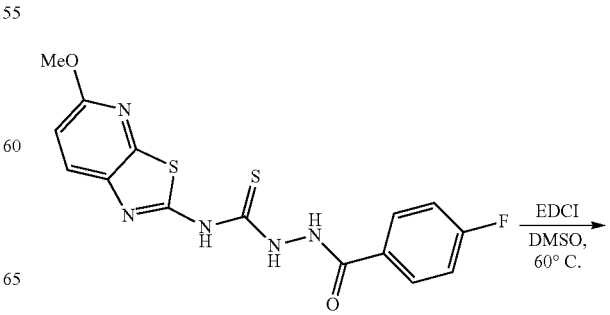

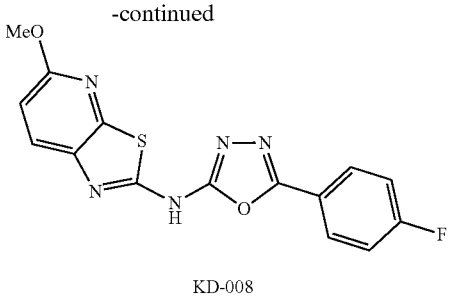

KD-008

5-(4-Fluorophenyl)-N-(5-methoxythiazolo[5,4-b]pyridin-2-yl)-1,3,4-oxadiazol-2-amine (KD-008)

To a flame dried 50 mL flask equipped with a magnetic stir bar was added 5-methoxythiazolo[5,4-b]pyridin-2-amine (0.208 g, 1.14 mmol), iPr₂NEt (0.389 mL, 2.29 mmol), and acetonitrile (10 mL). 1,1-thiocarbonyldiimidazole (204 mg, 1.14 mmol) was added in a single portion, and the reaction was heated to 80° C. and allowed to proceed until complete consumption of starting material was observed by LC-MS (6 hours). 4-Fluorobenzohydrazide (0.154 g, 1.00 mmol) was then added in a single portion, and the reaction was allowed to stir overnight 16h. Saturated aq. NaHCO₃ was added and extracted with CH₂Cl₂ (3×25 mL). The organics were collected and dried over Na₂SO₄, filtered, and concentrated under reduced pressure. The resulting off-white solid was then dissolved in DMSO (4 mL) and transferred to a 25 mL round bottom flask. EDC (0.167 g, 0.86 mmol) was then added in a single portion, and the reaction was heated to 60° C. The reaction was stirred for 6h, and then the contents were poured into H₂O. The resulting precipitate was collected by vacuum filtration and washed with EtOAc. The resulting solid was recrystallized from hot MeOH to yield 5-(4-fluorophenyl)-N-(5-methoxythiazolo[5,4-b]pyridin-2-yl)-1,3,4-oxadiazol-2-amine as a yellow solid. LCMS [M+H] 344.0.

Scheme 4

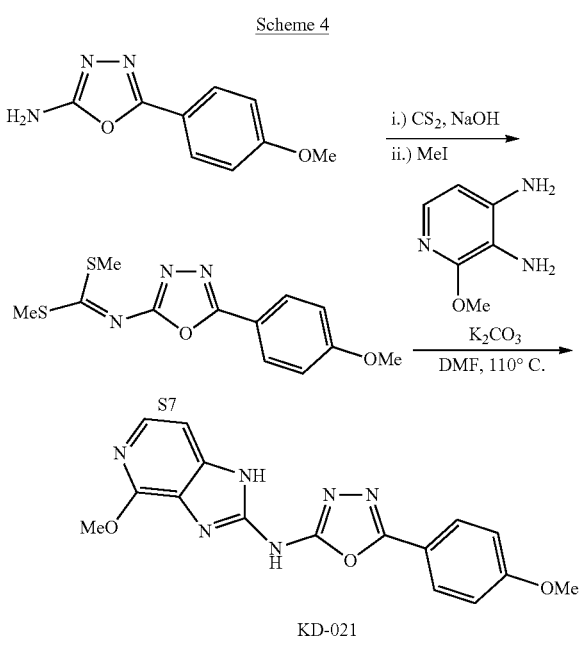

KD-021

Dimethyl (5-(4-methoxyphenyl)-1,3,4-oxadiazol-2-yl)carbonimidodithioate (S7) was produced in a similar fashion to S1 in Scheme 1 from 5-(4-methoxyphenyl)-1,3,4-oxadiazol-2-amine. ¹H NMR (500 MHz, DMSO-d₆) δ 7.90 (d, 2H), 7.11 (d, 2H), 3.83 (s, 3H), 2.65 (s, 6H). LCMS [M+H] 296.2.

N-(4-methoxy-1H-imidazo[4,5-c]75yridine-2-yl)-5-(4-methoxyphenyl)-1,3,4-oxadiazol-2-amine (KD-021) was produced in a similar fashion to KD-001 in Scheme 1 from S6. ¹H NMR (500 MHz, DMSO-d₆) δ 7.88-7.79 (m, 3H), 7.15 (d, 1H), 7.09 (d, 2H), 3.99 (s, 3H), 3.82 (s, 3H). LCMS [M+H] 339.2.

Scheme 5

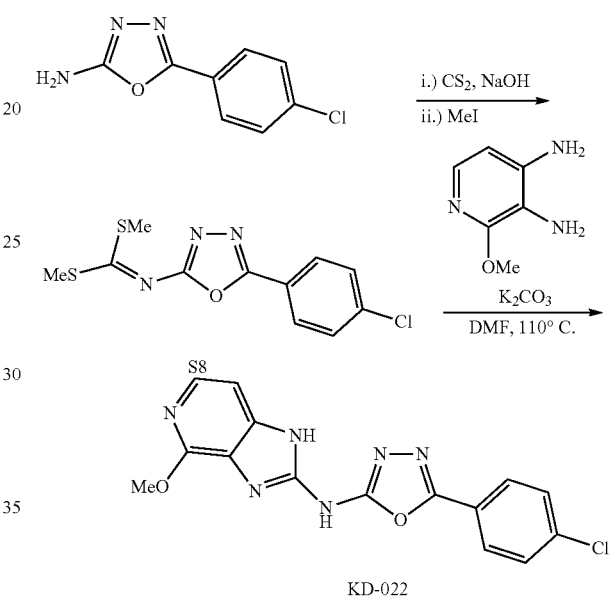

KD-022

Dimethyl (5-(4-chlorophenyl)-1,3,4-oxadiazol-2-yl)carbonimidodithioate (S8) was produced in a similar fashion to S1 in Scheme 1 from 5-(4-chlorophenyl)-1,3,4-oxadiazol-2-amine. ¹H NMR (500 MHz, DMSO-d₆) δ 7.97 (d, 2H), 7.64 (d, 2H), 2.66 (s, 6H). LCMS [M+H] 300.1.

N-(4-chloro-1H-imidazo[4,5-c]75yridine-2-yl)-5-(4-methoxyphenyl)-1,3,4-oxadiazol-2-amine (KD-022) was produced in a similar fashion to KD-001 in Scheme 1 from S7. ¹H NMR (500 MHz, DMSO-d6) δ 7.91 (d, J=8.5 Hz, 2H), 7.86 (d, J=5.5 Hz, 1H), 7.61 (d, J=8.6 Hz, 2H), 7.17 (d, J=5.5 Hz, 1H), 3.99 (s, 3H). LCMS [M+H] 343.1.

Scheme 6

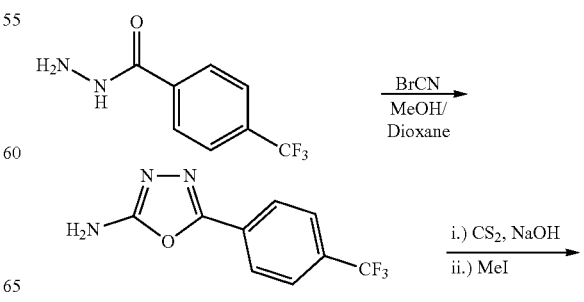

S9

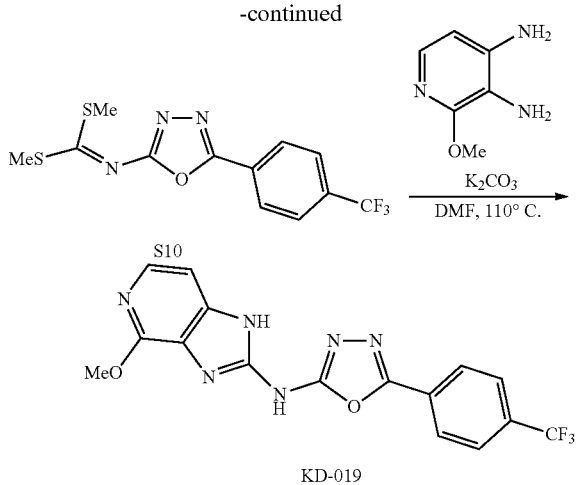

KD-019

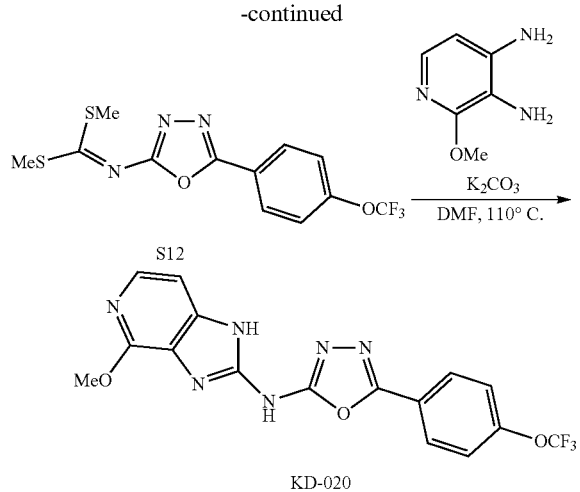

KD-020

5-(4-(trifluoromethyl)phenyl)-1,3,4-oxadiazol-2-amine (S9)

To a 25 mL roundbottom flask equipped with a magnetic stir bar was added 4-(trifluoromethyl)benzohydrazide (200 mg, 0.98 mmol), methanol (6 mL), and 1,4-dioxane (3 mL) under an $N_2$ atmosphere. Cyanogen bromide (155 mg, 1.47 mmol) was added in a single portion, and the reaction was allowed to proceed for one hour. Sodium bicarbonate (150 mg) was then added in a single portion, and the resulting mixture was stirred vigorously for 16 hours. The resulting precipitate was collected by vacuum filtration, and washed with copious amounts of water to yield a white solid (160 mg). $^1$H NMR (500 MHz, DMSO-$d_6$) δ 7.97 (d, 2H), 7.8 (d, 2H), 7.41 (s, 2H). LCMS [M+H] 230.1.

Dimethyl (5-(4-(trifluoromethyl)phenyl)-1,3,4-oxadiazol-2-yl) carbonimidodithioate (S10) was produced in a similar fashion to SI in Scheme 1 from 5-(4-(trifluoromethyl)phenyl)-1,3,4-oxadiazol-2-amine (s8). $^1$H NMR (500 MHz, DMSO-$d_6$) δ 8.18 (d, 2H), 7.94 (d, 2H), 2.68 (s, 6H). LCMS [M+H] 334.0.

N-(4-methoxy-1H-imidazo[4,5-c]pyridin-2-yl)-5-(4-(trifluoromethyl)phenyl)-1,3,4-oxadiazol-2-amine (KD-019) was produced in a similar fashion to KD-001 in Scheme 1 from S10.

$^1$H NMR (500 MHz, DMSO-$d_6$) δ 8.11 (d, 2H), 7.91 (d, 2H), 7.87 (d, 1H), 7.18 (d, 1H), 4.00 (s, 3H). LCMS [M+H] 377.0.

Scheme 7

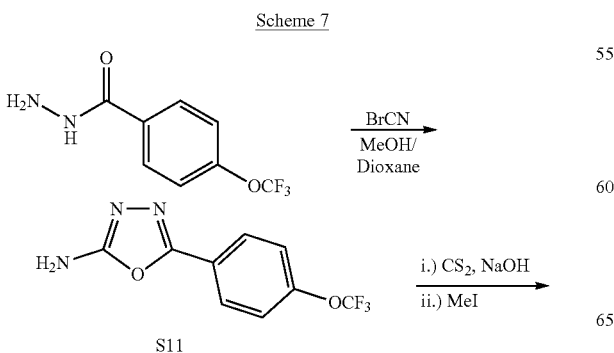

5-(4-(trifluoromethoxy)phenyl)-1,3,4-oxadiazol-2-amine (S11) was produced in a similar fashion to s8 in Scheme 6 from 4-(trifluoromethoxy)benzohydrazide. $^1$H NMR (500 MHz, DMSO-$d_6$) δ 7.92-7.87 (m, 2H), 7.50 (d, 2H), 7.29 (s, 2H). LCMS [M+H] 246.1.

Dimethyl (5-(4-(trifluoromethoxy)phenyl)-1,3,4-oxadiazol-2-yl)carbonimidodithioate (S12) was produced in a similar fashion to S1 in Scheme 1 from 5-(4-(trifluoromethoxy)phenyl)-1,3,4-oxadiazol-2-amine (s10). $^1$H NMR (500 MHz, DMSO-$d_6$) δ 8.12-8.06 (m, 2H), 7.56 (d, 2H), 2.67 (s, 6H). LCMS [M+H] 350.0.

N-(4-methoxy-1H-imidazo[4,5-c]pyridin-2-yl)-5-(4-(trifluoromethoxy)phenyl)-1,3,4-oxadiazol-2-amine (KD-020) was produced in a similar fashion to KD-001 in Scheme 1 from s11. $^1$H NMR (500 MHz, DMSO-$d_6$) δ 8.07-7.98 (m, 2H), 7.86 (d, 1H), 7.56-7.51 (m, 2H), 7.17 (d, 1H), 3.99 (s, 3H). LCMS [M+H] 393.0.

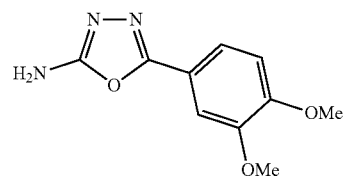 [SMILES: COc1ccc(-c2nnc(N)o2)cc1OC]

5-(3,4-Dimethoxyphenyl)-1,3,4-oxadiazol-2-amine

The title compound was produced in a similar fashion to Scheme 5 from 3,4-dimethoxybenzohydrazide. LCMS [M+H] 222.0.

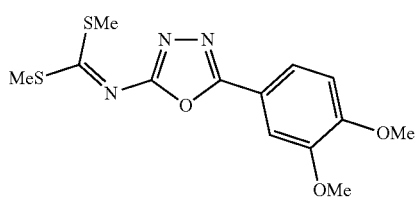 [SMILES: COc1ccc(-c2nnc(N=C(SC)SC)o2)cc1OC]

Dimethyl (5-(3,4-dimethoxyphenyl)-1,3,4-oxadiazol-2-yl)carbonimidodithioate

The title compound was produced in a similar fashion to Scheme 5 from 5-(3,4-dimethoxyphenyl)-1,3,4-oxadiazol-2-amine. LCMS [M+H] 326.0.

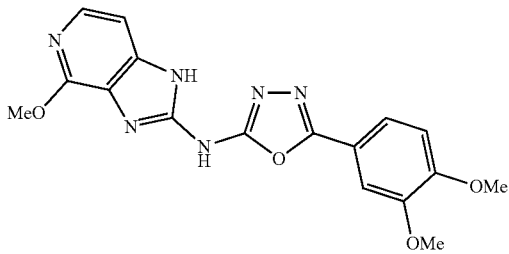 [SMILES: COc1ccc(-c2nnc(Nc3nc4c(OC)nccc4[nH]3)o2)cc1OC]

N-(4-Methoxy-1H-imidazo[4,5-c]pyridin-2-yl)-5-(3,4-dimethoxyphenyl)-1,3,4-oxadiazol-2-amine (KD-025)

The title compound was produced in a similar fashion to Scheme 5 from 2-methoxypyridine-3,4-diamine and dimethyl (5-(3,4-dimethoxyphenyl)-1,3,4-oxadiazol-2-yl)carbonimidodithioate. $^1$H NMR (500 MHz, DMSO-4) δ 7.55 (d, 1H), 7.39-7.33 (m, 2H), 7.07 (d, 1H), 6.86 (d, 1H), 3.93 (s, 3H), 3.83 (s, 3H), 3.80 (s, 3H). LCMS [M+H] 369.1.

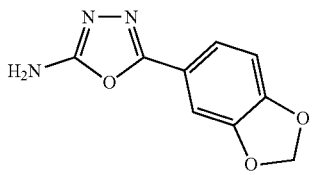 [SMILES: Nc1nnc(-c2ccc3c(c2)OCO3)o1]

5-(Benzo[d][1,3]dioxol-5-yl)-1,3,4-oxadiazol-2-amine

The title compound was produced in a similar fashion to Scheme 5 from benzo[d][1,3]dioxole-5-carbohydrazide. LCMS [M+H] 206.0.

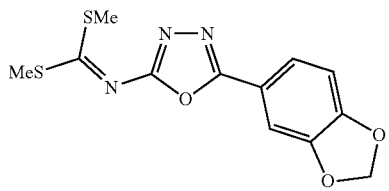 [SMILES: CSC(=Nc1nnc(-c2ccc3c(c2)OCO3)o1)SC]

Dimethyl (5-(benzo[d][1,3]dioxol-5-yl)-1,3,4-oxadiazol-2-yl)carbonimidodithioate.

The title compound was produced in a similar fashion to Scheme 5 from 5-(benzo[d][1,3]dioxol-5-yl)-1,3,4-oxadiazol-2-amine.

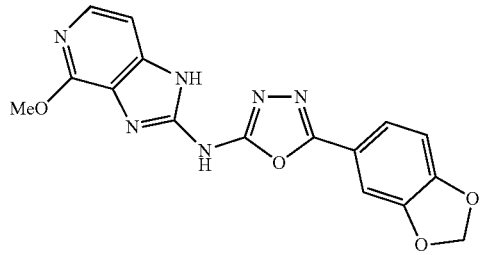 [SMILES: COc1nccc2[nH]c(Nc3nnc(-c4ccc5c(c4)OCO5)o3)nc12]

N-(4-Methoxy-1H-imidazo[4,5-c]pyridin-2-yl)-5-(benzo[d][1,3]dioxol-5-yl)-1,3,4-oxadiazol-2-amine (KD-026)

The title compound was produced in a similar fashion to Scheme 5 from 2-methoxypyridine-3,4-diamine and dimethyl (5-(benzo[d][1,3]dioxol-5-yl)-1,3,4-oxadiazol-2-yl)carbonimidodithioate. $^1$H NMR (500 MHz, DMSO-d$_6$) δ 7.85 (d, 1H), 7.43 (d, 1H), 7.37 (s, 1H), 7.15 (d, 1H), 7.07 (d, 1H), 6.12 (s, 2H), 3.99 (s, 3H). LCMS [M+H] 353.1.

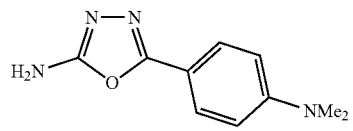 [SMILES: CN(C)c1ccc(-c2nnc(N)o2)cc1]

5-(4-(Dimethylamino)phenyl)-1,3,4-oxadiazol-2-amine

The title compound was produced in a similar fashion to Scheme 5 from 4-(dimethylamino) benzohydrazide. LCMS [M+H] 205.1.

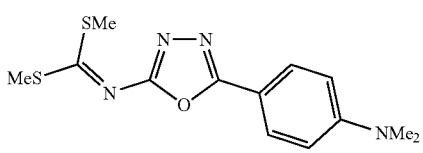 [SMILES: CSC(=Nc1nnc(-c2ccc(N(C)C)cc2)o1)SC]

Dimethyl (4-(dimethylamino)phenyl)-1,3,4-oxadiazol-2-yl)carbonimidodithioate The title compound was produced in a similar fashion to Scheme 5 from 5-(4-(dimethylamino)phenyl)-1,3,4-oxadiazol-2-amine LCMS [M+H] 309.0.

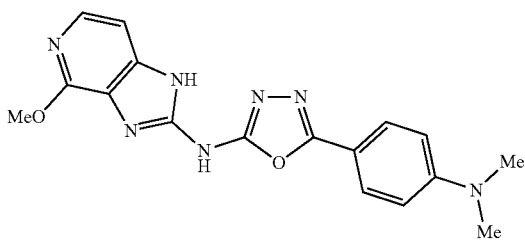 [SMILES: COc1nccc2[nH]c(Nc3nnc(-c4ccc(N(C)C)cc4)o3)nc12]

N-(4-Methoxy-1H-imidazo[4,5-c]pyridin-2-yl)-5-(4-(dimethylamino)phenyl)-1,3,4-oxadiazol-2-amine (KD-027)

The title compound was produced in a similar fashion to Scheme 5 from 2-methoxypyridine-3,4-diamine and dimethyl (4-(dimethylamino)phenyl)-1,3,4-oxadiazol-2-yl)carbonimidodithioate. $^1$H NMR (500 MHz, DMSO-d$_6$) δ 7.84 (d, 1H), 7.69 (d, 2H), 7.15 (d, 1H), 6.80 (d, 2H), 3.99 (s, 3H), 2.98 (s, 6H). LCMS [M+H] 352.1.

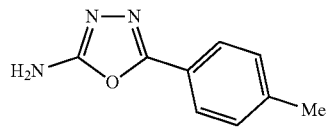 [SMILES: Cc1ccc(-c2nnc(N)o2)cc1]

5-(p-Tolyl)-1,3,4-oxadiazol-2-amine

The title compound was produced in a similar fashion to Scheme 5 from p-tolylbenzohydrazide.

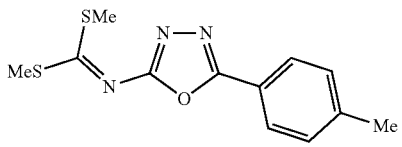 [SMILES: CSC(=Nc1nnc(-c2ccc(C)cc2)o1)SC]

Dimethyl (p-tolyl)-1,3,4-oxadiazol-2-yl)carbonimidodithioate

The title compound was produced in a similar fashion to Scheme 5 from 5-(p-tolyl)-1,3,4-oxadiazol-2-amine. LCMS [M+H] 280.0.

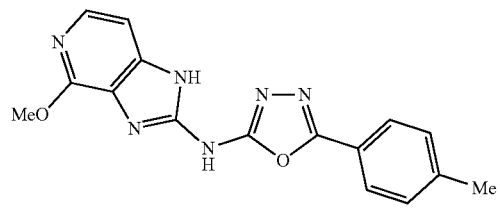 [SMILES: COc1nccc2[nH]c(Nc3nnc(-c4ccc(C)cc4)o3)nc12]

N-(4-methoxy-1H-imidazo[4,5-c]pyridin-2-yl)-5-(p-tolyl)-1,3,4-oxadiazol-2-amine (KD-028)

The title compound was produced in a similar fashion to Scheme 5 from 2-methoxypyridine-3,4-diamine and dimethyl (p-tolyl)-1,3,4-oxadiazol-2-yl)carbonimidodithioate. $^1$H NMR (500 MHz, DMSO-d$_6$) δ 7.85 (d, 1H), 7.79 (d, 2H), 7.35 (d, 2H), 7.16 (d, 1H), 3.99 (s, 3H), 2.37 (s, 3H). LCMS [M+H] 323.1.

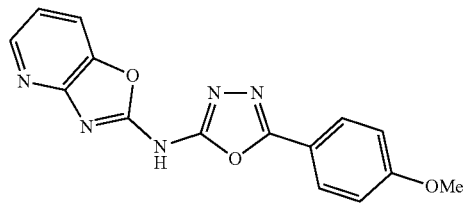 [SMILES: COc1ccc(-c2nnc(Nc3nc4ncccc4o3)o2)cc1]

N-(5-(4-Methoxyphenyl)-1,3,4-oxadiazol-2-yl)oxazolo[4,5-b]pyridin-2-amine (KD-029)

The title compound was produced in a similar fashion to Scheme 4 from 2-aminopyridin-3-ol and dimethyl (5-(4-methoxyphenyl)-1,3,4-oxadiazol-2-yl)carbonimidodithioate. $^1$H NMR (500 MHz, DMSO-d$_6$) δ 7.90 (dd, 1H), 7.78 (d, 2H), 7.35 (dd, 1H), 7.06 (d, 2H), 6.73 (dd, 1H), 3.80 (s, 3H). LCMS [M+H] 310.1.

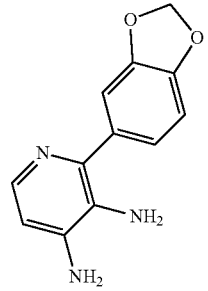 [SMILES: Nc1ccnc(-c2ccc3c(c2)OCO3)c1N]

2-(Benzo[d][1,3]dioxol-5-yl)pyridine-3,4-diamine

The title compound was produced in a similar fashion to Scheme 6 from 2-chloro-3-nitropyridin-4-amine and benzo[d][1,3]dioxol-5-ylboronic acid. $^1$H NMR (400 MHz, Chloroform-d) δ 8.20 (d, 1H), 7.00-6.96 (m, 2H), δ 6.83 (dd, 1H), 6.61 (d, 1H), 5.99 (s, 2H), 5.48 (s, 3H).

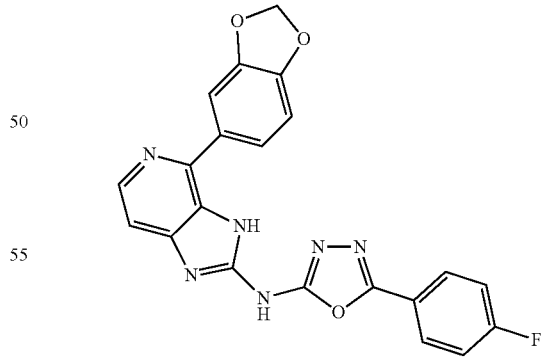

N-(4-(Benzo[d][1,3]dioxol-5-yl)-3H-imidazo[4,5-c]pyridin-2-yl)-5-(4-fluorophenyl)-1,3,4-oxadiazol-2-amine (KD-030)

The title compound was produced in a similar fashion to Scheme 6 from 2-2-(benzo[d][1,3]dioxol-5-yl)pyridine-3,4- diamine and dimethyl (5-(4-fluorophenyl)-1,3,4-oxadiazol-2-yl)carbonimidodithioate. $^1$H NMR (500 MHz, DMSO-d$_6$) δ 8.34 (d, 1H), 7.97 (dd, 2H), 7.54-7.43 (m, 3H), 7.40 (t, 2H), 7.12-7.08 (m, 2H). LCMS [M+H] 417.2.

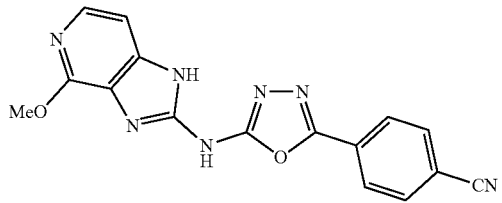 [SMILES: COc1nccc2[nH]c(Nc3nnc(-c4ccc(C#N)cc4)o3)nc12]

4-(5-((4-Methoxy-1H-imidazo[4,5-c]pyridin-2-yl) amino)-1,3,4-oxadiazol-2-yl) benzonitrile (KD-031)

The title compound was produced in a similar fashion to Scheme 5 from 2-methoxypyridine-3,4-diamine and dimethyl (5-(4-cyanophenyl)-1,3,4-oxadiazol-2-yl)carbonimidodithioate. $^1$H NMR (500 MHz, DMSO-d$_6$) δ 8.00 (m, 4H), 7.85 (m, 1H), 7.18 (m, 1H), 3.99 (s, 3H). LCMS [M+H] 334.1.

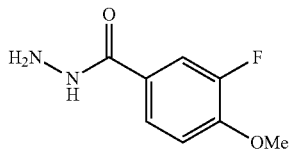 [SMILES: COc1ccc(C(=O)NN)cc1F]

3-Fluoro-4-methoxybenzohydrazide

To a 40 mL pressure vial equipped with a magnetic stir bar under an N$_2$ atmosphere was added methyl 3-fluoro-4-methoxybenzoate (500 mg), ethanol (10 mL), and hydrazine monohydrate (1.5 mL). The flask was then heated to 80° C. for 16h. Upon cooling to room temperature, a solid white precipitate was observed. The contents of the pressure vial were then poured into water (50 mL), and the precipitate was collected by vacuum filtration. The resulting hydrazide was used in the next transformation without further purification.

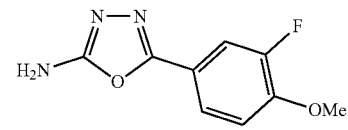 [SMILES: COc1ccc(-c2nnc(N)o2)cc1F]

5-(3-Fluoro-4-methoxyphenyl)-1,3,4-oxadiazol-2-amine

The title compound was produced in a similar fashion to Scheme 5 from 3-fluoro-4-methoxybenzohydrazide.

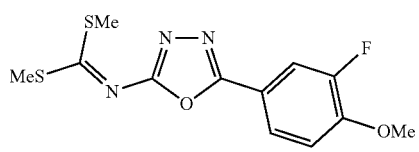 [SMILES: COc1ccc(-c2nnc(N=C(SC)SC)o2)cc1F]

Dimethyl (5-(3-fluoro-4-methoxyphenyl)-1,3,4-oxadiazol-2-yl)carbonimidodithioate The title compound was produced in a similar fashion to Scheme 5 from 5-(p-tolyl)-1,3,4-oxadiazol-2-amine.

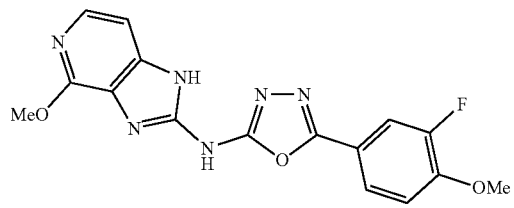 [SMILES: COc1ccc(-c2nnc(Nc3nc4c(OC)nccc4[nH]3)o2)cc1F]

5-(3-Fluoro-4-methoxyphenyl)-N-(4-methoxy-1H-imidazo[4,5-c]pyridin-2-yl)-1,3,4-oxadiazol-2-amine (KD-032)

The title compound was produced in a similar fashion to Scheme 5 from dimethyl (5-(3-fluoro-4-methoxyphenyl)-1,3,4-oxadiazol-2-yl)carbonimidodithioate and 2-methoxypyridine-3,4-diamine. $^1$H NMR (500 MHz, DMSO-d) δ 9.82 (s, 1H), 7.71-7.03 (m, 5H), 3.95 (s, 3H), 3.91 (s, 3H). LCMS [M+H] 357.1.

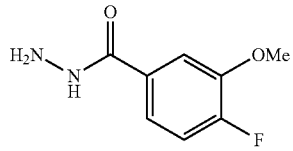 [SMILES: COc1cc(C(=O)NN)ccc1F]

4-Fluoro-3-methoxybenzohydrazide

To a 40 mL pressure vial equipped with a magnetic stir bar under an N$_2$ atmosphere was added methyl 3-fluoro-4-methoxybenzoate (500 mg), ethanol (10 mL), and hydrazine monohydrate (1.5 mL). The flask was then heated to 80° C. for 16h. Upon cooling to room temperature, a solid white precipitate was observed. The contents of the pressure vial were then poured into water (50 mL), and the precipitate was collected by vacuum filtration. The resulting hydrazide was then used in the next transformation without further purification.

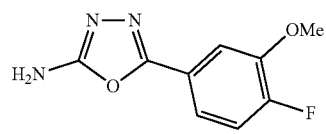 [SMILES: COc1cc(-c2nnc(N)o2)ccc1F]

5-(4-Fluoro-3-methoxyphenyl)-1,3,4-oxadiazol-2-amine

The title compound was produced in a similar fashion to Scheme 5 from 4-fluoro-3-methoxybenzohydrazide.

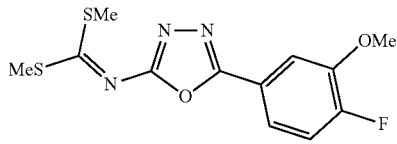 [SMILES: COc1cc(-c2nnc(N=C(SC)SC)o2)ccc1F]

Dimethyl (5-(4-fluoro-3-methoxyphenyl)-1,3,4-oxadiazol-2-yl)carbonimidodithioate The title compound was produced in a similar fashion to Scheme 5 from 5-(4-fluoro-3-methoxyphenyl)-1,3,4-oxadiazol-2-amine.

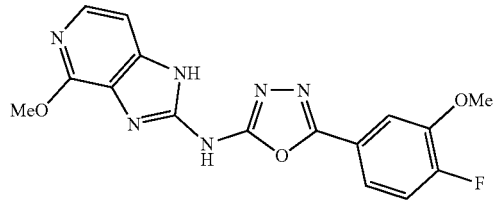 [SMILES: COc1cc(-c2nnc(Nc3nc4c(OC)nccc4[nH]3)o2)ccc1F]

5-(3-Fluoro-4-methoxyphenyl)-N-(4-methoxy-1H-imidazo[4,5-c]pyridin-2-yl)-1,3,4-oxadiazol-2-amine (KD-033)

The title compound was produced in a similar fashion to Scheme 5 from dimethyl (5-(4-fluoro-3-methoxyphenyl)-1,3,4-oxadiazol-2-yl)carbonimidodithioate and 2-methoxypyridine-3,4-diamine. $^1$H NMR (500 MHz, DMSO-d$_6$) δ 7.85 (d, 1H), 7.69-7.66 (m, 2H), 7.33 (t, 1H), 7.16 (d, 1H), 3.98 (s, 3H), 3.90 (s, 3H). LCMS [M+H] 357.1.

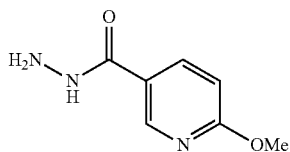 [SMILES: COc1ccc(C(=O)NN)cn1]

6-Methoxynicotinohydrazide

The title compound was produced in a similar fashion to 3-fluoro-4-methoxybenzohydrazide from methyl 6-methoxynicotinate.

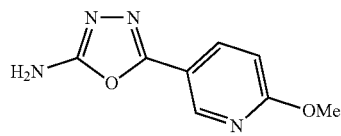 [SMILES: COc1ccc(-c2nnc(N)o2)cn1]

5-(6-Methoxypyridin-3-yl)-1,3,4-oxadiazol-2-amine

The title compound was produced in a similar fashion to Scheme 5 from 6-methoxynicotinohydrazide. LCMS [M+H] 193.1.

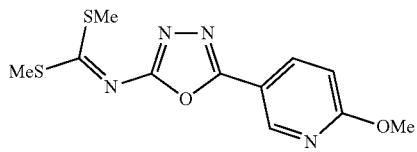 [SMILES: COc1ccc(-c2nnc(N=C(SC)SC)o2)cn1]

Dimethyl (5-(6-methoxypyridin-3-yl)-1,3,4-oxadiazol-2-yl)carbonimidodithioate The title compound was produced in a similar fashion to Scheme 5 from 5-(6-methoxypyridin-3-yl)-1,3,4-oxadiazol-2-amine. LCMS [M+H] 297.0.

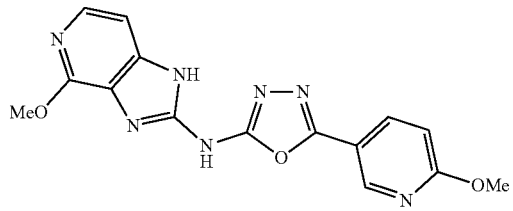 [SMILES: COc1ccc(-c2nnc(Nc3nc4c(OC)nccc4[nH]3)o2)cn1]

N-(4-Methoxy-1H-imidazo[4,5-c]pyridin-2-yl)-5-(6-methoxypyridin-3-yl)-1,3,4-oxadiazol-2-amine (KD-038)

The title compound was produced in a similar fashion to Scheme 5 from dimethyl (5-(6-methoxypyridin-3-yl)-1,3,4-oxadiazol-2-yl)carbonimidodithioate and 2-methoxypyridine-3,4-diamine. $^1$H NMR (500 MHz, DMSO-d$_6$) δ 8.67 (s, 1H), 8.18 (dd, 1H), 7.86 (d, 1H), 7.16 (d, 1H), 7.00 (s, 1H), 3.99 (s, 3H), 3.92 (s, 3H). LCMS [M+H] 340.1.

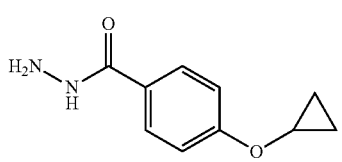 [SMILES: NNC(=O)c1ccc(OC2CC2)cc1]

4-Cyclopropoxybenzohydrazide

The title compound was produced in a similar fashion to 3-fluoro-4-methoxybenzohydrazide from methyl 4-cyclopropoxybenzoate.

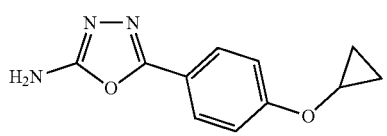 [SMILES: Nc1nnc(-c2ccc(OC3CC3)cc2)o1]

5-(4-Cyclopropoxyphenyl)-1,3,4-oxadiazol-2-amine

The title compound was produced in a similar fashion to Scheme 5 from 4-cyclopropoxybenzohydrazide.

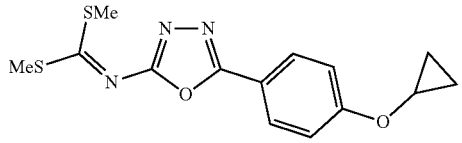 [SMILES: CSC(=Nc1nnc(-c2ccc(OC3CC3)cc2)o1)SC]

Dimethyl (5-(4-cyclopropoxyphenyl)-1,3,4-oxadiazol-2-yl)carbonimidodithioate The title compound was produced in a similar fashion to Scheme 5 from 5-(4-cyclopropoxyphenyl)-1,3,4-oxadiazol-2-amine. LCMS [M+H] 322.1.

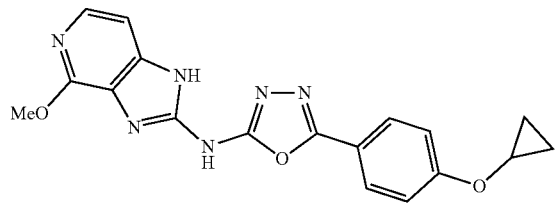 [SMILES: COc1nccc2[nH]c(Nc3nnc(-c4ccc(OC5CC5)cc4)o3)nc12]

5-(4-Cyclopropoxyphenyl)-N-(4-methoxy-1H-imidazo[4,5-c]pyridin-2-yl)-1,3,4-oxadiazol-2-amine (KD-040)

The title compound was produced in a similar fashion to Scheme 5 from dimethyl (5-(4-cyclopropoxyphenyl)-1,3,4-oxadiazol-2-yl)carbonimidodithioate and 2-methoxypyridine-3,4-diamine. $^1$H NMR (500 MHz, DMSO-d) δ 7.87-7.80 (m, 3H), 7.20 (d, 2H), 7.14 (d, 1H), 3.98 (s, 3H), 3.92 (tt, 1H), 0.84-0.76 (m, 2H), 0.73-0.65 (m, 2H). LCMS [M+H] 365.2.

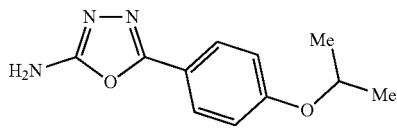 [SMILES: CC(C)Oc1ccc(-c2nnc(N)o2)cc1]

5-(4-Isopropoxyphenyl)-1,3,4-oxadiazol-2-amine

The title compound was produced in a similar fashion to Scheme 5 from 4-isopropoxybenzohydrazide.

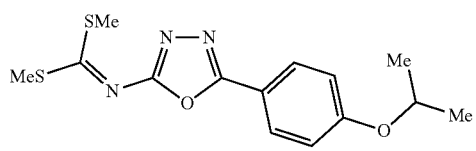 [SMILES: CSC(=Nc1nnc(-c2ccc(OC(C)C)cc2)o1)SC]

Dimethyl (5-(4-isopropoxyphenyl)-1,3,4-oxadiazol-2-yl)carbonimidodithioate

The title compound was produced in a similar fashion to Scheme 5 from 5-(4-isopropoxyphenyl)-1,3,4-oxadiazol-2-amine. LCMS [M+H] 324.0.

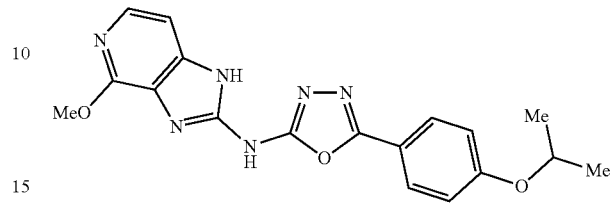

5-(4-Isopropoxyphenyl)-N-(4-methoxy-1H-imidazo[4,5-c]pyridin-2-yl)-1,3,4-oxadiazol-2-amine (KD-041)

The title compound was produced in a similar fashion to Scheme 5 from dimethyl (5-(4-isopropoxyphenyl)-1,3,4-oxadiazol-2-yl)carbonimidodithioate and 2-methoxypyridine-3,4-diamine. $^1$H NMR (500 MHz, DMSO-d$_h$) δ 8.02-7.87 (m, 3H), 7.16-7.06 (m, 3H), 4.76-4.65 (m, 1H), 3.98 (s, 3H), 1.24 (d, 6H). LCMS [M+H] 367.1.

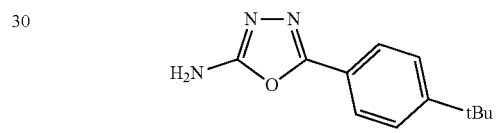

5-(4-(tert-Butyl)phenyl)-1,3,4-oxadiazol-2-amine

The title compound was produced in a similar fashion to Scheme 5 from 4-(tert-butyl)benzohydrazide.

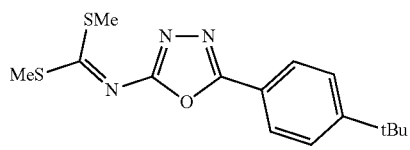 [SMILES: CSC(=Nc1nnc(-c2ccc(C(C)(C)C)cc2)o1)SC]

Dimethyl (5-(4-(tert-butyl)phenyl)-1,3,4-oxadiazol-2-yl)carbonimidodithioate The title compound was produced in a similar fashion to Scheme 5 from 5-(4-(tert-butyl)phenyl)-1,3,4-oxadiazol-2-amine. LCMS [M+H] 322.0.

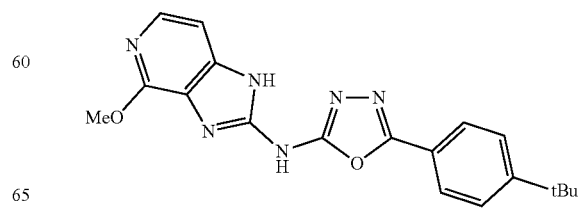

5-(4-(tert-Butyl)phenyl)-N-(4-methoxy-1H-imidazo[4,5-c]pyridin-2-yl)-1,3,4-oxadiazol-2-amine (KD-042)

The title compound was produced in a similar fashion to Scheme 5 from (5-(4-(tert-butyl)phenyl)-1,3,4-oxadiazol-2-yl)carbonimidodithioate. LCMS [M+H] 365.2.

Example 2

Hypoxia-responsive element-driven luciferase screens to identify inhibitors of HIF-2α transcriptional activity.

Screens for inhibitory activity of compounds described herein were performed using 786-0 CCRCC cells that stably express HRE-Luc: 5 copies of the hypoxia-responsive element (HRE) fused to the pGL3 luciferase reporter (Promega Corp, Madison Wis.). 786-0 cells are pVHL deficient and thus constitutively express HIF-2α independently of cellular oxygen tension (Maxwell, Wiesener et al. 1999). Since 786-0 cells lack HIF-1α, HRE-driven luciferase activity is primarily HIF-2α driven, and has been previously validated (Koh, Lemos et al. 2011). Cells were maintained at log phase growth in Dulbecco's minimal essential media (DMEM) with 10% FBS in a humidified incubator at 37° C. with 5% $CO_2$. For screening assays, cells were seeded at a density of 4,000 cells in 50 μl of complete media/well in quadruplicate wells/point in a 96-well plate. 24 hours later, 50 μl of a 2× concentration of test compound was added to each well. Compounds were diluted from a 5-10 mM stock in DMSO and final concentrations of DMSO in each well in controls and treated wells were kept constant at ≤0.6% DMSO. After 24 hours' treatment, luciferase activity was measured using the Steady-Glo Luciferase assay system (Promega Corp) according to the manufacturer's protocol. Cell viability was measured in quadruplicate parallel wells using resazurin as recommended by the manufacturer (R&D systems, Minneapolis, Minn.). Data for luciferase and resazurin were normalized to DMSO treated controls (defining 100%) and wells containing assay reagent but no cells (defining 0%), and graphed using the log inhibitor versus normalized response option in Prism7 Graphpad software. Representative data determined using Steady-Glo luciferase and resazurin are shown in FIGS. 1A and 1B respectively, with error bars showing standard error of the mean (SEM). Filled diamonds, empty squares and empty triangles indicate treatment with KD002, KD007 and KD021 respectively with results for HRE-Luc shown in A. Table 1 shows the range of $IC_{50}$ values for hypoxia-responsive element driven luciferase assays (HIF-2α $IC_{50}$) performed as described in this example.

TABLE 1

Summary HRE-Luc for described compounds

| Example number | HIF-2α HRE-Luc $IC_{50}$ (μM) |
|---|---|
| KD001 | 3.21 |
| KD002 | 1.56 |
| KD003 | 8.16 |
| KD004 | 40.3 |
| KD005HCL | 16.15 |
| KD006TFA | 23.8 |
| KD007 | 3.16 |
| KD008 | 52.3 |
| KD009 | 15.4 |
| KD010 | >100 μM |
| KD013 | 37.6 |
| KD015 | >100 μM |

TABLE 1-continued

Summary HRE-Luc for described compounds

| Example number | HIF-2α HRE-Luc $IC_{50}$ (μM) |
|---|---|
| KD016 | 10.24 |
| KD017 | 16.3 |
| KD018 | 72.67 |
| KD019 | 32.58 |
| KD020 | 16.46 |
| KD021 | 1.4 |
| KD022 | 28.28 |
| KD023 | 1.35 |
| KD024 | 21.9 |
| KD025 | 1.13 |
| KD026 | 2.72 |
| KD027 | 2.83 |
| KD028 | 9.12 |
| KD029 | 6.1 |
| KD030 | 19.89 |
| KD031 | 3.7 |
| KD032 | 1.94 |
| KD033 | 5.07 |
| KD034 | 5.94 |
| KD038 | 7.6 |
| KD040 | 6.86 |
| KD041 | 22.55 |
| KD042 | >100 μM |

For the data shown in FIG. 1, the ratios of resazurin $IC_{50}$ to HRE-Luc $IC_{50}$ were 39.05, 3.2, and 2.75 for KDO02, KDO07 and KD021 respectively. The high ratios of HRE-Luc to resazurin $IC_{50}$s indicates that the decrease in HRE-Luc activity was unlikely to be caused by decreased cell viability.

Figure 2:
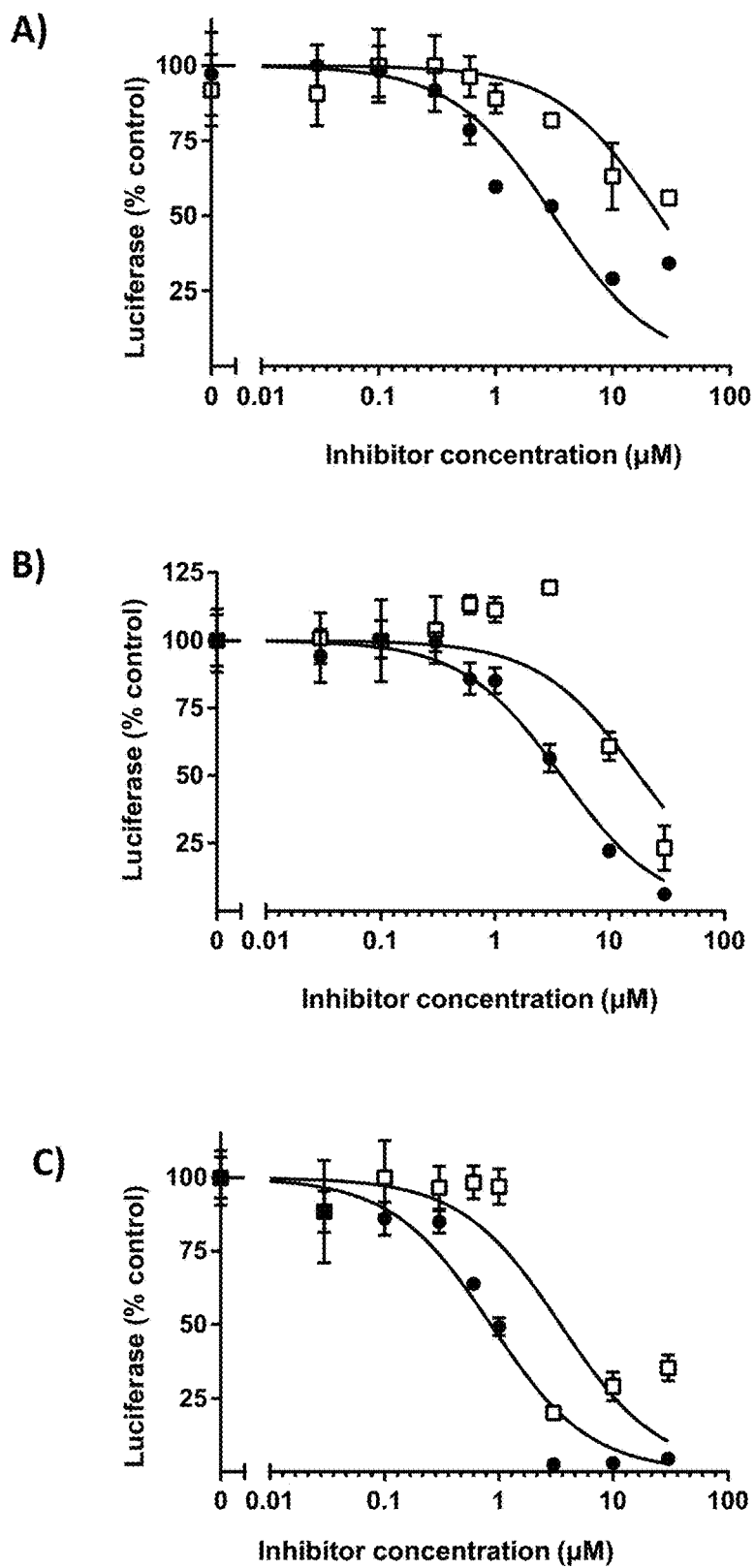
FIG. 2 shows results from parallel luciferase assays performed using 786-0 CCRCC cells stably expressing either HRE-Luciferase (indicating HIF-2α transcriptional activity) or CMV Luciferase (constitutive luciferase expression). Filled circles indicate data from the HRE-Luciferase reporter whereas empty squares indicate data from the CMV-Luciferase reporter. Error bars indicate standard error of the mean (SEM). Parts A, B and C indicate data using KD002, KD007 and KD021 respectively.

Since it is possible that non-specific inhibitors of luciferase activity and/or translation may produce false-positives in our HRE-luciferase screens, counter-screens were performed using 786-0 cells that stably express a constitutively expressed luciferase construct. 786-0 cells stably expressing CMV-driven luciferase were generated using the pGL4.50 (luc2/CMV/Hygro) vector (Promega Corp) according to the manufacturers' protocol. 786-0 HRE and 786-0 CMV were seeded in 96-well plates and were screened according to the HRE-Luc assay protocol described in Example 2. Luciferase activity following compound treatment was determined using Steady Glo luciferase. Representative data are shown in FIG. 2, wherein A, B and C refer to treatments with KD02, KD007 and KD021 respectively. Filled circles indicate results from 786-0 HRE cells, whereas empty squares indicate results from 786-0 CMV cells. The ratios of CMV-Luc $IC_{50}$ to HRE-Luc $IC_{50}$ were 7.9, 4.75, and 2.6 for KD002, KD007 and KD007 respectively, suggesting that the decrease in HRE-Luc activity was unlikely to be caused by non-specific effects on luciferase.

Example 3

Western blots to determine impact of compounds on HIF-2α and cellular iron-sensing machinery.

Figure 3:
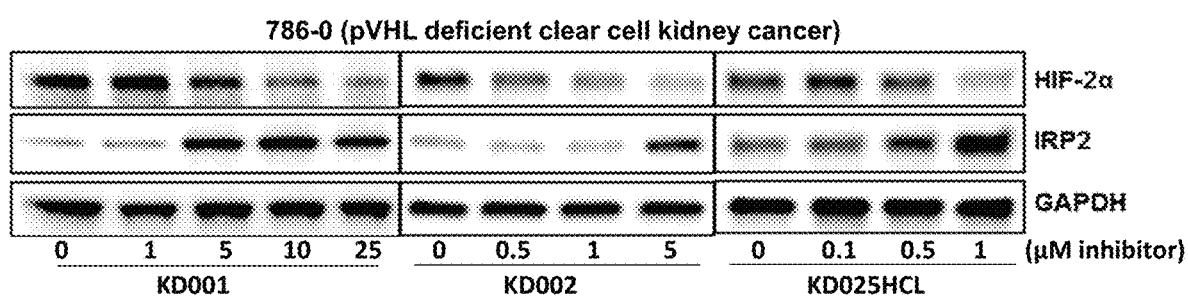
FIG. 3 shows a Western blot showing the impact of treatment of 786-0 CCRCC cells with KD001, KD002 or KD025HCl for 24 hours. Blots show that treatment with the compounds decreases HIF-2α and increases IRP2 relative to the loading control GAPDH. Since IRP2 is regulated by iron-mediated degradation, increased IRP2 may indicate iron-deficiency in cells.

Western blots were performed to determine the effects of the compounds on levels of HIF-2α and other relevant proteins. 786-0 (pVHL deficient clear cell kidney cancer cells) were purchased from ATCC were plated at 1×10E5 cells/well in 2 ml DMEM with 10% FBS/well in 6-well tissue culture plates. Cells were allowed to adhere overnight in a humidified incubator at 37° C. with 5% $CO_2$, after which the appropriate concentrations of compounds in DMSO were added. DMSO concentrations were kept constant in all wells. After 24 hour's exposure to the compounds, cells were lysed and subjected to western blotting according to standard protocols (Polek, Talpaz et al. 2003). Antibodies for HIF-2α and Glyceraldehyde 3-Phosphate Dehydrogenase (GAPDH) were purchased from Cell Signaling Technology (Danvers, Mass.), whereas antibodies to iron responsive element binding protein 2 (IRP2) and Glutathione Peroxidase 4 (GPX4) were from Santa Cruz Biotechnology (Dallas, Tex.) and R&D Systems, Inc (Minneapolis, Minn.). Representative data in FIG. 3 show a dose-dependent effect of compounds in decreasing HIF-2α. Compounds also impact cellular iron sensing given by increased IRP2, which taken together indicate that cells sense decreased amounts of available iron. Representative data shown in FIG. 5 Part C show a dose dependent effect of the compounds on GPX4, which may indicate decreased resistance to ferroptosis.

Example 4

Inductively coupled plasma mass spectrometry (ICP-MS) to determine impact of compounds on the concentration of iron and other transition metals in cancer cells.

Figure 4:
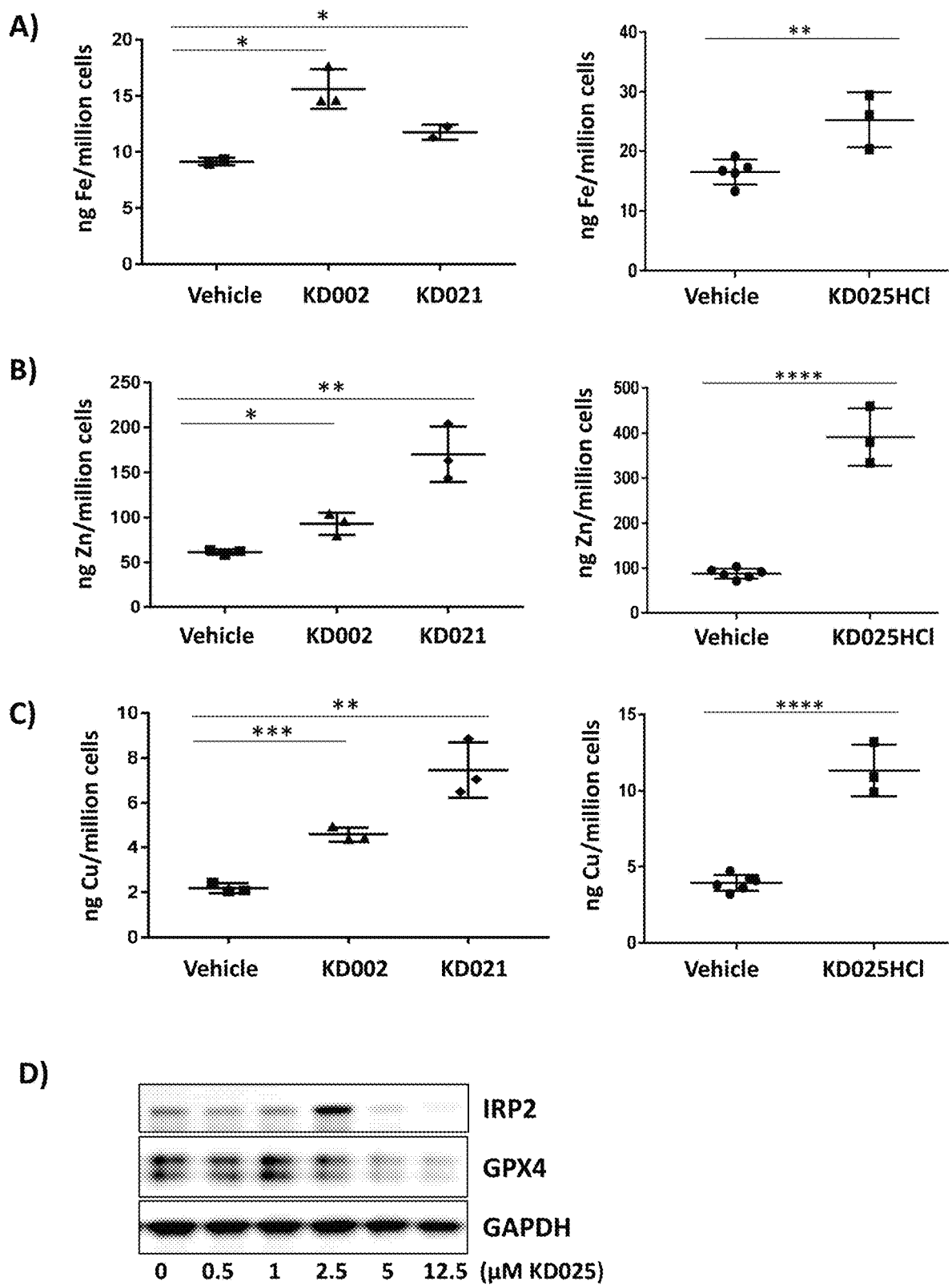
FIG. 4 shows the measurement of cellular iron (Fe), zinc (Zn) and copper (Cu) concentration (A, B and C respectively) using Inductively Coupled Plasma Mass Spectrometry (ICP-MS) in 786-0 CCRCC cells treated with vehicle (DMSO), 1.5 µM KD002 or KD021 for 24 hours (left panels), or in a separate experiment, vehicle (DMSO) or 2.5 µM KD025HCl (right panels). Error bars indicate standard error of the mean (SEM). Data show that treatment with these compounds increases the content of iron, zinc and copper in cells. Student's t-tests were performed to determine the significance of the differences between indicated groups: * indicates $p<0.05$, $p<0.01$, *$p<0.001$, ****p, 0.0001. Part D shows a western blot showing impact of treatment with higher concentrations of KD025HCl confirming a decrease in IRP2 and GPX4 consistent with increased iron content with higher concentrations of compound.

These studies were performed to determine the content of iron and other transition metals in cells after exposure the compounds described herein. 786-0 cells were seeded at 1.5 million cells/flask in T75 cm$^2$ flasks in DMEM+10% FBS, and allowed to adhere overnight. Cells were then treated with indicated concentrations of compounds in DMSO or DMSO alone (vehicle) for a further 24 hours, after which cells were detached by trypsinization, counted, washed twice in PBS and pelleted. Experiments were performed using three replicate T75 cm$^2$ flasks per condition. A 5:1 mixture of nitric acid (OPTIMA Grade, 70%, Fisher Scientific) and ultrapure hydrogen peroxide (ULTREX II, 30%, Fisher Scientific) was added to cell pellets. This mixture was allowed to digest overnight, heated until dry, and resuspended in 2% nitric acid for analysis using an Agilent 7900 ICP-MS (Agilent Technologies, Santa Clara, Calif.). Calibration standard solutions for determination of Fe were prepared from Agilent multi-element calibration standard-2A. An Agilent Environmental Calibration Standard was used as an independent control. PBS-only control digestions were used to measure background. Metal readings were normalized to cell number. Data obtained from these studies for three replicate readings (with SEM) are shown in FIG. 4, which show an increase in cellular iron (Fe) content after treatment with indicated compounds. The content of other transition metals such as zinc (Zn) and copper (Cu) were measured concurrently and were also significantly increased (*$p<0.05$; $p<0.01$; *$p<0.001$).

The findings from Example 3 (decreased cellular iron availability indicated by cellular iron sensing proteins) and Example 4 (increased total cellular iron content indicated by mass spectrometry), when taken together, suggest that compounds described herein induce an inability of cells to sense and/or utilize iron, which may contribute to, or occur in spite of, significantly elevated cellular iron levels.

Figure 5:
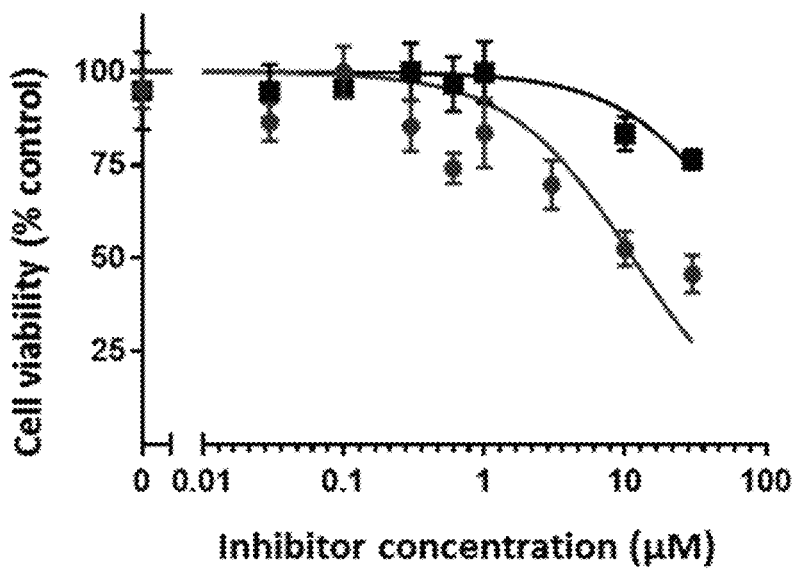
FIG. 5 Part A shows the effect of co-treatment of cells with compounds in the absence or presence of the iron chelator, desferoxiamine (DFO, 100 µM), which is also known to chelate other metals such as zinc and copper, to determine whether iron (or other metals) are involved in compound-mediated cell death. Part A shows an example plot of 786-0 CCRCC cells were treated with the KD021 (circles), or KD021+DFO (squares) for 24 hours, after which cell viability was measured using resazurin. Error bars indicate standard error of the mean (SEM). The concentration of KD021 required to decrease cell viability by 50% (cell viability $IC_{50}$) was 11.36 µM, and this $IC_{50}$ was increased to 83.63 µM when KD021 was added in the presence of DFO. Part B shows $IC_{50}$ values of additional compounds treated in the same manner, which show increased $IC_{50}$ values when cells were treated in the presence of DFO.
Figure 6:
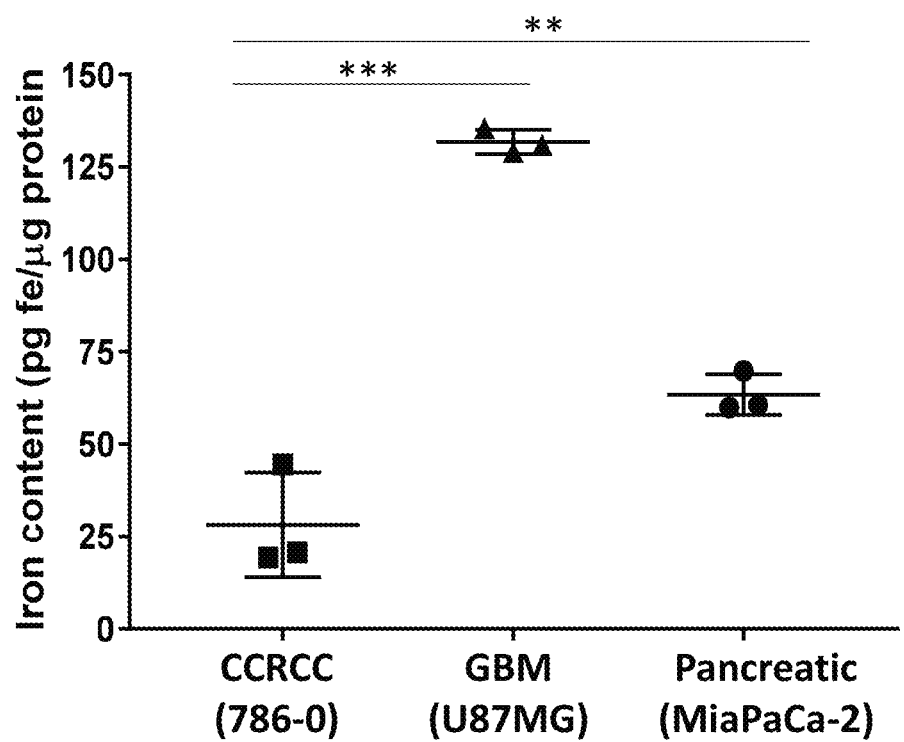
FIG. 6 shows the total iron content of cell lines from a variety of cancer types: 786-0 (CCRCC cells), U87MG (glioblastoma, GBM cells) and MIAPaCa-2 (pancreatic cancer cells) as determined by ICP-MS. Error bars indicate standard error of the mean (SEM). GBM and pancreatic cancer cells show significantly higher iron content per µg of protein compared to CCRCC.

To determine iron content in other cancer types, the same method described in Example 4 above was used to measure total iron content in untreated cell lines from a variety of cancer types: 786-0 (CCRCC cells), U87MG (glioblastoma, GBM cells) and MIAPaCa-2 (pancreatic cancer cells). GBM and pancreatic cancer cells showed significantly highly iron content per mg of protein compared to CCRCC (FIG. 5). This suggests that these other cancer types may also be susceptible to ferroptosis induced by the compounds described herein.

Example 5

Iron chelation as a method to ameliorate compound-mediated toxicity and confirm ferroptosis as the mechanism of compound-mediated cell death.

In view of the increased cellular iron concentrations induced by the compounds described herein, the involvement of iron in mediating cell death was determined. Cell viability assays were performed as described in Example 2 using resazurin as a cell viability readout, and performed in the absence or presence of 100 μM of the iron chelator, deferoxamine (D9533, MilliporeSigma, St Louis, Mo.). Representative results are shown in FIG. 5 Parts A and B. The concentration of KD021 required to decrease cell viability by 50% (cell viability $IC_{50}$) was 11.36 μM, and this $IC_{50}$ was increased to 83.63 μM when KD021 was added in the presence of deferoxamine. Similar protective effects of DFO were also observed with other compounds KD002 and KD025. The data support an iron-dependent mechanism of cell death, or feroptosis.

Example 6

Thermal shift assays to validate iron-sulfur cluster assembly 2 (ISCA2) as the molecular target of the compounds described herein.

Figure 7:
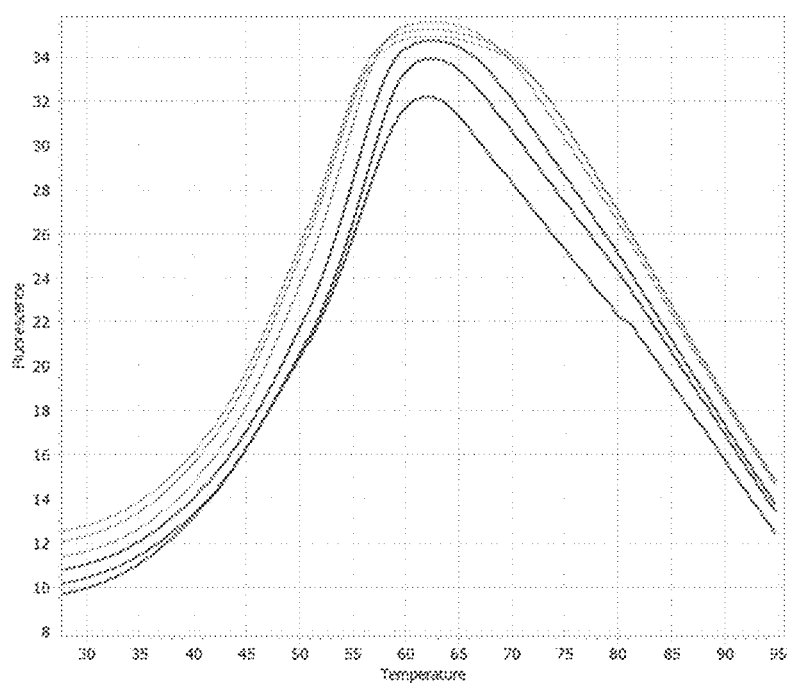
FIGS. 7 and 8 show findings of the thermal shift assay using recombinant ISCA2 and 200 µM of KD001 or 100 µM of KD025 respectively. Part A in these figures show the changes in fluorescence with increasing temperature in control (grey traces), or treated (black traces) wells. Part B show the ratio of changes in fluorescence (dF) with changes in temperature (dT), given by dF/dT, the peak of which indicates the melting temperature of ISCA2 under these assay conditions. For KD001 in FIG. 7, the average Tm readings for control wells was 53.21±0.36° C. (replicate readings were 53.92, 52.83, 52.90), whereas Tm readings for KD001-treated wells were 55.63±0.26° C. (replicate readings were 55.10, 55.92, 55.96), giving a change in melting temperature of ISCA2 ($dT_m$) of 2.41±0.44° C., with a Student's t-test p-value of 0.005. For KD025 in FIG. 8, the average Tm readings for control wells was 55.02±0.2° C. (replicate readings were 55.42, 54.83, 54.81), whereas Tm readings for KD025-treated wells were 56.3±0.02° C. (replicate readings were 56.33, 56.3, 56.27), giving a change in melting temperature of ISCA2 ($dT_m$) of 1.21±0.20° C., with a Student's t-test p-value of 0.003.
Figure 7:
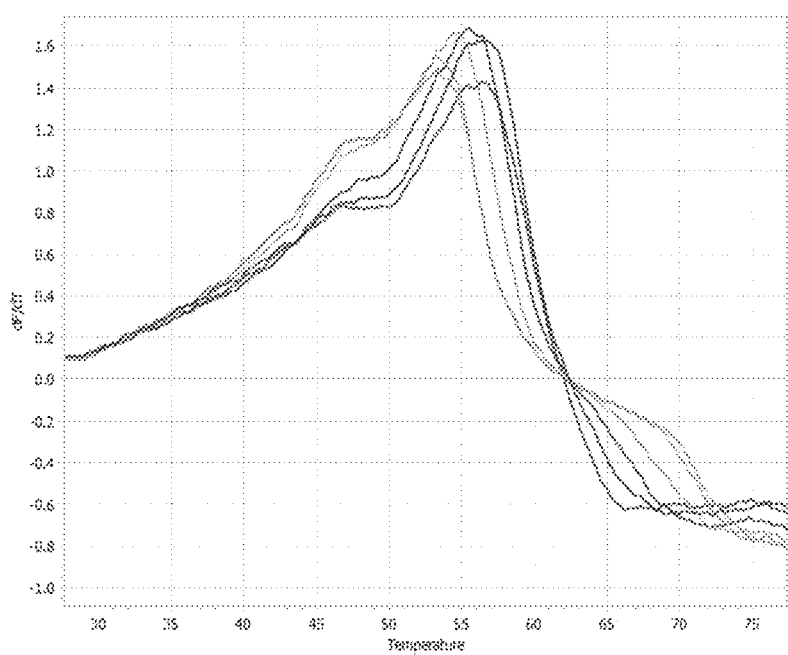
Figure 8:
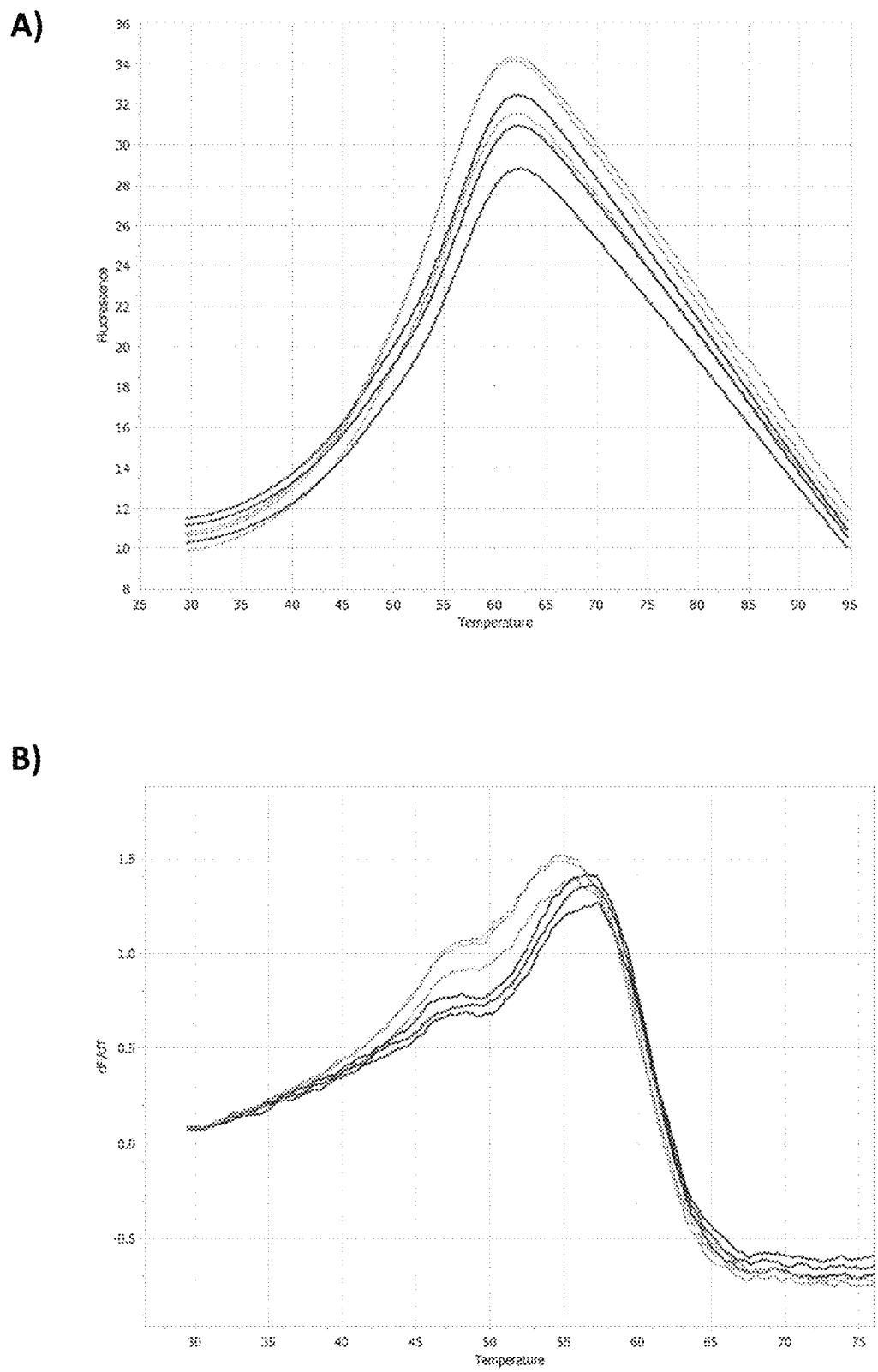

Thermal shift assays were performed by monitoring the change in protein melting temperature (Tm) in the absence or presence of test compounds, using the hydrophobic protein binding dye, SYPRO Orange (S6650, Thermo Fisher Scientific, Waltham, Mass.), measured using the LightCycler 480 (Roche Life Sciences, Indianapolis, Ind.) according to the manufacturer's protocol. Recombinant ISCA2 was produced by expressing amino acid residues 9-154 of ISCA2 (ISCA2 lacking its mitochondrial localization sequence) in the pET28 vector containing an N-terminal His6 tag in Rosetta (DE3) competent cells (Novagen, Millipore Sigma). ISCA2 production was induced by treating ISCA2 transformed log phase cells with 0.25 mM IPTG for 4 hours at 18° C. ISCA2 was purified using $Ni^{2+}$ affinity purification according to standard protocols and eluted in 50 mM Tris-Cl pH7.4, 150 mM NaCl, 5 mM DTT. Thermal shift assays were performed in 384-well plates using 1 μl of a 10× concentration of SYPRO Orange, 8 μl of ISCA2 (4 μg protein) and 1 μl of 1-2 mM stock of test compound per well. The LightCycler was used according to the following setup: LightCycler 480 Instrument Temperature Setup: First target of 20° C., with a Hold of 15 seconds; second target of 95° C., with Acquisition Mode of Continuous, and 10 acquisitions per degree C.; and third target of 20° C., with a Hold of 15 seconds. $T_m$s were determined using Roche Protein Melting Analysis Software. Representative data are shown in FIGS. 7 and 8 using KD001 at 200 μM final concentration and KD025 at 100 μM final concentration respectively. Part A in these figures show the changes in fluorescence with increasing temperature in control (grey traces), or treated (black traces) wells. Part B show the ratio of changes in fluorescence (dF) with changes in temperature (dT), given by dF/dT, the peak of which indicates the melting temperature of ISCA2 under these assay conditions. In these examples, for KD001 in FIG. 7, the average Tm readings for control wells was 53.21±0.36° C. (replicate readings were 53.92, 52.83, 52.90), whereas Tm readings for KD001-treated wells were 55.63±0.26° C. (replicate readings were 55.10, 55.92, 55.96). Thus, treatment with KD001 results in a change in melting temperature of ISCA2 ($dT_m$) of 2.41±0.44° C., with a Student's t-test p-value of 0.005. For KD025 in FIG. 8, the average Tm readings for control wells was 55.02±0.2° C. (replicate readings were 55.42, 54.83, 54.81), whereas Tm readings for KD025-treated wells were 56.3±0.02° C. (replicate readings were 56.33, 56.3, 56.27). Thus, treatment with KD025 results in a change in melting temperature of ISCA2 (dT$_m$) of 1.21±0.20° C., with a Student's t-test p-value of 0.003. Taken together, the data suggest that ISCA2 is the molecular target of the described compounds.

Example 7

Use of compounds to inhibit the growth cancer cells in vivo.

Figure 9:
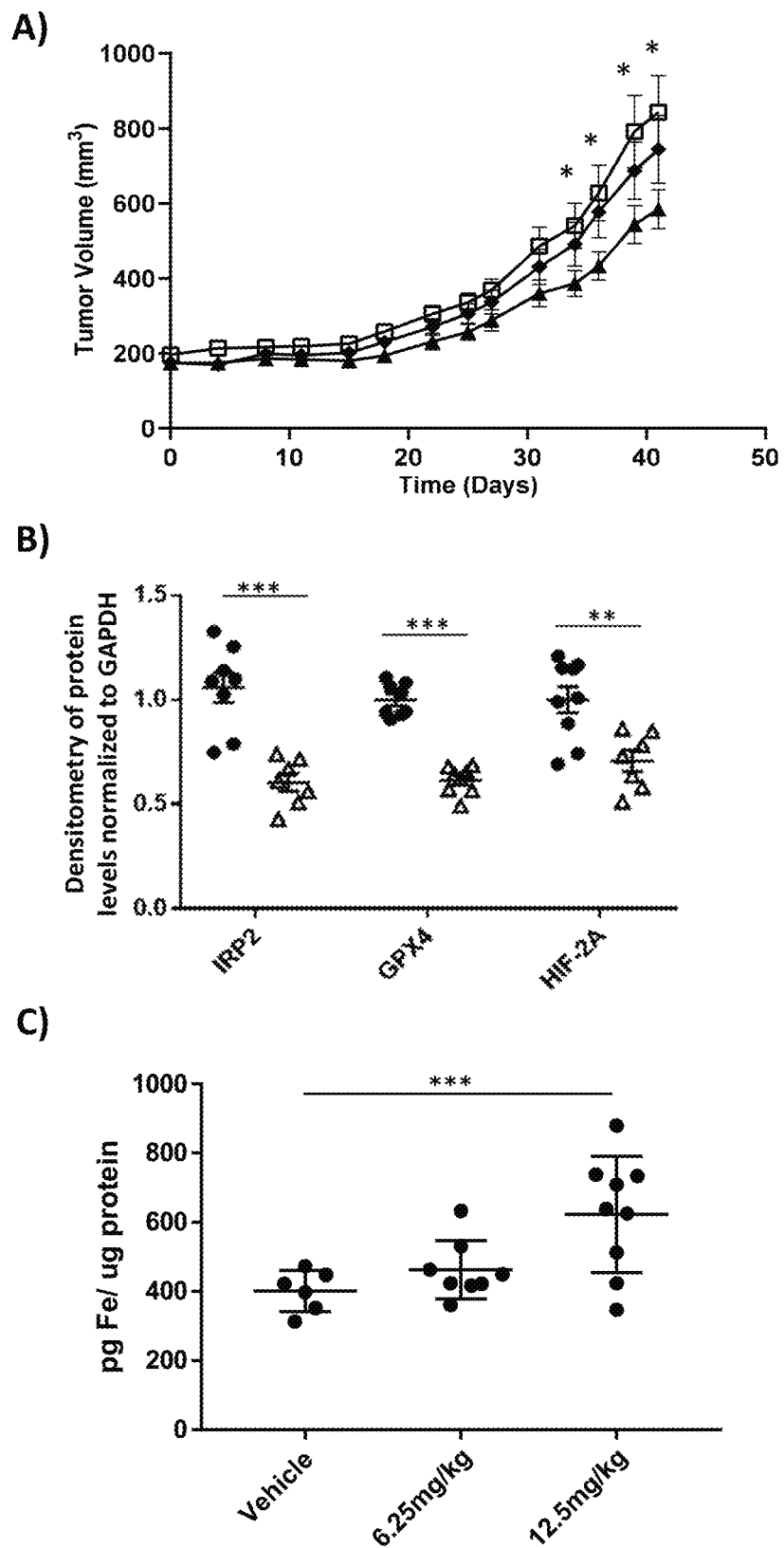
FIG. 9 shows the effect of treatment with vehicle (open squares; 12 mice/group), 6.25 mg/kg (filled diamonds; 13 mice/group) or 12.5 mg/kg (filled triangles; 14 mice/group) KD025HCl twice daily (mice dosed 8 am and 4 pm) on the growth of 786-0 CCRCC human tumor xenografts in immune-deficient mice. Error bars indicate standard error of the mean (SEM). Part A shows the effect of treatment on average tumor size over time (treatment started on Day 0). Part B shows the effects of treatment with vehicle (filled circles) or 12.5 mg/kg KD025HCl (open triangles) on protein levels of IRP2, GPX4 and HIF-2α relative to the loading control, GAPDH, as determined by densitometric analysis of western blots from tumors harvested at the end of the study. Part C shows the tumor iron content from mice treated with vehicle, 6.25 mg/kg or 12.5 mg/kg KD025HCL as shown in Part A as determined by ICP-MS. For parts B and C, each data point represents a tumor from an individual mouse. In Parts A, B and C, Student's t-tests were performed to compare vehicle and 12.5 mg/kg KD025HCL treated mice. * indicates $p<0.05$, $p<0.01$, *$p<0.001$.
Figure 10:
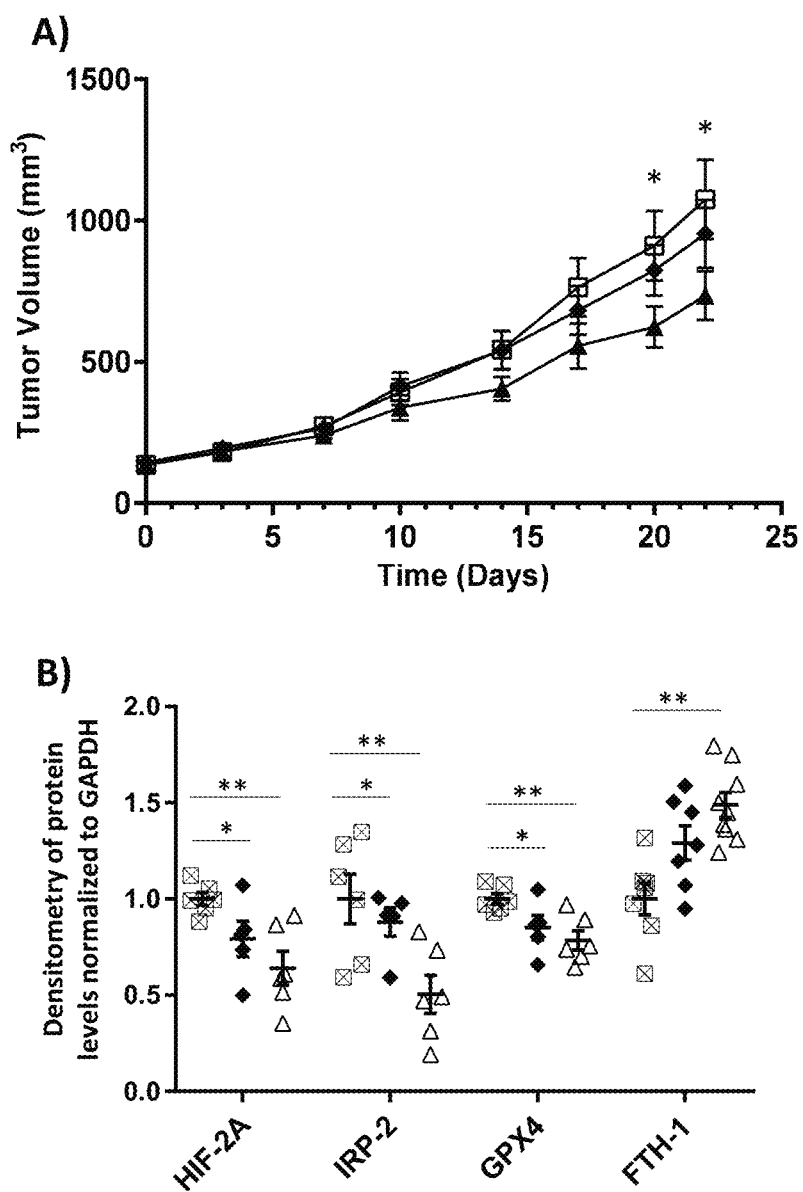
FIG. 10 shows the effect of treatment with vehicle (open squares; 8 mice/group), 35 mg/kg (filled diamonds; 10 mice/group) or 70 mg/kg (filled triangles; 8 mice/group) KD025HCl once daily on the growth of 786-0 CCRCC human tumor xenografts in immunodeficient mice. Error bars indicate standard error of the mean (SEM). Part A shows the effect of treatment on average tumor size over time (treatment started on Day 0). Part B shows the effects of treatment with vehicle (crossed squares), 35 mg/kg (filled diamonds) or 70 mg/kg KD025HCl (open triangles) on tumor protein levels of IRP2, GPX4, HIF-2α and FTH1 relative to the loading control, GAPDH as determined by densitometric analysis of western blots from tumors harvested at the end of the study. Each data point represents a tumor from an individual mouse. Student's t-tests were performed to compare vehicle and 12.5 mg/kg KD025HCL treated mice. * indicates $p<0.05$, $p<0.01$, *$p<0.001$.

Based on the ability of the compounds to inhibit both HIF-2α and promote ferroptosis, these compounds would be of use for blocking tumor growth in animals. To asses this using mouse models of kidney cancer, subcutaneous tumors were derived from 786-0 cells purchased from ATCC. Subcutaneous tumors were established by injection of 5 million cells subcutaneously into the flank of male immunodeficient NRG mice in 100 µl volume of a 1:1 ratio of DMEM and growth factor reduced Matrigel (Corning Life Sciences, Tewksbury Mass.). Once tumors attained an average tumor size of approximately 150 mm3, mice were stratified into compound- or vehicle-treated groups of equal initial average tumor burden (8-15 mice per group), and treatment was initiated. In the example shown in FIG. 9, mice were treated orally with vehicle, 6.25 mg/kg or 12.5 mg/kg KD025 in a vehicle of 0.5% methyl cellulose and 1% Tween 80 in ultra-pure distilled water, twice per day at 8 am and 4 pm. Maximum volume administered was 200 µl in a 30 g mouse. In FIG. 10, mice were treated with vehicle, 35 mg/kg or 70 mg/kg KD025 in the same vehicle once per day. Mice were treated until tumors reached approximately 1,500 mm$^3$, or required euthanasia (according to institutional animal care and use protocols), whichever occurred sooner. Mouse tumor volumes were measured twice weekly. Mice were cheek bled on a rotating schedule to ensure each mouse was bled at most twice throughout the entire study once weekly to determine serum plasma concentrations of compounds. At the end of the study, mice were euthanized and tumors harvested to determine treatment effects on levels of HIF-2α, GPX4 and cellular iron. To detect tumor levels of HIF-2α and GPX4, flash-frozen tumor sections were homogenized in lysis buffer and subjected to western blotting, as described in Example 3. Western blot bands intensities for the relevant proteins were determined by densitometry of gel images, and relative intensities were determined by normalizing data to a loading control such as GAPDH. These values were presented as a ratio to the average values obtained in vehicle-treated mice and are shown in FIG. 9 Panel B and FIG. 10 Panel B. For determination of cellular iron levels within the tumor, flash-frozen tumor samples were subjected to ICP-MS as described in Example 4, and are shown in FIG. 9 Part C and FIG. 10 Part C.

Figure 11:
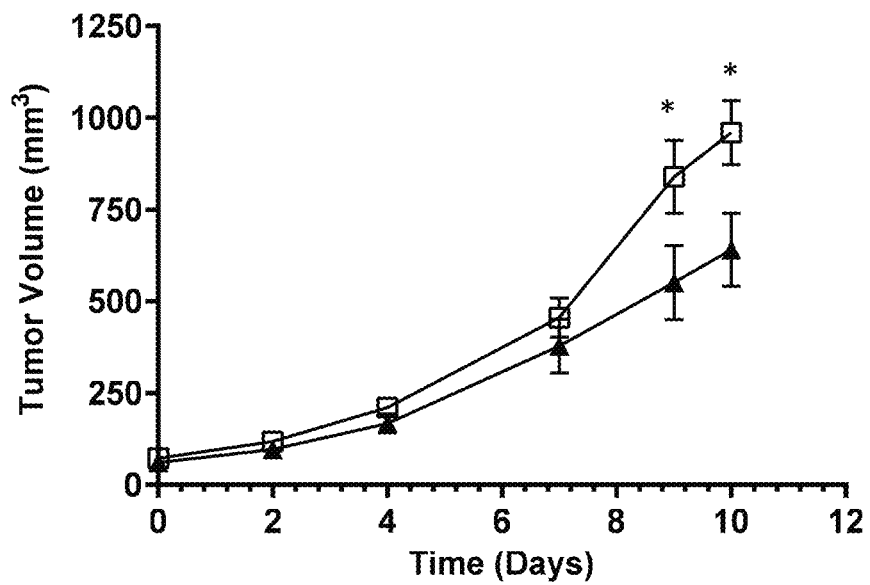
FIG. 11 shows the effect of treatment with vehicle (open squares; 9 mice/group), or 70 mg/kg (filled triangles; 7 mice/group) KD025HCl twice daily on the growth of RENCA syngeneic tumors in immunocompetent Balb/c mice. Error bars indicate standard error of the mean (SEM). The chart shows the effect of treatment on average tumor size over time (treatment started on Day 0). Student's t-tests were performed to compare vehicle and KD025HCL treated mice. * indicates $p<0.05$ FIG. 12 Part A shows the plasma levels of KD025HCl after indicated days of oral administration of 6.25 mg/kg (filled triangles) or 12.5 mg/kg (open squares) of KD025HCl twice daily (8 am and 4 pm) into tumor-bearing non-fasted immune-deficient NRG mice. Treatment was initiated on day 1 and mice were bled 7 hours (trough concentrations) after treatment on the indicated days. Each data point refers to data from one mouse. Error bars indicate standard error of the mean (SEM). Part B shows average plasma values (ng/ml) for the indicated doses of KD025HCl.
Figure 12:
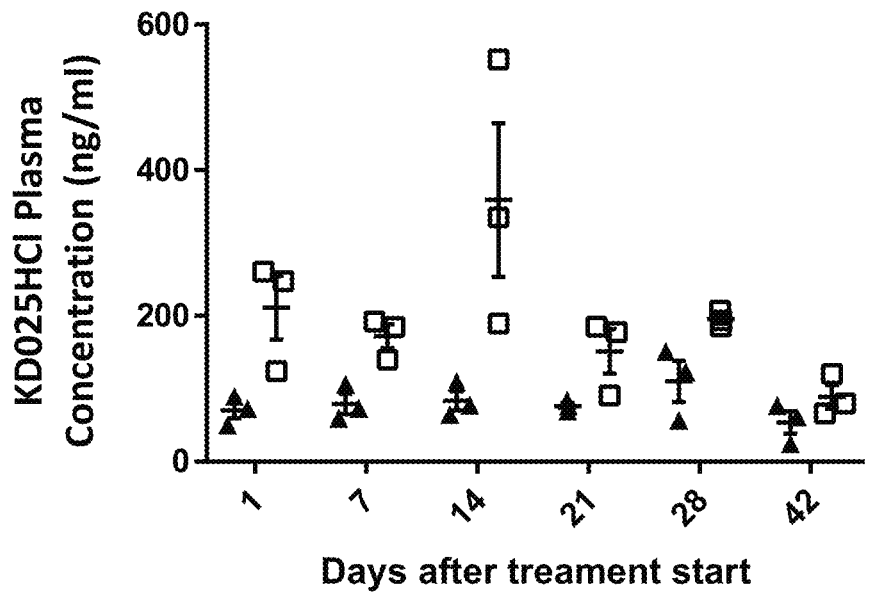

A similar study was also performed using RENCA cells, which are derived from a renal tumor that arose spontaneously in a male Balb/c mouse (Murphy and Hrushesky 1973). RENCA cells were purchased from ATCC and, 2 million cells were implanted into the flanks of Balb/c mice. Once tumors attained an average size of approximately 75 mm$^3$, mice were stratified into two groups and animals treated with either vehicle or 70 mg/kg KD025 once daily PO. Mouse tumor volumes were measured three times a week until tumors reached approximately 1000 mm$^3$, or mice required euthanasia. Data obtained from this study is showed in FIG. 11.

Example 8

Bioanalysis of compound concentration in serum using LC/MS/MS.

Bioanalysis was performed on plasma from mice treated with KD025HCL to determine levels of KD025HCl present in mouse plasma. To prepare a standard cure, a Primary stock solution of Kuda-025 HCl was prepared in DMSO at 1.4 mg/mL. After correction for salt content, the Primary solution was used to prepare a Secondary Stock solution at 0.5 mg/mL in 100% Acetonitrile based on the molecular weights (MW) and formula weights (FW) of KD025HCl at MW=368, FW=404.46. Primary and Secondary Stock solutions of Kuda-033 were prepared in a similar manner for use as an internal standard based on KD033 MW=356.32.

For standard curve preparation, 10× concentration, standard curve spiking solutions were prepared in Acetonitrile using the Secondary Stock solution to prepare a 20.48 mg/mL High standard spiking solution. The High standard was diluted serially by half-step concentrations down to 10 ng/mL so that the 10× spiking solutions were 10, 20, 40, 80, 160, 320, 640, 1280, 2560, 5120, 10240 and 20480 ng/mL. Standard curves, run before and after samples, were prepared at 1× concentration by spiking 5 mL of each 10× spiking solution into 45 mL of blank mouse plasma with final concentrations 1/10$^{th}$ of the above spiking solution concentrations.

Samples and standard curve samples were extracted using a liquid-liquid method. Briefly, 1 mL MTBE, 0.5 mL of 0.1% Formic Acid and 1 mL Acetonitrile, fortified with KD033 as internal standard, were added to 50 mL aliquots of sample (and curve samples) in a 13×100 mm borosilicate glass test tube. This mixture was vortexed vigorously and centrifuged at 5000×g. The upper, organic layer was transferred to a new 13×100 mm tube and dried at 40° C. under a stream of air. Samples were then reconstituted in 200 mL of 50/50 AcN/H$_2$O and analyzed by mass spectrometry.

For LC/MS/MS, a ThermoFinnigan TSQ Quantum mass spectrometer was used with precursor/product ions: KD025 m/z 369.06→178.96; Kuda-033 m/z 357.08→190.9. Sample concentrations were determined using compound/internal standard ratios against a 1/xweighted, quadratic fit, sample curve. The column used was Gemini-NX C18, 3 mm particle size, Length 50 mm, ID 2.1 mm. LC conditions used were Isocratic with Mobile Phase A: AcN, 01.% Formic Acid 50%; Mobile Phase B: 0.1% Formic Acid 500% and Flow Rate 0.3. An example of a standard curve prepared in this manner is shown below:

TABLE 2

Standard Curve for KD025HCl concentration in mouse plasma

| Sample ID | KD025 (ng/ml) | |
|---|---|---|
| (conc-replicate) | Expected Amount | Calculated Amount |
| 1-1 | 1.000 | 1.764 |
| 2-1 | 2.000 | 2.633 |
| 4-1 | 4.000 | 5.699 |
| 8-1 | 8.000 | 7.998 |
| 16-1 | 16.000 | 13.801 |
| 32-1 | 32.000 | 30.568 |
| 64-1 | 64.000 | 70.493 |
| 128-1 | 128.000 | 105.943 |
| 256-1 | 256.000 | 246.604 |
| 512-1 | 512.000 | 393.534 |
| 1024-1 | 1024.000 | 1137.400 |
| 2048-1 | 2048.000 | 1771.408 |

TABLE 2-continued

Standard Curve for KD025HCl concentration in mouse plasma

| Sample ID (conc-replicate) | KD025 (ng/ml) | |
|---|---|---|
| | Expected Amount | Calculated Amount |
| 1-2 | 1.000 | 1.693 |
| 2-2 | 2.000 | 2.682 |
| 4-2 | 4.000 | 5.705 |
| 8-2 | 8.000 | 9.892 |
| 16-2 | 16.000 | 14.052 |
| 32-2 | 32.000 | 30.952 |
| 64-2 | 64.000 | 68.772 |
| 128-2 | 128.000 | 129.492 |
| 256-2 | 256.000 | 299.392 |
| 512-2 | 512.000 | 605.980 |
| 1024-2 | 1024.000 | 922.161 |
| 2048-2 | 2048.000 | 1866.391 |

Equation: $Y = -0.00346534 + 0.00471517 * X - 5.47591e-007 * X^2$ $R^2 = 0.9801$

Example 9

Bioavailability determination of KD025HCl in mice.

To determine the bioavailability KD025HCl, serum concentrations of KD025HCl were determined after varying durations following oral or intravenous (IV) administration. Doses were validated by LC/MS/MS.

For IV administration, 264 µl of N-Methyl-2-Pyrrolidone (NMP) was added to 1.221 mg of KD025HCl, and the solution vortexed and sonicated until complete dissolution. Then, 2.374 ml of 10% (v/v) solutol in water for injection was added, and the solution vortexed, then sonicated with a bath sonicator. The final dosing formulation of a brownish colored clear solution. A single 2 mg/kg dose (5 ml/kg) was administered IV each to nine male Swiss albino mice. Blood plasma was obtained after indicated time periods as shown in Table 3.

TABLE 3

Mouse Dosing and Sample Collection (IV administration)

| Time Point (hr) | Group No. | Animal No. | Body Wt. (g) | Dose of Test Item (mL) | Time of Dosing (hr) | Time for Sample collection (hr) |
|---|---|---|---|---|---|---|
| 0.08 | 1 | M1 | 31.02 | 0.16 | 10:29 | 10:34 |
| | | M2 | 32.30 | 0.16 | 10:31 | 10:36 |
| | | M3 | 28.71 | 0.14 | 10:33 | 10:38 |
| | | — | — | — | — | — |
| 1 | | — | — | — | — | 11:29 |
| | | — | — | — | — | 11:31 |
| | | — | — | — | — | 11:33 |
| | | — | — | — | — | — |
| 0.25 | 2 | M4 | 31.11 | 0.16 | 10:23 | 10:38 |
| | | M5 | 32.70 | 0.16 | 10:25 | 10:40 |
| | | M6 | 32.17 | 0.16 | 10:27 | 10:42 |
| | | — | — | — | — | — |
| 2 | | — | — | — | — | 12:23 |
| | | — | — | — | — | 12:25 |
| | | — | — | — | — | 12:27 |
| | | — | — | — | — | — |
| 4 | | — | — | — | — | 14:23 |
| | | — | — | — | — | 14:25 |
| | | — | — | — | — | 14:27 |
| | | — | — | — | — | — |
| 0.5 | 3 | M7 | 28.29 | 0.14 | 10:17 | 10:47 |
| | | M8 | 29.18 | 0.15 | 10:19 | 10:49 |
| | | M9 | 33.58 | 0.17 | 10:21 | 10:51 |
| | | — | — | — | — | — |
| 8 | | — | — | — | — | 18:17 |
| | | — | — | — | — | 18:19 |
| | | — | — | — | — | 18:21 |
| 24 | | — | — | — | — | 10:17 |
| | | — | — | — | — | 10:19 |
| | | — | — | — | — | 10:21 |
| | | — | — | — | — | — |

For oral administration (PO), 29 dt of Tween-80 was added to 3.38 mg of KD025HCl, triturated, then 2.893 ml of 0.5% methyl cellulose was added in parts with continuous trituration then vortexed. The final dosing formulation was a brownish colored clear solution. A single 10 mg/kg dose (10 ml/kg) was administered PO each to nine male Swiss albino mice. Tissue (blood plasma and brain) was harvested after indicated time periods as shown in Table 4.

TABLE 4

Mouse Dosing and Sample Collection (PO administration)

| Time Point (hr) | Group No. | Animal No. | Body Wt. (g) | Dose of Test Item (mL) | Time of Dosing (hr) | Time for Sample collection (hr) |
|---|---|---|---|---|---|---|
| 0.25 | 1 | M1 | 25.54 | 0.26 | 10:20 | 10:35 |
| | | M2 | 25.39 | 0.25 | 10:22 | 10:37 |
| | | M3 | 23.44 | 0.23 | 10:24 | 10:39 |
| | | — | — | — | — | — |
| 1 | | — | — | — | — | 11:20 |
| | | — | — | — | — | 11:22 |
| | | — | — | — | — | 11:24 |
| | | — | — | — | — | — |
| 0.5 | 2 | M4 | 24.31 | 0.24 | 10:14 | 10:44 |
| | | 5 | 26.22 | 0.26 | 10:16 | 10:46 |
| | | M6 | 23.89 | 0.24 | 10:18 | 10:48 |
| | | — | — | — | — | — |
| 2 | | — | — | — | — | 12:14 |
| | | — | — | — | — | 12:16 |
| | | — | — | — | — | 12:18 |
| | | — | — | — | — | — |
| 6 | | — | — | — | — | 16:14 |
| | | — | — | — | — | 16:16 |
| | | — | — | — | — | 16:18 |
| | | — | — | — | — | — |
| 4 | 3 | M7 | 24.33 | 0.24 | 10:08 | 14:08 |
| | | M8 | 24.10 | 0.24 | 10:10 | 14:10 |
| | | M9 | 25.01 | 0.25 | 10:12 | 14:12 |
| | | — | — | — | — | — |
| 8 | | — | — | — | — | 18:08 |
| | | — | — | — | — | 18:10 |
| | | — | — | — | — | 18:12 |
| | | — | — | — | — | — |
| 24 | | — | — | — | — | 10:08 |
| | | — | — | — | — | 10:10 |
| | | — | — | — | — | 10:12 |
| | | — | — | — | — | — |

The bioanalysis procedure is summarized in Table 5. Calibration Curve & QC preparation: 2.0 µl of calibration curve standards were added to 48Pl of blank matrix and precipitated with 200 µl of Acetonitrile containing an internal standard at 200 ng/ml. The solution was vortexed for 5 min at 850 rpm, then centrifuged at 4000 rpm for 5 min at 4° C. 110 µl of the supernatant was obtained and diluted with 130 µl of (Methanol:water, 1:1 v/v). Sample Preparation: 50 µl of sample was precipitated with 200 µl of Acetonitrile containing the internal standard at 200 ng/ml. The mixture was vortexed for 5 min at 850 rpm, then centrifuged at 4000 rpm for 5 min at 4° C. 110 µL of supernatant was obtained and diluted with 130 µL of (Methanol:water, 1:1 v/v).

TABLE 5

| | Compound Details and Bioanalysis Protocol | | | | |
|---|---|---|---|---|---|
| | Name of Compound | Molecular weight Free Form | Molecular weight Salt Form | Purity/ potency/ assay | Diluents-Master stock preparation |
| Analyte | KD-025HCl | 368.25 | 404.81 | >95 | DMSO |
| Internal Standard | Telmisartan | 514.60 | 514.60 | 98% | DMSO |

| CHROMATOGRAPHY: LC gradient | | |
|---|---|---|
| Time (min) | % A | % B |
| 0.00 | 95 | 5 |
| 1.00 | 5 | 95 |
| 2.50 | 5 | 95 |
| 2.60 | 95 | 5 |
| 3.50 | 95 | 5 |

| | |
|---|---|
| Mobile Phase (A) | 10 mM Ammonium Acetate with 0.1% Formic acid in water |
| Mobile Phase (B) | ACETONITRILE:METHANOL(50:50) |
| Column | Phenomenex, Kinetex EVO C18 4.5 * 50 mm, 5 μ |
| Injection Volume (μL) | 5 |
| Flow Rate (mL/min) | 1 |
| Run Time (min) | 3.5 |
| Sample Cooler Temperature (°C.) | 15 |
| Column Oven Temperature (°C.) | 40 |
| Rinsing Solution | Acetonirile:Methanol: water::20:60:20,V//V |
| Ionization Mode-Polarity | ESI-positive |

| | | Retention | MRM Transitions | | Declustering | Entrance | Collision |
|---|---|---|---|---|---|---|---|
| | Name of Compound | Time (Min) | Q1-mass | Q3-mass | Potential (DP) | Potential (EP) | Energy (CE) |
| Analyte | RD-025 | 1.43 | 369.30 | 179.10 | 81 | 10 | 32 |
| Internal Standard | Telmisartan | 1.86 | 515.40 | 276.10 | 60 | 10 | 60 |

| | |
|---|---|
| Collision Cell Exit Potential (CXP) | 12 |
| Collision Gas (CAD) | 8 |
| Curtain Gas (CUR) | 30 |
| Nebulizer Gas (GS1) | 50 |
| Heater Gas (GS2) | 50 |
| Ion spray voltage (V) | 5500 |
| Temperature (TEM) | 500 |
| Interface Heater (ihe) | ON |

Figure 13:
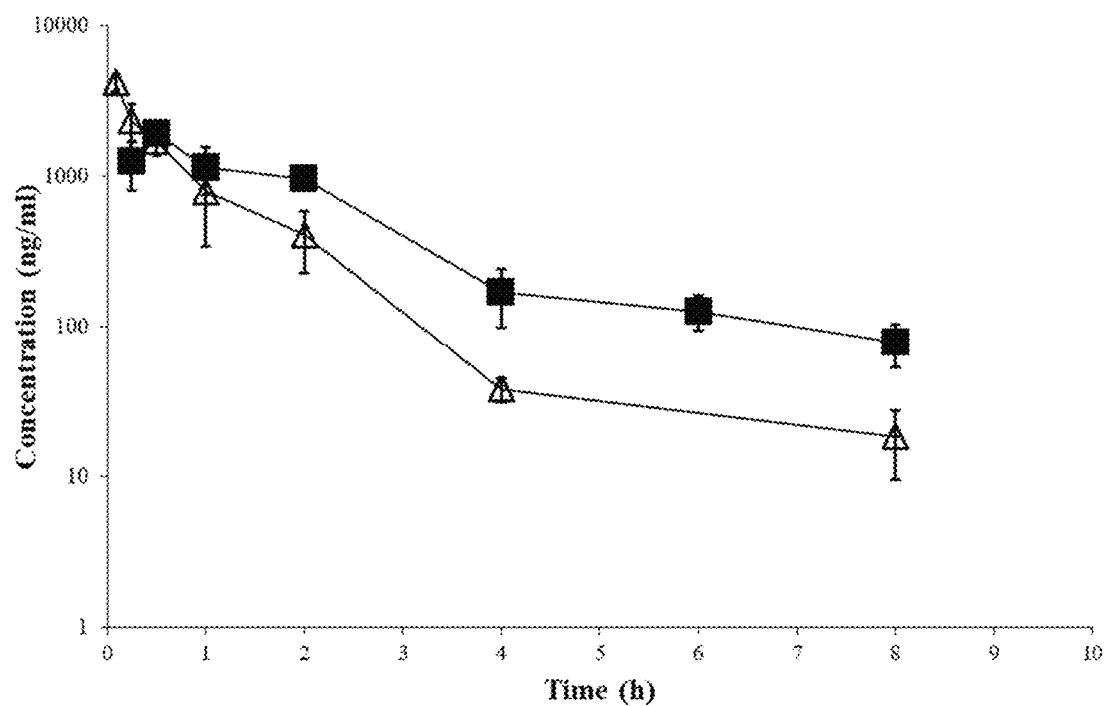
FIG. 13 shows the plasma levels of KD025HCl after a single oral administration (10 mg/kg; filled squares) or intravenous administration (2 mg/kg; unfilled triangles) at time 0. Results are the average of 3 mice/time point with error bars indicated standard deviation.

Using this procedure, the plasma levels of KD025HCl after either IV or PO administration was determined, and bioavailability as well as other pharmacokinetic parameters were determined and shown in Table 6. The plot of plasma concentration versus time is shown in FIG. 13.

TABLE 6

Plasma levels of KD025HCl after PO or IV administration in Swiss Albino mice.

| | M1- | M2- | M3- | Mean | Std Dev | % CV |
|---|---|---|---|---|---|---|
| Plasma concentrations (ng/mL) after IV (2.00 mg/kg) dose administration | | | | | | |
| Time (h) | | | | | | |
| 0.08 | 4792.21 | 3949.80 | 3776.46 | 4172.82 | 543.36 | 13.02 |
| 0.25 | 1863.08 | 2069.26 | 3078.66 | 2337.00 | 650.52 | 27.84 |
| 0.50 | 1482.12 | 1527.09 | 2079.24 | 1696.15 | 332.53 | 19.61 |
| 1.00 | 282.26 | 11135.53 | 952.05 | 789.94 | 449.14 | 56.86 |
| 2.00 | 277.23 | 334.05 | 611.15 | 407.47 | 178.66 | 43.85 |
| 4.00 | 37.24 | 31.51 | 45.40 | 38.05 | 6.98 | 18.35 |
| 8.00 | 11.09 | 28.55 | 16.02 | 18.55 | 9.00 | 48.54 |
| 24.00 | BLQ | BLQ | BLQ | BLQ | NC | NC |
| Dose (mg/kg) | 2.00 | 2.00 | 2.00 | 2.00 | 0.00 | 0.00 |
| Co(ng/mL) | — | — | — | 5481.64 | — | — |
| $t_{1/2}$ (h) | — | — | — | 1.31 | — | — |
| Vss (L/kg) | — | — | — | 0.72 | — | — |

TABLE 6-continued

Plasma levels of KD025HCl after PO or IV administration in Swiss Albino mice.

|  | M1- | M2- | M3- | Mean | Std Dev | % CV |
|---|---|---|---|---|---|---|
| Vd (L/kg) | — | — | — | 1.24 | — | — |
| Cl (mL/min/kg) | — | — | — | 10.94 | — | — |
| $AUC_{0\text{-}last}$ (ng · h/mL) | — | — | — | 3012.90 | — | — |
| $AUC_{0\text{-}inf}$ (ng · h/mL) | — | — | — | 3047.99 | — | — |
| $AUC_{Extra}$ (%) | — | — | — | 1.15 | — | — |
| $MRT_{0\text{-}last}$ (h) | — | — | — | 0.99 | — | — |
| Rsq | — | — | — | 0.9989 | — | — |
| Plasma concentrations (ng/mL) after PO (10.00 mg/kg) dose administration | | | | | | |
| Time (h) | | | | | | |
| 0.25 | 1609.45 | 742.75 | 1428.60 | 1260.27 | 457.21 | 36.28 |
| 0.50 | 1969.66 | 1712.09 | 2056.44 | 1912.73 | 179.09 | 9.36 |
| 1.00 | 1568.37 | 784.84 | 1081.06 | 1144.76 | 395.63 | 34.56 |
| 2.00 | 944.99 | 861.31 | 1052.53 | 952.95 | 95.86 | 10.06 |
| 4.00 | 179.52 | 94.08 | 235.20 | 169.60 | 71.08 | 41.91 |
| 6.00 | 160.48 | 93.52 | 126.29 | 126.76 | 33.48 | 26.41 |
| 8.00 | 85.47 | 50.78 | 99.61 | 78.62 | 25.13 | 31.96 |
| 24.00 | 1.79* | BLQ | BLQ | BLQ | NC | NC |
| Dose (mg/kg) | 10.00 | 10.00 | 10.00 | 10.00 | 0.00 | 0.00 |
| Cmax (ng/mL) | — | — | — | 1912.73 | — | — |
| $T_{max}$ (h) | — | — | — | 0.50 | — | — |
| $T_{1/2}$ (h) | — | — | — | 3.61 | — | — |
| $AUC_{0\text{-}last}$ (ng · h/mL) | — | — | — | 3751.58 | — | — |
| $AUC_{0\text{-}inf}$ (ng · h/mL) | — | — | — | 4160.64 | — | — |
| $AUC_{Extra}$ (%) | — | — | — | 9.83 | — | — |
| $MRT_{0\text{-}last}$ (h) | — | — | — | 2.03 | — | — |
| Rsq. | — | — | — | 0.98 | — | — |
| Bio availability (% f) | — | — | — | 27.30 | — | — |

BLQ: Below limits of quantitation; NA: Not Applicable

Example 10

Use of compounds to inhibit the growth of tumors in mammalian (e.g., human) patients.

The aforementioned compounds are of use in the treatment of solid or liquid tumors that show upregulation of iron and/or HIF-2α. Many studies have shown upregulation of HIF-2α or iron in tumor tissue, and/or identified mechanisms by which increased HIF-2α or iron may promote the growth of tumors, whereas inhibition of HIF-2α or promotion of ferroptosis may inhibit tumor growth (Torti and Torti 2013, Chen, Hill et al. 2016, Lu, Chen et al. 2017). Thus, the aforementioned compounds provide benefits to these patients. In some embodiments, an appropriate dosage level of the inventive compounds may generally be about 0.01 to 1000 mg per kg patient body weight per day which is administered in single or multiple doses. In non-limiting examples, the dosage level may be about 0.1 to about 250 mg/kg per day; or about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Treatment with such compounds may result in patient benefit given by reduced tumor burden (demonstrated radiologically or otherwise by persons trained in the art), prolonged progression-free survival, decreased metastasis, or enhanced overall survival. Monitoring of drug efficacy may include the measurement of circulating ferritin, and/or measurement of HF-2a and other iron regulatory proteins described herein through biopsy of tumor sections.

We claim:

1. A compound of Formula I:

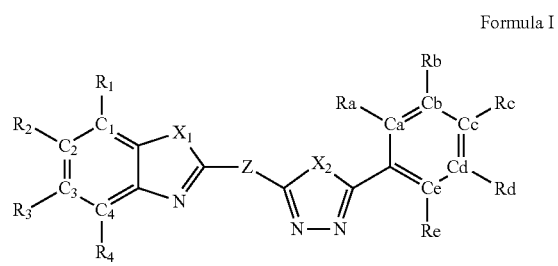

Formula I or a pharmaceutically acceptable salt thereof, wherein:
$X_1$ is NH;
$X_2$ is O;
Z is NH;
each of $C_1$, $C_2$, $C_3$, and $C_4$, ($C_{1\text{-}4}$) as independently, C or N, wherein at least one of $C_{1\text{-}4}$ is N;

when $C_1$ is N, then $R_1$ is not present;
when $C_2$ is N, then $R_2$ is not present;
when $C_3$ is N, then $R_3$ is not present;
when $C_4$ is N, then $R_4$ is not present;
when $C_1$ is C, then $R_1$ is H, $CH_3$,

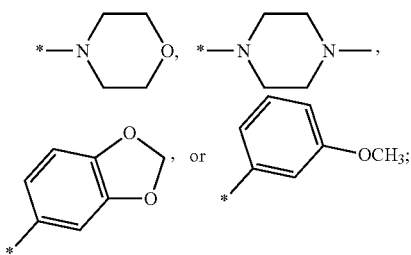

when $C_2$ is C, then $R_2$ is H, Cl, $CF_3$, $OCH_3$, or

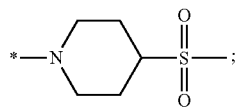 [SMILES: *N1CCC(S(C)(=O)=O)CC1]

when $C_3$ is C, then $R_3$ is H, $OCH_3$, $CF_3$,

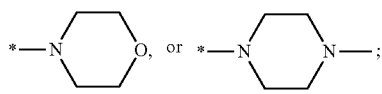

when $C_4$ is C, then $R_4$ is H, $OCH_3$, or

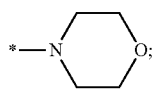

Ca, Cc, Cd, and Ce are each C;
Cb is C or N;
Ra is H or $OCH_3$;
when Cb is C, then Rb is H, F, or $OCH_3$, or together with Rc forms a methylenedioxy;
when Cb is N, then Rb is not present;
Rc is H, F, Cl, $CH_3$, $OCH_3$, CN, CF3, $OCF_3$, $SCH_3$, $N(CH_3)$, $OCH(CH_3)_2$

$C(CH_3)_3$

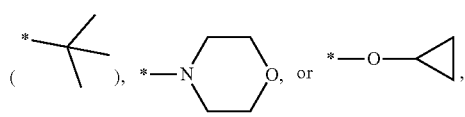

or together with Rb forms a methylenedioxy; and
Rd and Re are each H.

2. The compound of claim 1, wherein the compound is a compound of Formula Ia:

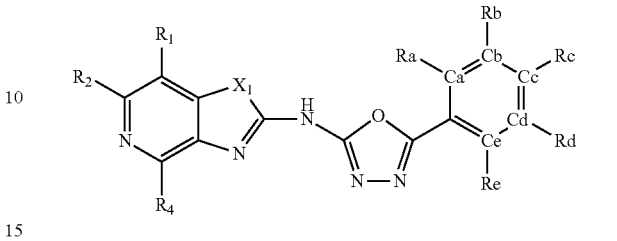

Formula Ia or a pharmaceutically acceptable salt thereof.

3. The compound of claim 1, wherein the compound is a compound of Formula Ib:

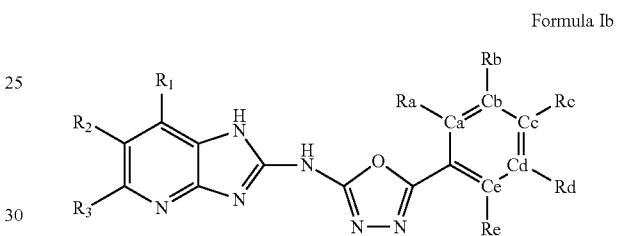

Formula Ib or a pharmaceutically acceptable salt thereof.

4. The compound of claim 1, wherein the compound is a compound of Formula Ic:

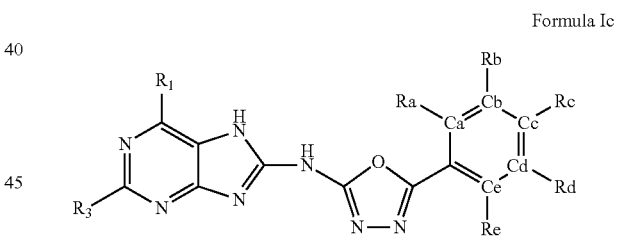

Formula Ic or a pharmaceutically acceptable salt thereof.

5. The compound of claim 1, wherein said compound is selected from the group consisting of:

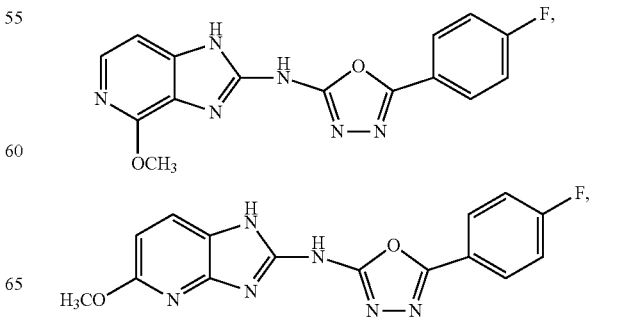

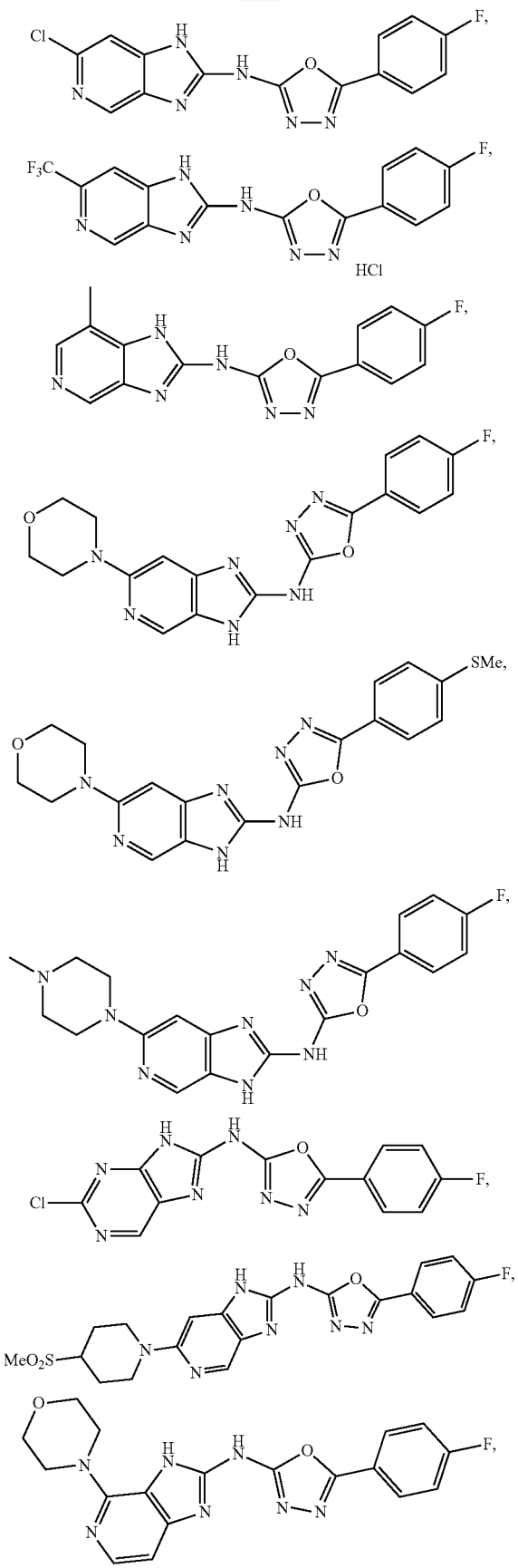
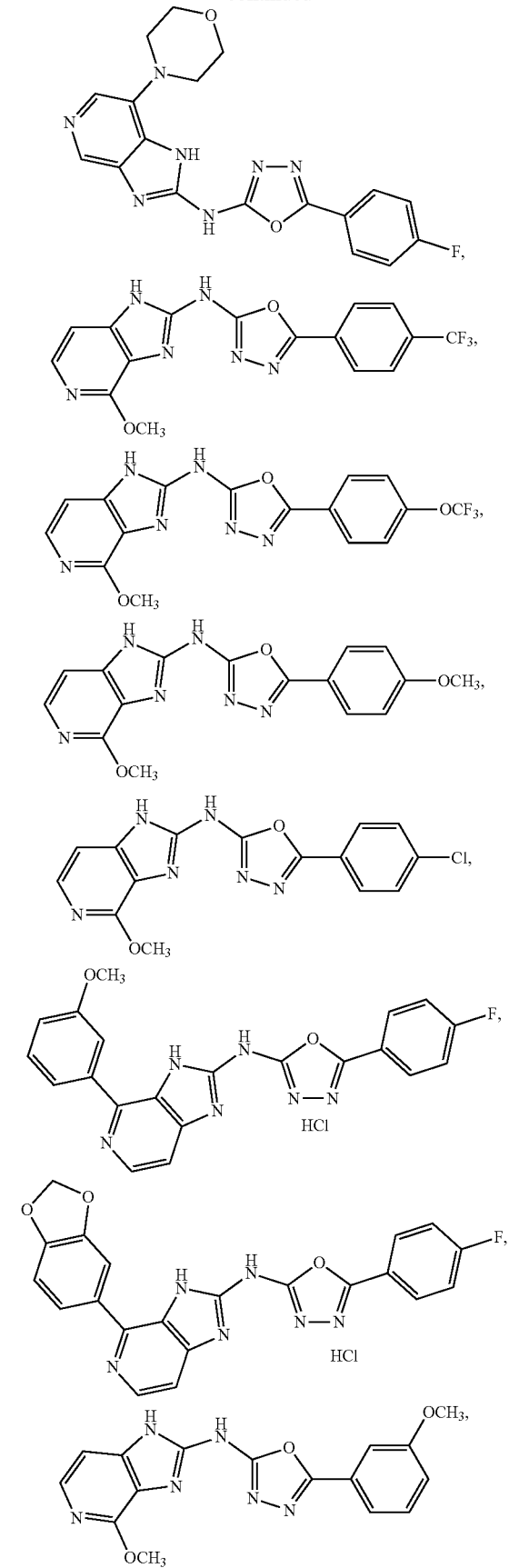

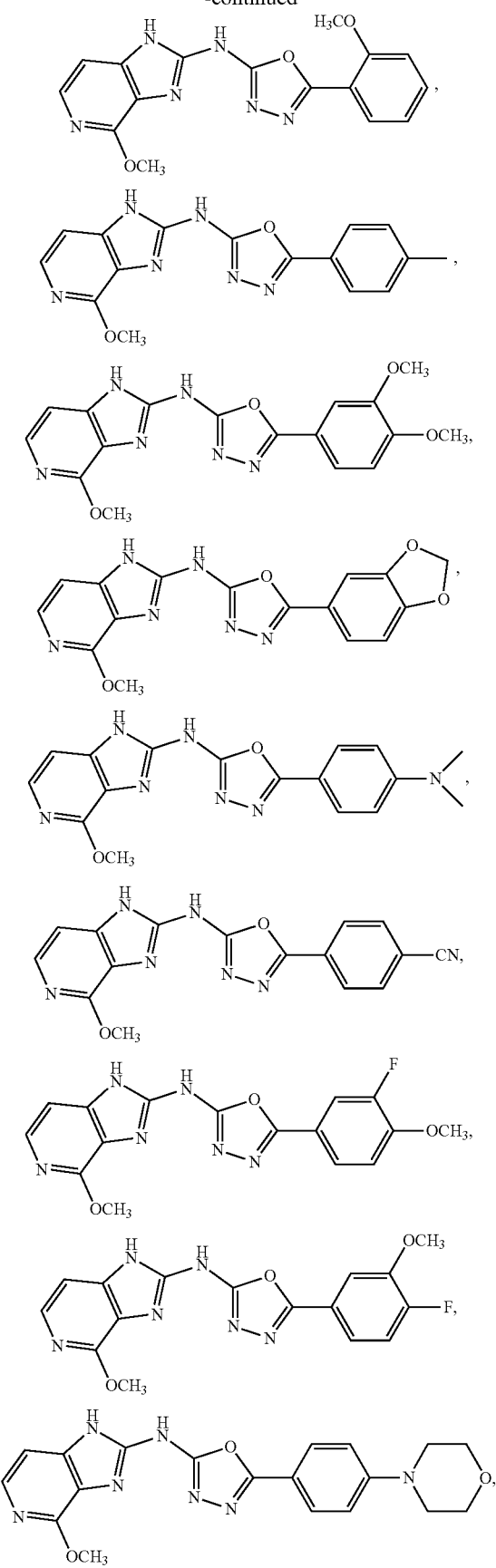

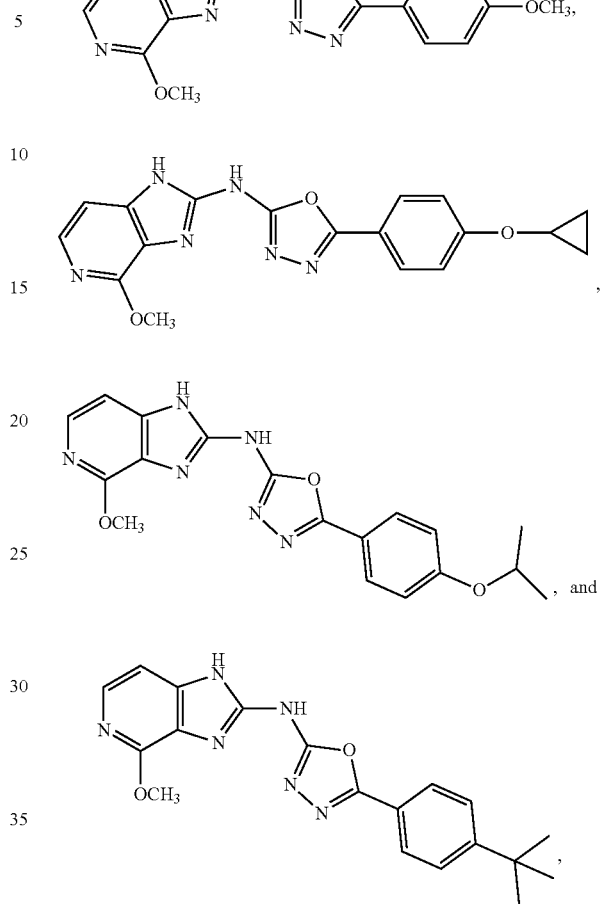

6. A pharmaceutical composition comprising a therapeutically effective amount of the compound of claim 1 and a pharmaceutically acceptable carrier.

7. A method for the treatment of a disorder of uncontrolled cellular proliferation in a mammal, the method comprising administering to the mammal an effective amount of the compound of claim 1.

8. A method of inducing ferroptosis in a cell, the method comprising administering to the cell the compound of claim 1.

9. A method of increasing the iron, and optionally the zinc and/or copper content of a cell, the method comprising administering to the cell the compound of claim 1.

10. A method of decreasing the amount of HIF-2α in a cell, the method comprising administering to the cell the compound of claim 1.

11. A method of binding ISCA2, the method comprising contacting ISCA2 with the compound of claim 1.

12. A method of inducing death of a cell through lipid peroxidation, the method comprising administering to the cell the compound of claim 1.

13. A method of inducing iron accumulation in a cell, the method comprising administering to the cell the compound of claim 1.

14. A compound of Formula I:

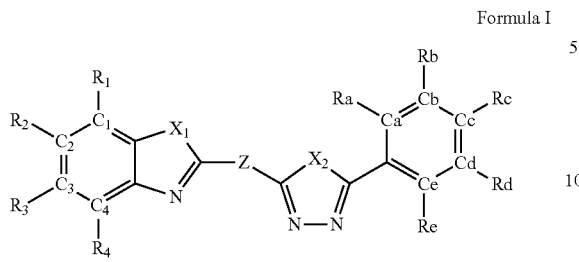

Formula I or a pharmaceutically acceptable salt thereof, wherein:

$X_1$ is NH;

$X_2$ is O;

Z is NH;

each of $C_1$, $C_2$, $C_3$, and $C_4$, ($C_{1-4}$) is, independently, C or N, wherein at least one of $C_{1-4}$ is N;

each of Ca, Cb, Cc, Cd, and Ce (Ca-e) is, independently, C or N;

each of $R_1$, $R_2$, $R_3$, and $R_4$, ($R_{1-4}$) and each of Ra, Rb, Rc, Rd, and Re (Ra-e):

(i) is, independently, selected from H, F, Cl, $CH_3$, $OCH_3$, CN, CF3, $OCF_3$, $SCH_3$, $N(CH_3)_2$, $OCH(CH_3)_2$

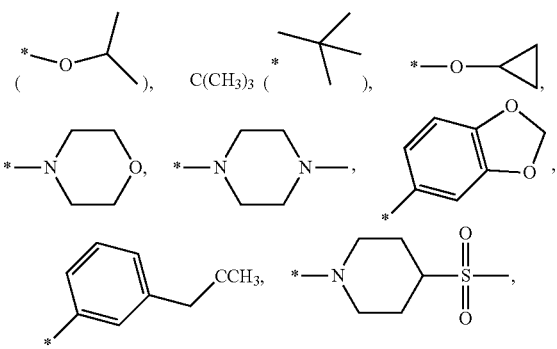

or, when the respective $C_{1-4}$ or Ca-e to which the respective $R_{1-4}$ or Ra-e is attached is N, then the said $R_{1-4}$ or Ra-e is not present; or (ii) together with an adjacent one of $R_{1-4}$ or Ra-e forms methylenedioxy.

15. The compound of claim 14, wherein the compound is a compound of Formula Ia, Formula Ib, or Formula Ic, or a pharmaceutically acceptable salt thereof:

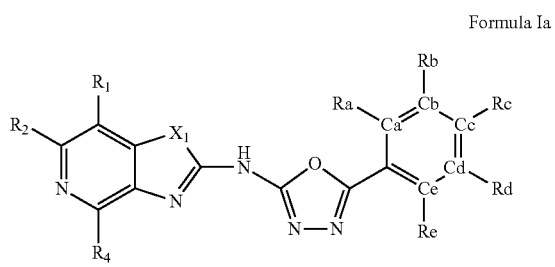

Formula Ia

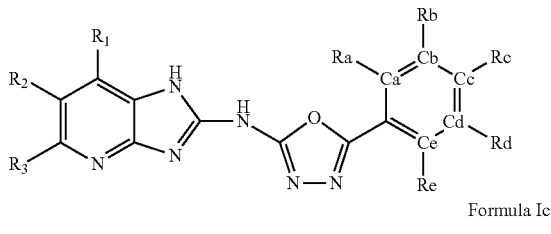

Formula Ib

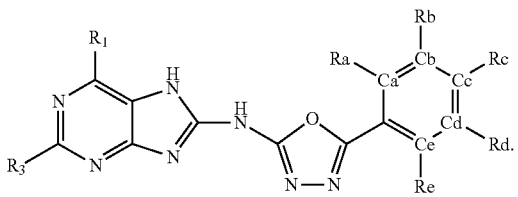

Formula Ic

16. A compound of Formula I:

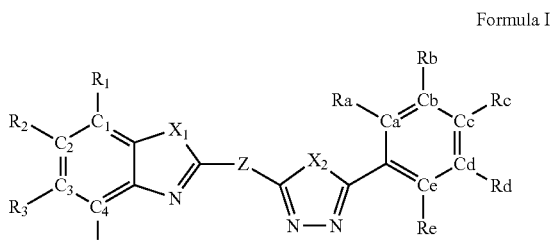

Formula I or a pharmaceutically acceptable salt thereof, wherein:

$X_1$ is O or NH;

$X_2$ is O or S or NH;

Z is $CH_2$ or O or S or $NR^A$, where $R^A$ is H or C1-4 alkyl;

each of $C_1$, $C_2$, $C_3$, and $C_4$, ($C_{1-4}$) and each of Ca, Cb, Cc, Cd, and Ce (Ca-e) is, independently, C or N, wherein at least one of $C_{1-4}$ is N; and each of $R_1$, $R_2$, $R_3$, and $R_4$, ($R_{1-4}$) and each of Ra, Rb, Rc, Rd, and Re (Ra-e):

(i) is, independently, selected from H, F, Cl, $CH_3$, $OCH_3$, CN, CF3, $OCF_3$, $SCH_3$, $N(CH_3)_2$, $OCH(CH_3)_2$

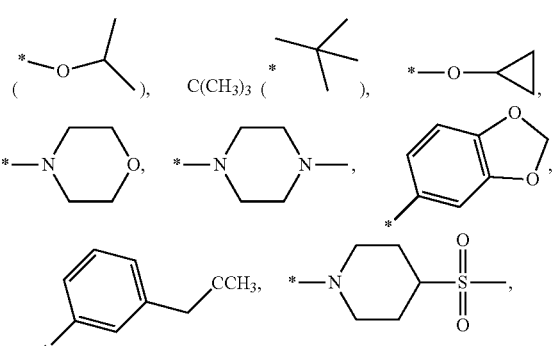

or, when the respective $C_{1-4}$ or Ca-e to which the respective $R_{1-4}$ or Ra-e is attached is N, then the said $R_{1-4}$ or Ra-e is not present; or (ii) together with an adjacent one of $R_{1-4}$ or Ra-e forms a methylenedioxy.

17. The compound of claim 16, wherein said compound is selected from the group consisting of:
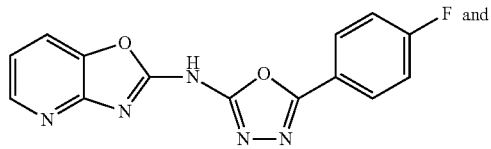
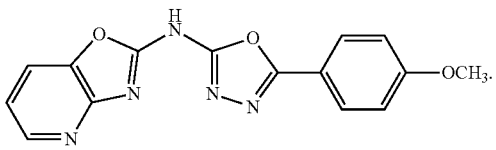
18. The compound of claim 16, wherein said compound is selected from the group consisting of:
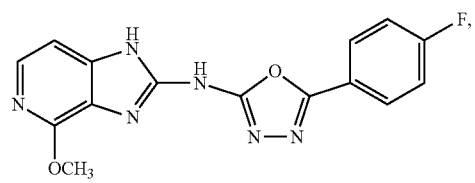
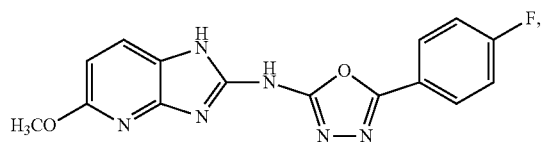
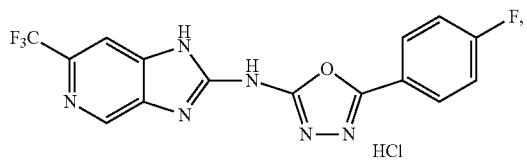
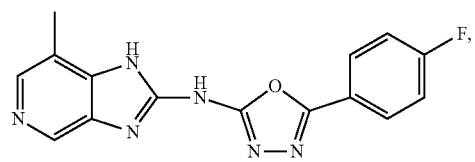
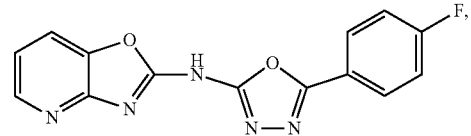
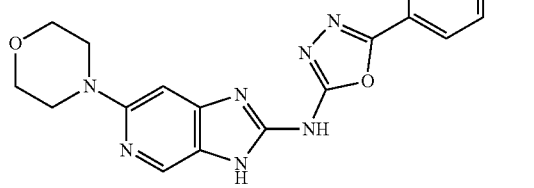
-continued
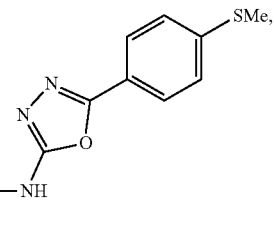
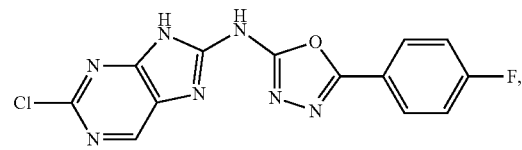
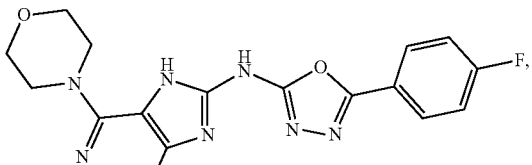
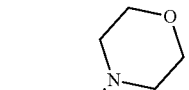
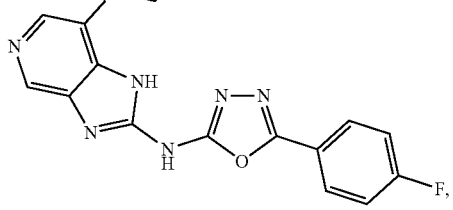
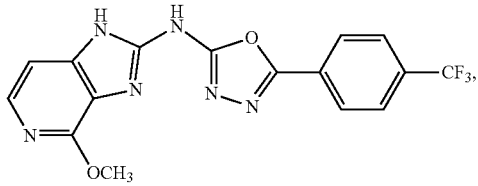
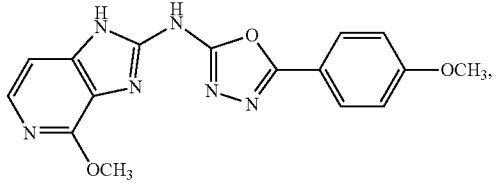
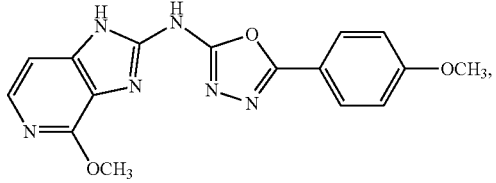
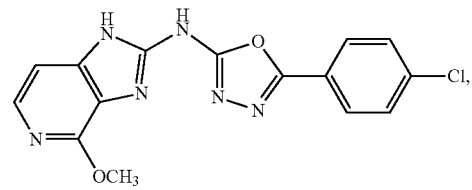

-continued
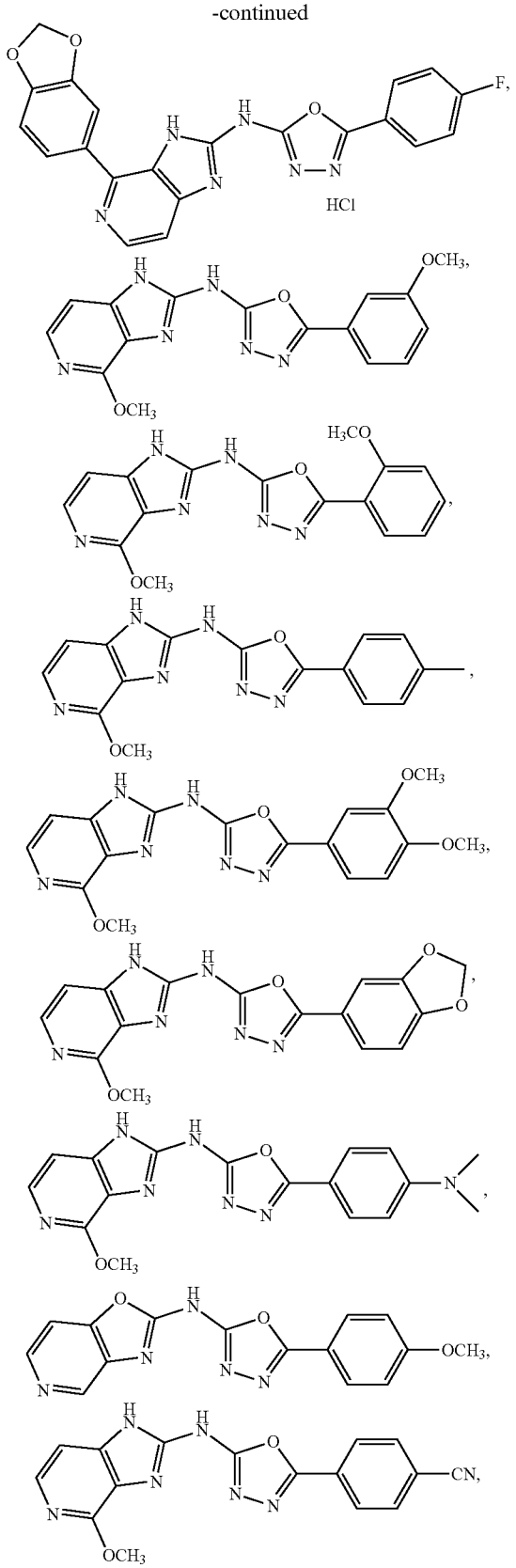
-continued
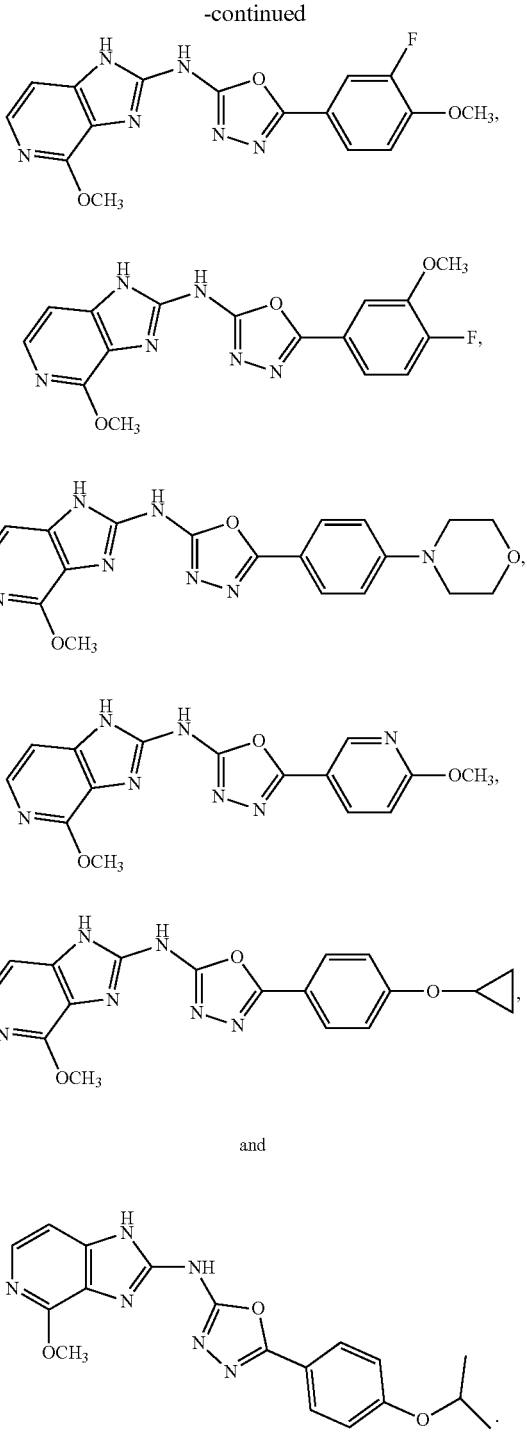
and
19. A pharmaceutical composition comprising a therapeutically effective amount of the compound of claim 16 and a pharmaceutically acceptable carrier.
20. A method of inducing iron accumulation in a cell, the method comprising administering to the cell the composition of claim 19.
* * * * *